United States Patent
Alig et al.

(10) Patent No.: US 6,320,054 B1
(45) Date of Patent: Nov. 20, 2001

(54) THIAZOLE DERIVATIVES

(75) Inventors: Leo Alig, Kaiseraugst; Albrecht Edenhofer, Riehen; Kurt Hilpert, Hofstetten; Thomas Weller, Basel, all of (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 09/526,033

(22) Filed: Mar. 15, 2000

Related U.S. Application Data

(62) Division of application No. 09/218,567, filed on Dec. 22, 1998, now Pat. No. 6,100,282.

(30) Foreign Application Priority Data

Jan. 2, 1998 (EP) .................................................. 98100006

(51) Int. Cl.[7] ........................ C07D 277/20; C07D 417/14
(52) U.S. Cl. ........................ 548/196; 546/256; 546/269.7; 548/200; 548/202; 548/204; 548/205; 514/371; 514/365; 514/342; 514/333
(58) Field of Search .................................. 548/196, 200, 548/202, 204, 205; 514/371, 365, 342, 333; 546/256, 269.7

(56) References Cited

U.S. PATENT DOCUMENTS

| | | |
|---|---|---|
| 4,785,008 | 11/1988 | Coquelet et al. . |
| 5,000,775 | 3/1991 | Grabiak et al. . |
| 5,430,024 | 7/1995 | Alig et al. . |
| 5,532,258 | 7/1996 | Katsura et al. ........................ 514/370 |

FOREIGN PATENT DOCUMENTS

| | | |
|---|---|---|
| 0 445 796 | 9/1991 | (EP) . |
| 0 519 738 | 12/1992 | (EP) . |
| 0 529 858 | 3/1993 | (EP) . |
| 0 639 574 | 2/1995 | (EP) . |
| 761 658 | 3/1997 | (EP) . |
| 2 009 155 | 6/1979 | (GB) . |
| 77375 | 4/1987 | (JP) . |
| 123180 | 6/1987 | (JP) . |
| 48873 | 9/1988 | (JP) . |
| 337579 | 12/1996 | (JP) . |
| 295974 | 11/1997 | (JP) . |
| WO 96/22966 | 8/1996 | (WO) . |
| WO 97/24343 | 7/1997 | (WO) . |

OTHER PUBLICATIONS

Islip, P.J. et al. : Substituted Thiazoltlureas. J. Med. Chem. vol. 15, pp. 101–103, Jan. 72.*
Schnur et al., J. Med. Chem., 34:914–918 (1991).
Plazzi et al., IL Farmaco, 44(11):1011–1030 (1989).
Barton et al., J.C.S. Perkin I, 159–164 (1982).
Chemical Abstract, vol. 127, No. 2, No. 17675n, (1997).

* cited by examiner

Primary Examiner—C. S. Aulakh
(74) Attorney, Agent, or Firm—George W. Johnston; William H. Epstein; John P. Parise

(57) ABSTRACT

Compounds of the formula:

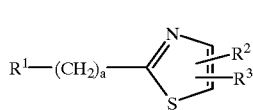

as well as pharmaceutically usable salts and esters thereof, wherein $R^1$, $R^2$ and $R^3$ have the significance ascribed herein, inhibit binding of adhesive proteins to the surface of different types of cell and accordingly influence cell-cell and cell-matrix interactions. These compounds can be used in the form of pharmaceutical preparations for the control or prevention of neoplasms, tumor metastasing, tumor growth, osteoporosis, Paget's disease, diabetic retinopathy, macular degeneration, restenosis following vascular intervention, psoriasis, arthritis, fibrosis, kidney failure, as well as infection caused by viruses, bacteria or fungi.

90 Claims, No Drawings

THIAZOLE DERIVATIVES

CROSS REFERENCE TO RELATED APPLICATIONS

This is a divisional of application Ser. No. 09/218,567, filed on Dec. 22, 1998 now U.S. Pat. No. 6,100,282, Aug. 8, 2000.

BACKGROUND OF THE INVENTION

The present invention is concerned with novel thiazole derivatives that inhibit binding of adhesive proteins to the surface of cells by influencing cell-cell and cell-matrix interactions.

SUMMARY OF THE INVENTION

The subject invention provides compounds having the formula:

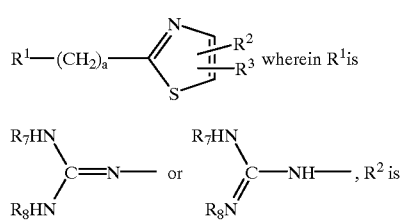

(I)

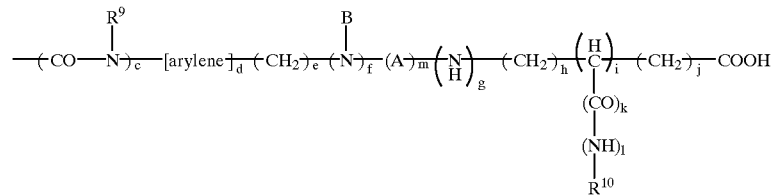

$R^3$ is hydrogen, alkyl, cycloalkyl, aryl, aralkyl, heteroaryl, carboxy, alkyl-O—CO—, or aralkyl-O—CO—;

$R^4$ is hydrogen, alkyl, cycloalkyl, aryl, or heteroaryl;

$R^5$ and $R^6$ are each independently hydrogen, alkyl, cycloalkyl, or heteroaryl;

$R^7$ and $R^8$ are each independently hydrogen, alkyl, cycloalkyl, or aralkyl, or $R^7$ and $R^8$ together with the N atoms to which they are attached form a 5- to 8-membered heterocyclic ring that is either unsubstituted or substituted with alkyl;

$R^9$ is hydrogen, alkyl, or cycloalkyl;

$R^{10}$ is aryl, aralkyl, heterocyclyl, heterocyclylalkyl, hydroxy, hydrogen, or alkyl, or $R^{10}$ is carboxy, carboxyalkyl, alkyl-O—CO—, aralkyl-O—CO—, alkyl-CO—, aralkyl-CO—, heteroarylalkyl-CO—, alkylsulphonyl, arylsulphonyl or heteroarylsulphonyl and k is zero, or $R^{10}$ is an $\alpha$-amino acid bonded via the amino group and l is zero and k is 1;

A is carbonyl or sulphonyl;

is hydrogen, alkyl, or cycloalkyl;

a is an integer from 0 to 2 but not being zero when $R^1$ is —$NH_2$; b is an integer from 0 to 4; c, d, f, g, k, l and m are each independently an integer from 0 to 1, whereby c, f and g are not simultaneously 0 and whereby m is not 0 when f or g is 1; i is an integer from 0 to 1, whereby k and l are also 0 when i is 0; e is an integer from 0 to 3; h is an integer from 0 to 5; j is an integer from 0 to 2; and the sum of e, h and j is an integer from 2 to 7;

and the pharmaceutically usable salts and esters thereof. Although recited as a single grouping, all combinations of the mentioned substituents are envisioned.

It is preferred that f and g are not both 1. It is also preferred where $R^2$ is

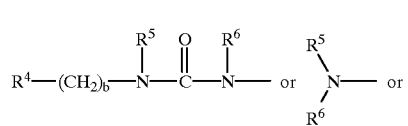

(II)

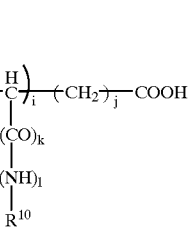

(III)

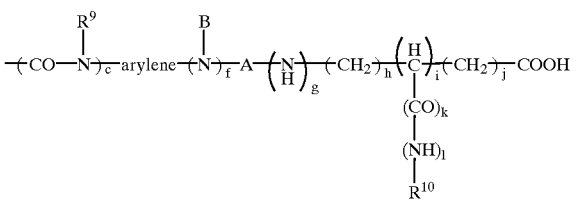

and $R^9$, $R^{10}$, A, B, c and f to l are as defined above, or (V)

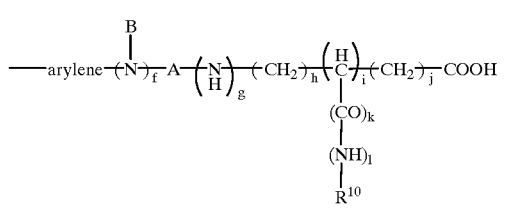

and $R^{10}$, A, B, and f to l are as defined above, or

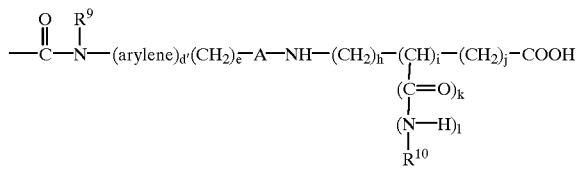
(VIa)

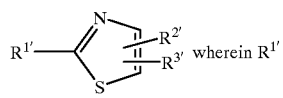 wherein $R^{1'}$

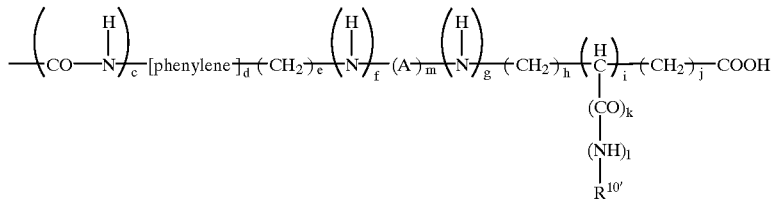

and $R^9$, $R^{10}$, A, d, e and h to l are as defined in claim 1, or

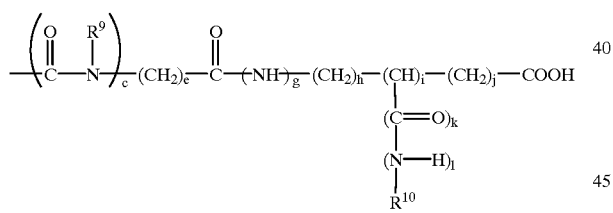
(VIc)

and $R^9$, $R^{10}$, C, e, g and h to l are as defined above, and c and g cannot simultaneously equal 0.

It is favored when arylene is phenylene or phenylene that is substituted with one or more substituents selected from the group consisting of alkoxy, aralkoxy, halogen, and alkoxy-alkoxy. Especially favored is where arylene is meta- or para-phenylene or substituted meta- or para-phenylene, with the substituents of the phenylene previously given by the definition of $R^2$ standing meta- or para- to one another and with the substituted phenylene carrying an additional substituent on the ring selected from the group of alkoxy, alkoxy-alkoxy, halogen or aralkoxy.

$R^3$ is preferably hydrogen, alkyl, cycloalkyl, alkyl-O—CO—, carboxy or unsubstituted or substituted phenyl, with the substituted phenyl being substituted by one or more substituents selected from halogen, nitro and amino. $R^4$ is preferably hydrogen, alkyl, cycloalkyl, phenyl, or pyridyl. $R^5$ and $R^6$ are preferably hydrogen or pyridyl and $R^7$ and $R^8$ are hydrogen, or $R^5$ and $R^6$ are each hydrogen or pyridyl and $R^7$ and $R^8$ together with the N atoms to which they are attached form a 5- or 6-membered ring. $R^{10}$ is preferably piperidyl, pyridylmethyl, pyridyl, benzyl, alkyl, hydrogen or substituted or unsubstituted phenyl, with the substituted phenyl being mono- or multiply-substituted by halogen, alkoxy, alkoxycarbonyl, carboxy or hydroxy, or $R^{10}$ is alkyl-O—CO-methyl, carboxymethyl, alkylsulphonyl, alkyl-CO—, benzyl-O—CO— or alkyl-O—CO—, with k being equal to zero, or $R^{10}$ is L-valine, L-phenylalanine, L-phenylglycine, L-leucine, L-isoleucine, L-serine, L-threonine, 3-(1-naphthyl)-L-alanine, 3-(2-naphthyl)-L-alanine, N-isopropyl-glycine, $^\beta$-cyclohexyl-L-alanine or L-proline, with k being equal to 1 and l being equal to zero.

Other preferred compounds include where $R^9$ is hydrogen or cycloalkyl and where $R^2$ is bonded to position 5 of the thiazole ring and $R^3$ is bonded to position 4 of the thiazole ring.

A favored subgenus is where compound of formula I is a compound having the formula:

1a

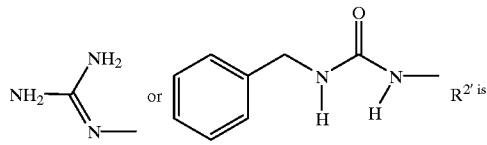
IIa

A is carbonyl or sulphonyl;

c, d, f, g, k, l and m are each independently an integer from 0 to 1, whereby c, f and g are not simultaneously 0 and whereby m is not 0 when f or g is 1; i is an integer from 0 to 1, whereby k and l are also 0 when i is 0; e is an integer from 0 to 3; h is an integer from 0 to 5; j is an integer from 0 to 2; and the sum of e, h and j is an integer from 2 to 7; and $R^{10'}$ is phenyl; phenyl substituted with halogen, hydroxy, or alkoxy; carboxy; carboxy alkyl, alkyl, or pyridine;

$R^{3'}$ is hydrogen or alkyl.

A preferred group of compounds is where $R^{1'}$ is

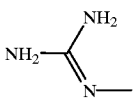

and $R^{3'}$ is alkyl, e.g. methyl or tert-butyl, A is carbonyl, and $R^{10'}$ is phenyl, phenyl substituted with chlorine, phenyl substituted with methoxy, or pyridine.

An alternative preferred group of compounds is where A is sulphonyl.

Another preferred group of compounds is where $R^{1'}$ is

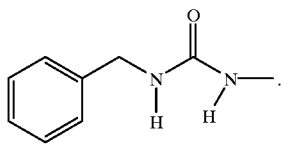

In such a group, it is preferred that $R^{3'}$ is hydrogen and $R^{10'}$ is phenyl, alkyl, or pyridine.

The subject invention provides a process for manufacturing compounds of formula I (as used for the remainder of the Summary of the Invention, the phrase "the compounds of formula I" also includes the pharmaceutically usable salts and esters of the formula I) which comprises reacting a compound of the formula:

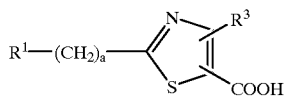
(XXXI)

with an amine of the formula:

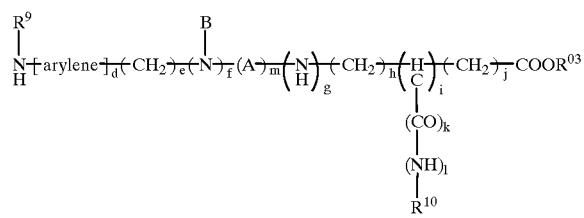
(XXXVII)

wherein $R^1$, $R^3$, $R^9$, $R^{10}$, A, B and d to m are as above, c is equal to 1 and $R^{03}$ is alkyl or aralkyl.

Novel intermediates in this process include compounds of the formula:

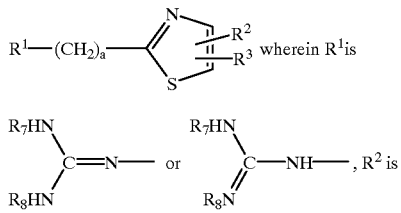
(I)

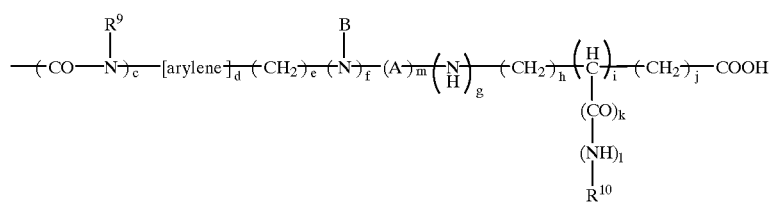
(II)

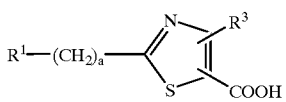
(XXXI)

wherein $R^1$ is

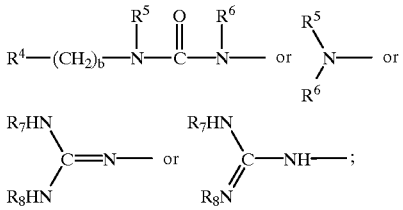

$R^3$ is alkyl, cycloalkyl, aryl, aralkyl, heteroaryl, carboxy, alkyl-O—CO—, or aralkyl-O—CO—, wherein $R^3$ is not hydrogen or methyl when $R^1$ is

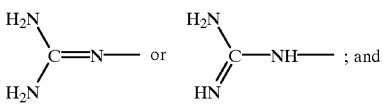
; and a is an integer from 0 to 2 but not being 0 when $R^1$ is —$NH_2$.

Pharmaceutical compositions provided by the subject invention include an effective amount of a compound of formula I and a pharmaceutically acceptable carrier.

The subject invention further provides a method for treating or preventing illnesses which are caused by a malfunction of the binding of adhesive proteins to vitronectin receptors, which comprises administering to a subject in need of such treating or preventing an effective amount of a compound of formula I.

DETAILED DESCRIPTION OF THE PREFERRED EMBODIMENTS

The invention will now be described in terms of its preferred embodiments. These embodiments are set forth to aid in understanding the invention but are not to be construed as limiting the invention.

The invention is concerned especially with thiazole derivatives of formula I

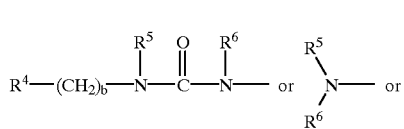

$R^3$ is hydrogen, alkyl, cycloalkyl, aryl, aralkyl, heteroaryl, carboxy, alkyl-O—CO— or aralkyl-O—CO—;

$R^4$ is hydrogen, alkyl, cycloalkyl, aryl or heteroaryl;

$R^5$ and $R^6$ are each independently hydrogen, alkyl, cycloalkyl or heteroaryl;

$R^7$ and $R^8$ are each independently hydrogen, alkyl, cycloalkyl or aralkyl or $R^7$ and $R^8$ together with the N atoms to which they are attached form a 5- to 8-membered heterocyclic ring which can be alkyl-substituted;

$R^9$ is hydrogen, alkyl or cycloalkyl;

$R^{10}$ is aryl, aralkyl, heterocyclyl, heterocyclylalkyl, hydroxy, hydrogen or alkyl, or $R^{10}$ is carboxy, carboxyalkyl, alkyl-O—CO—, aralkyl-O—CO—, alkyl-CO—, aralkyl-CO—, heteroarylalkyl-CO—, alkylsulphonyl, arylsulphonyl or heteroarylsulphonyl and k is zero, or $R^{10}$ is an $\alpha$-amino acid bonded via the amino group and l is zero and k is 1;

A is carbonyl or sulphonyl;

B is hydrogen, alkyl or cycloalkyl;

a to m are zero or whole positive numbers, with a being zero to 2 but not being zero when $R^1$ is —NH$_2$; b being zero to 4; c, d, f, g, k, l and m each independently being zero or 1, whereby c, f and g are not simultaneously zero and whereby m is not zero when f or g is 1; i is zero or 1, whereby k and l are also zero when i is zero; e is zero to 3; h is zero to 5; j is zero to 2; and the sum of e, h and j is 2 to 7;

and their pharmaceutically usable salts and esters.

The compounds of formula I and their pharmaceutically usable salts and esters are novel and have valuable pharmacological properties. In particular, they inhibit the binding of adhesive proteins such as fibrinogen, vitronectin, von Willebrand factor, fibronectin, thrombospondin and osteopontin to the vitronectin receptors (such as e.g. $\alpha_v\beta_3$, $\alpha_v\beta_5$, $\alpha_v\beta_6$, $\alpha_v\beta_8$, etc.) on the surface of various types of cell. The compounds therefore influence cell-cell and cell-matrix interactions and can be used in the treatment and prophylaxis of illnesses caused by a malfunction of the binding of adhesive proteins to vitronectin receptors. In particular, they can be used as vitronectin receptor antagonists in the prophylaxis or treatment of neoplasms, tumor metastasis, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi.

Objects of the present invention are the compounds of formula I and their aforementioned salts and esters per se and their use as therapeutically active substances, a process for the manufacture of the compounds, intermediates, pharmaceutical compositions, medicaments containing the compounds, their salts or esters, the use of the compounds, solvates and salts for the prophylaxis and/or therapy of illnesses, especially in the treatment or prophylaxis of, for example, neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi, and the use of the compounds and salts for the production of medicaments for the treatment or prophylaxis of, for example, neoplasms, tumor metastasing, tumor growth, osteoporosis, Paget's disease, diabetic retinopathy, restenosis following vascular intervention, psoriasis, arthritis, fibrosis, kidney failure as well as infections caused by viruses, bacteria or fungi.

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched $C_1$–$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl, ethyl, propyl, isopropyl, butyl, tert-butyl and pentyl.

The term "cycloalkyl", alone or in combination, signifies a cycloalkyl ring with 3 to 8 carbon atoms and preferably a cycloalkyl ring with 3 to 6 carbon atoms. Examples of $C_3$–$C_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methyl-cyclohexyl, dimethyl-cyclohexyl, cycloheptyl and cyclooctyl, preferably cyclopropyl and particularly cyclopentyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, preferably methoxy and ethoxy.

The term "alkoxy-alkoxy", alone or in combination, signifies an alkoxy group as previously defined in which one hydrogen atom has been replaced by an alkoxy group. Examples of alkoxy-alkoxy are methoxy-methoxy and methoxy-ethoxy, preferably 2-methoxy-ethoxy.

The term "aryl", alone or in combination, signifies a phenyl or naphthyl group which optionally carries one or more substituents each independently selected from alkyl, alkoxy, halogen, carboxy, alkoxycarbonyl, aminocarbonyl, hydroxy, amino, nitro and the like, such as phenyl, p-tolyl, 4-methoxyphenyl, 4-tert.butoxyphenyl, 4-fluorophenyl, 2-chlorophenyl, 3-chlorophenyl, 4-chlorophenyl, 4-hydroxyphenyl, 1-naphthyl and 2-naphthyl. Preferred are phenyl, alkoxy-phenyls, 2-hydroxy-3,5-dichlorophenyl, chlorophenyls, nitrophenyls and aminophenyls, especially phenyl and ortho-, meta- and para-mono-chlorophenyls, particularly para- and meta-chlorophenyl, and para- and meta-methoxy-phenyl.

The term "aryloxy", alone or in combination, signifies a group of the formula aryl-O— in which the term "aryl" has the previously given significance. Phenyloxy is an example of such an aryloxy group.

The term "aralkyl", alone or in combination, signifies an alkyl or cycloalkyl group as previously defined in which one hydrogen atom has been replaced by an aryl group as previously defined, such as benzyl, 2-phenylethyl and the like, preferably benzyl.

The term "aralkoxy", alone or in combination, signifies an alkoxy group as previously defined in which one hydrogen atom has been replaced by an aryl group as previously defined. Benzyloxy is a preferred example of an aralkoxy group.

The term "arylene", alone or in combination, signifies a phenylene or naphthylene group which optionally carries one or more substituents selected from alkyl, cycloalkyl, alkoxy, halogen, hydroxy, amino, nitro, aryloxy, aralkoxy and alkoxy-alkoxy, preferably alkoxy, benzyloxy, chloro and alkoxy-alkoxy. Examples are ortho-, meta- or para-phenylenes, the tolylenes, the methoxyphenylenes, the tert-butoxyphenylenes, the fluorophenylenes, the chlorophenylenes, the hydroxyphenylenes, the naphthylenes, the benzyloxyphenylenes etc. Preferred are meta- and parphenylenes, with the substituents of the phenylene previously given by the definition of $R^2$ standing meta- or para- to each other and with additionally one or more substituents selected from alkyl, cycloalkyl, alkoxy, halogen, hydroxy, amino, aryloxy and alkoxy-alkoxy optionally being present on the arylene ring. Especially preferred are meta- and para- phenylene which additionally carry a substituent selected from alkoxy, benzyloxy, chloro and alkoxy-alkoxy, particularly methoxy-phenylene, benzyloxyphenylene and 2-methoxy-ethoxy-phenylene. Quite particularly preferred are meta- and para- phenylene.

The term "heterocyclyl", alone or in combination, signifies a saturated, partially unsaturated or aromatic 5- to 10-membered heterocycle which contains one or more hetero atoms selected from nitrogen, oxygen and sulphur. If desired, it can be substituted on one or more carbon atoms by halogen, alkyl, alkoxy, oxo etc. and/or on a secondary nitrogen atom (i.e. -NH-) by alkyl, cycloalkyl, aralkoxycarbonyl, alkanoyl, phenyl or phenylalkyl or on a tertiary nitrogen atom (i.e. -N-) by oxido, with halogen, alkyl, cycloalkyl and alkoxy being preferred. Examples of such heterocyclyl groups are pyrrolidinyl, piperidinyl, piperazinyl, morpholinyl, thiomorpholinyl, pyrazoyl, imidazoyl (e.g. imidazol-4-yl and 1-benzyloxycarbonyl-imidazol-4-yl), pyrazoyl, pyridyl, pyrazinyl, pyrimidinyl, hexahydropyrimidinyl, furyl, thienyl, thiazolyl, oxazolyl, indolyl (e.g. 2-indolyl), quinolyl (e.g. 2-quinolyl, 3-quinolyl and 1-oxido-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxo-isoquinolyl) and quinoxalinyl. Preferred are 5- or 6-membered rings, especially piperidyl and pyridyl.

The term "heteroaryl", alone or in combination, signifies the aromatic compounds which fall under the definition of "heterocyclyl" and which can carry the substituents described there. Preferred are 5- and 6-membered rings, especially pyridyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably chlorine or bromine, and particularly chlorine.

As examples of "$\alpha$-amino acids" bonded via the amino group there come into consideration $\alpha$-amino acids having the L- or D-configuration in which the carboxyl group present is optionally derivatized as an ester or amide. Examples of such $\alpha$-amino acids are L-valine, L-phenylalanine, L-leucine, L-isoleucine, L-serine, L-threonine, 3-(1-naphthyl)-L-alanine, 3-(2-naphthyl)-L-alanine, N-isopropyl-glycine, $\beta$-cyclohexyl-L-alanine, L-phenylglycine and L-proline. Preferred are alanine, valine, phenylanine, leucine, $\beta$-cyclohexyl-alanine and phenylglycine, especially phenylglycine and valine.

The term "carboxy", alone or in combination, signifies a —COOH group.

The term "carboxyalkyl" alone or in combination, signifies an alkyl group as previously described in which one hydrogen atom has been replaced by a carboxy group. The carboxymethyl group is preferred.

The term "alkyl-O—CO—", alone or in combination, signifies an alkyl ester group, with alkyl being as previously defined. The methyl ester, ethyl ester, isomeric propyl ester and isomeric butyl ester groups are preferred. The methyl ester, ethyl ester and tert.butyl ester groups are especially preferred.

The term "alkyl-CO—", alone or in combination, signifies an alkylcarbonyl group, with alkyl being as previously defined. Examples are methylcarbonyl, ethylcarbonyl and the isomeric propylcarbonyls and butylcarbonyls. Ethylcarbonyl is particularly preferred.

The term "aralkyl-O—CO—", alone or in combination, signifies an aralkyl ester group, with aralkyl being as previously defined. The benzyl ester group is especially preferred.

The term "heterocyclylalkyl", alone or in combination, signifies an alkyl group as previously defined in which one hydrogen atom has been replaced by a heterocyclyl group. Examples of such heterocyclylalkyls are pyridylmethyl and piperidylmethyl.

The term "heteroarylalkyl", alone or in combination, signifies an alkyl group as previously defined in which one hydrogen atom has been replaced by a heteroaryl group. Preferred are, for example, 2-pyridylmethyl and 3-pyridylmethyl.

The term "alkylsulphonyl", alone or in combination, signifies a

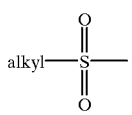

group in which Alkyl is as previously defined. Preferred alkylsulphonyls are methylsulphonyl, ethylsulphonyl and especially propylsulphonyl.

The term "arylsulphonyl", alone or in combination, signifies a

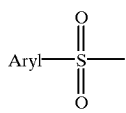

group in which Aryl is as previously defined. Preferred arylsulphonyls are phenylsulphonyl, 1-naphthylsulphonyl, p-toluenesulphonyl and 2-naphthylsulphonyl.

The term "heteroarylsulphonyl", alone or in combination, signifies a

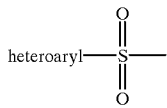

group in which heteroaryl is as previously defined. Preferred heteroarylsulphonyls are 2-thiophenesulphonyl and 3,5-dimethylisoxazol-4-sulphonyl.

Examples of physiologically usable salts of the compounds of formula I are salts with physiologically compatible mineral acids such hydrochloric acid, sulphuric acid or phosphoric acid; or with organic acids such as methanesulphonic acid, acetic acid, trifluoroacetic acid, citric acid, fumaric acid, maleic acid, tartaric acid, succinic acid or salicylic acid. The compounds of formula I with free carboxy groups can also form salts with physiologically compatible bases. Examples of such salts are alkali metal, alkali earth metal, ammonium and alkylammonium salts such as the Na, K, Ca or tertramethylammonium salt. The compound of formula I can also be present in the form of zwitterions.

In the nomenclature used in the present description the ring atoms of the thiazole ring are numbered as follows:

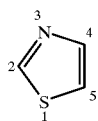

in which substituent $R^1$ is bonded to position 2, substituent $R^2$ is bonded to position 4 and $R^3$ is bonded to position 5:

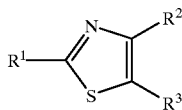

or substituent R² is bonded to position 5 and substituent R³ is bonded to position 4 of the thiazole ring:

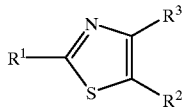

The invention expressly includes pharmaceutically suitable derivatives of the compounds of formula I. For example, the COOH groups in R² can be esterified. The alkyl and aralkyl esters are examples of suitable esters. The methyl, ethyl, propyl, butyl, benzyl and (R/S)-1-((isopropoxy-carbonyl)-oxy)-ethyl esters are preferred esters. The methyl, ethyl and tert.butyl esters are especially preferred.

The compounds of formula I can also be solvated, e.g. hydrated. The solvation can be effected in the course of the manufacturing process or can take place e.g. as a consequence of hygroscopic properties of an initially anhydrous compound of formula I (hydration).

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

A preferred embodiment of the invention comprises compounds of formula I in which f and g are not both simultaneously 1.

A further preferred embodiment comprises compounds of formula I in which f and g are not the same.

Preferred compounds of formula I are also those in which R² is

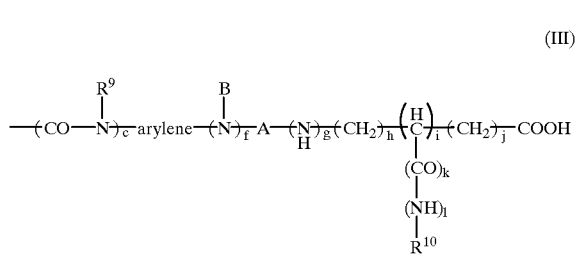

(III)

especially those in which R² is

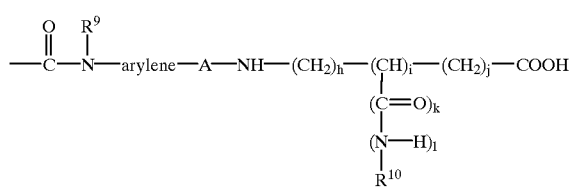

(IVa)

Also preferred are compounds of formula I in which R² is

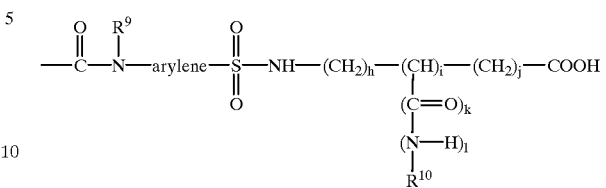

(IVb)

Likewise preferred compounds of formula I are those in which R² is

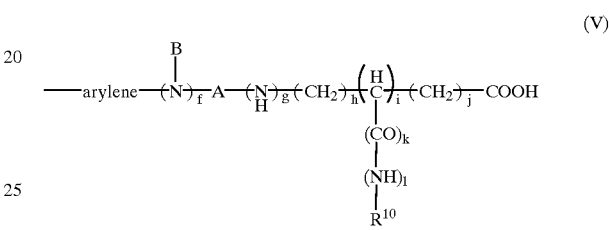

(V)

Preferred compounds are compounds of formula I in which R² is bonded to position 5 and R³ is bonded to position 4 of the thiazole ring. Especially preferred compounds of formula I are those in which R² is defined in accordance with formula III, to IVa, IVb or V and is bonded to position 5 of the thiazole ring with R³ being bonded to position 4 of the thiazole ring.

Likewise preferred compounds of formula I are those in which R² is

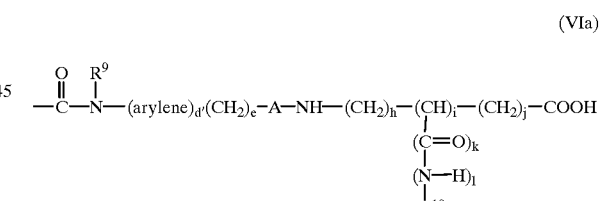

(VIa)

or

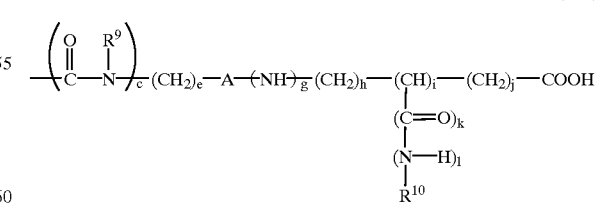

(VIb)

and wherein in compounds of formula VIb g is equal to 1 when c stands for zero.

Also preferred are compounds of formula I in which $R^2$ is

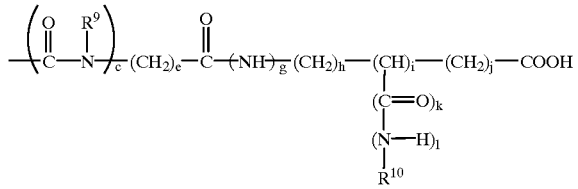
(VIc)

and in which g is equal to 1 when c is equal to zero.

Likewise preferred are compounds of formula I in which $R^2$ is

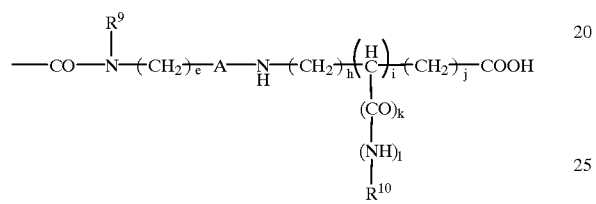
(VId)

The compounds of formula I in which $R^2$ is equal to formula VId, A is equal to carbonyl and $R^2$ is bonded to position 4 of the thiazole ring are especially preferred. The compounds in which $R^2$ is equal to formula VId, A is equal to carbonyl, e is equal to 1 and $R^2$ is bonded to position 4 of the thiazole ring are particularly preferred.

Also preferred is the embodiment of the invention in which in formula I f and g are both 1, $R^2$ corresponds to formula V, A is carbonyl and B is hydrogen.

Furthermore, the compounds of formula I in which c is 1, d is zero, f and g are both zero and A is equal to carbonyl are preferred.

Likewise preferred are the compounds of formula I in which c is 1, d is 1 and f, g and m are zero.

Preferred compounds of the above-described are compounds in which arylene is a phenylene or substituted phenylene in which the phenylene can be mono- or multiply substituted with alkoxy, alkoxy-alkoxy, halogen, aralkoxy, especially benzyloxy. Especially preferred are compounds in which arylene is meta- or para-phenylene or substituted meta- or para-phenylene in which the substituents of the phenylene previously given by the definitions of $R^2$ stand meta- or para- to one another and in which the substituted phenylene carries on the ring one or more additional substituents selected from the group of alkoxy, alkoxy-alkoxy, halogen or aralkoxy, especially benzyloxy.

Especially preferred are compounds in which arylene is meta- or para- phenylene or substituted meta- or para-phenylene in which the substituents of the phenylene previously given by the definitions of $R^2$ stand meta- or para- to one another and in which the substituted phenylene carries on the ring an additional substituent selected from the group of alkoxy, alkoxy-alkoxyhalogen or aralkoxy, especially benzyloxy. Especially preferred substituents on the phenylene are methoxy, 2-methoxy-ethoxy, chlorine and benzyloxy.

Compounds of formula I in which arylene is meta- or para-phenylene are especially preferred.

To the preferred compounds described above there belong those in which $R^1$ is

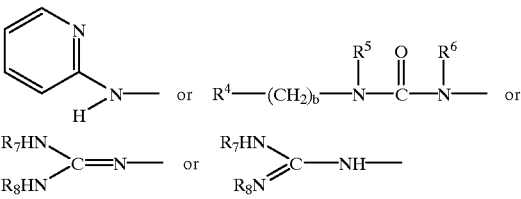

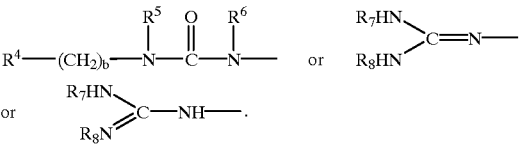

Especially preferred are compounds of formula I in which $R^1$ is

Also preferred are compounds of formula I in which $R^3$ is hydrogen, alkyl, cycloalkyl, carboxy, alkyl-O—CO— or substituted or unsubstituted phenyl, with the substituted phenyl being substituted by one or more substituents, preferably one substituent, selected from the group of halogen, nitro and amino, preferably nitro and/or amino. Particularly preferred significances of $R^3$ are the following: hydrogen, methyl, ethyl, propyl, isopropyl, butyl, tert-butyl, pentyl, cyclopentyl, methyl-O—CO—, carboxy, phenyl, nitrophenyl and aminophenyl.

A group of preferred compounds of formula I comprises those in which $R^4$ is hydrogen, alkyl, cycloalkyl, phenyl or pyridyl. Especially preferred are compounds of formula I in which $R^4$ is hydrogen, alkyl, phenyl or pyridin-2-yl.

To the group of preferred compounds of formula I also belong those in which $R^5$ and $R^6$ are hydrogen or pyridyl, preferably hydrogen, and $R^7$ and $R^8$ are hydrogen or $R^5$ and $R^6$ are each hydrogen or pyridyl, preferably hydrogen, and $R^7$ and $R^8$ together with the N atoms to which they are attached form a 5- or 6-membered ring, especially an imidazolidine or hexahydropyrimidine ring. Especially preferred are the compounds of formula I in which $R^7$ and $R^8$ together with the N atoms to which they are attached form an imidazolidine ring. Particularly preferred are those compounds of formula I in which $R^5$, $R^6$, $R^7$ and $R^8$ are hydrogen.

Also preferred is the group of compounds of formula I which $R^9$ is hydrogen or cycloalkyl. The compounds in which $R^9$ is hydrogen or cyclopropyl are especially preferred. Of these the compounds, in which $R^9$ is hydrogen are particularly preferred.

Preferred compounds of formula I are those in which $R^{10}$ is piperidyl, pyridylmethyl, pyridyl, benzyl, alkyl, hydrogen or substituted or unsubstituted phenyl, with the substituted phenyl being mono- or multiply-substituted by halogen, alkoxy, alkoxycarbonyl, carboxy or hydroxy, or $R^{10}$ is alkyl-O—CO-methyl, carboxymethyl, alkylsulphonyl, alkyl-CO—, benzyl-O—CO— or alkyl-O—CO—, whereby here k is zero.

Furthermore, preferred compounds of formula I are those in which $R^{10}$ is an $\alpha$-amino acid bonded via the amino group, with l being zero and k being 1, especially in which $R^{10}$ is L-valine, L-phenylalanine, L-phenylglycine, L-leucine, L-isoleucine, L-serine, L-threonine, 3-(1-naphthyl)-L-alanine, 3-(2-naphthyl)-L-alanine, N-isopropyl-glycine, $\beta$-cyclohexyl-L-alanine or L-proline, particularly L-valine or L-phenylglycine, and l being zero and k being 1.

A preferred embodiment of the invention comprises compounds of formula I in which A is carbonyl.

A further preferred embodiment of the invention comprises compounds of formula I in which A is sulphonyl and $R^2$ corresponds to formula VIa. Especially preferred are the compounds of formula I in which A is sulphonyl, $R^2$ corresponds to formula Via, d is 1 and e is zero.

Also preferred are compounds of formula I in which B is hydrogen or alkyl and especially those in which B is hydrogen or methyl. In a particularly preferred embodiment B is hydrogen.

A group of preferred compounds of formula I comprises those in which $R^1$ is $$R^4-(CH_2)_b-\underset{R^6}{\overset{R^5}{N}}-\underset{}{\overset{O}{\underset{\|}{C}}}-\underset{}{\overset{R^6}{N}}- \quad \text{or} \quad \underset{R_8HN}{\overset{R_7HN}{}}\!\!\!\!\!\!\!\!\!\!\!\!\!\!\!\!\!\!\!N- \quad \text{or} \quad \underset{R_8N}{\overset{R_7HN}{}}\!\!\!\!\!\!\!\!\!\!\!\!\!\!\!\!\!\!C=N- \quad \text{or} \quad \underset{R_8N}{\overset{R_7HN}{}}\!\!\!\!\!\!\!\!\!\!\!\!\!\!\!\!\!\!C-NH-, R^2 \text{ is}$$

$$\left(\underset{}{\overset{O}{\underset{\|}{C}}}-\underset{R^9}{\overset{}{N}}\right)_c\text{(arylene)}_{d'}(CH_2)_e-(NH)_f-A-(NH)_g-(CH_2)_h-(CH)_i-(CH_2)_j-COOH, \quad (II)$$

with branch: $(C=O)_k-(N-H)_l-R^{10}$ $R^3$ is hydrogen, alkyl cycloalkyl, aryl, aralkyl or heteroaryl, $R^4$ is hydrogen, alkyl, cycloalkyl, aryl or heteroaryl, $R^5$, $R^6$, $R^7$ and $R^8$ are each independently hydrogen, alkyl or cycloalkyl or $R^7$ and $R^8$ together with the N atoms to which they are attached form a 5- to 8-membered heterocyclic ring which can be mono- or multiply-substituted by alkyl, $R^9$ is hydrogen, alkyl or cycloalkyl, $R^{10}$ is aryl, aralkyl or heterocyclyl, or $R^{10}$ is an $\alpha$-amino acid bonded via the amino group, with l being zero and k being 1, A is carbonyl or sulphonyl, a to l are zero or whole positive numbers, with a being zero to 2, but not being zero when $R^1$ is —$NH_2$, b being zero to 4, c, d, f, g, k and l each independently being zero or 1 and c, f and g not all three simultaneously being zero, i being zero or 1 and k and l being zero when i is zero, e is zero to 3, h is zero to 5, j is zero to 2 and the sum of e, h and j is 2 to 7;

and pharmaceutically salts and esters thereof.

A further group of preferred compounds of formula I comprises those in which $R^1$ is

[pyridyl-NH—  or  $R^4-(CH_2)_b-\underset{R^6}{\overset{R^5}{N}}-\underset{}{\overset{O}{\underset{\|}{C}}}-\underset{}{\overset{R^6}{N}}-$  or  $\underset{R_8HN}{\overset{R_7HN}{}}C=N-$  or  $\underset{R_8N}{\overset{R_7HN}{}}C-NH-$]

$R^2$ is a substituent defined by formula III, IVa, IVb, V, VIa, VIb, VIc or VId, whereby in formulas VIb and VIc g is 1 when c is zero, $R^3$ is hydrogen, alkyl, cycloalkyl, carboxy, alkyl-O—CO— or substituted or unsubstituted phenyl, with substituted phenyl being mono- or multiply-substituted by halogen, nitro and/or amino, $R^4$ is hydrogen, alkyl, cycloalkyl, phenyl or pyridyl, $R^5$ and $R^6$ are hydrogen or pyridyl, preferably hydrogen, and $R^7$ and $R^8$ are hydrogen, or $R^5$ and $R^6$ are each hydrogen or pyridyl and $R^7$ and $R^8$ together with the N atoms to which they are attached form a 5- or 6-membered ring, especially an imidazolidine or hexahydropyrimidine ring, $R^9$ is hydrogen or cycloalkyl, $R^{10}$ is piperidyl, pyridylmethyl, pyridyl, benzyl, alkyl, hydrogen or substituted or unsubstituted phenyl, with the substituted phenyl being mono- or multiply-substituted by halogen, alkoxy, alkoxycarbonyl, carboxy or hydroxy, or $R^{10}$ is alkyl-O—CO-methyl, carboxymethyl, alkylsulphonyl, alkyl-CO—, benzyl-O—CO— or alkyl-O—CO—O, with k being zero, or $R^{10}$ is an $\alpha$-amino acid bonded via the amino group, with l being zero and k being 1, and especially $R^{10}$ is L-valine, L-phenylalanine, L-phenylglycine, L-leucine, L-isoleucine, L-serine, L-threonine, 3-(1-naphthyl)-L-alanine, 3-(2-naphthyl)-L-alanine, N-isopropyl-glycine, $\beta$-cyclohexyl-L-alanine or L-proline and l is zero and k is 1, B is hydrogen or alkyl and arylene signifies phenylene or substituted phenylene, with the phenylene being optionally mono- or multiply-substituted by alkoxy, alkoxy-alkoxy, halogen or aralkoxy.

A group of especially preferred compounds of formula I comprises those in which $R^1$ is $$R^4-(CH_2)_b-\underset{}{\overset{R^5}{N}}-\underset{}{\overset{O}{\underset{\|}{C}}}-\underset{}{\overset{R^6}{N}}- \quad \text{or} \quad \underset{R_8HN}{\overset{R_7HN}{}}C=N- \quad \text{or}$$

$$\underset{R_8N}{\overset{R_7HN}{}}C-NH-,$$

$R^2$ is a substituent defined by formula III, IVa, IVb, V, VIa, VIb, VIc or VId, whereby in formulas VIb and VIc g is 1 when c is zero, $R^3$ is hydrogen, methyl, ethyl, propyl, isopropyl, butyl, tert-butyl, pentyl, cyclopentyl, methyl-O—CO—, carboxy, phenyl, nitrophenyl or aminophenyl, $R^4$ is hydrogen, alkyl, phenyl or pyridin-2-yl, $R^5$, $R^6$, $R^7$ and $R^8$ are hydrogen, $R^9$ is hydrogen or cyclopropyl, $R^{10}$ is piperidyl, pyridylmethyl, pyridyl, benzyl, alkyl, hydrogen or substituted or unsubstituted phenyl, with the substituted phenyl being mono- or multiply-substituted by halogen, alkoxy, alkoxycarbonyl, carboxy or hydroxy, or $R^{10}$ is alkyl-O—CO-methyl, carboxymethyl, alkylsulphonyl, alkyl-CO—, benzyl-O—CO— or alkyl-O—CO—, with k being zero, or $R^{10}$ is L-valine or L-phenylglycine and l being zero and k being 1, B is hydrogen or methyl and arylene signifies meta- or para-phenylene or substituted meta- or para-phenylene, with the substituents of the phenylene previously given by the definition of $R^2$ standing meta- or para- to one another and the substituted phenylene carrying on the ring an additional substituent selected from the group of alkoxy, alkoxy-alkoxy, halogen and aralkoxy.

A preferred substitution pattern on the thiazole ring comprises the above compounds in which $R^2$ is arranged on position 5 and $R^3$ is arranged on position 4 of the thiazole rings. This applies especially when $R^2$ represents a substituent of formula III, IVa, IVb or V.

Examples of preferred compounds of formula I are:

Ethyl 3-[3-[(2-guanidino-4-methyl-thiazole-5-carbonyl)-amino]-propionylamino]-propionate, 3-[3-[(2-guanidino-4-methyl-thiazole-5-carbonyl)-amino]-propionylamino]-propionic acid hydrochloride, ethyl 3-[3-[(2-guanidino-thiazole-4-carbonyl)-amino]-propionylamino]-propionate, 3-[3-[(2-guanidino-thiazole-4-carbonyl)-amino]-propionylamino]-propionic acid hydrochloride, 3-[3-[(2-guanidino-4-methyl-thiazole-5-carbonyl)-amino]-benzoylamino]-propionic acid trifluoroacetate, ethyl rac 3-[3-[(2-guanidino-4-methyl-thiazole-5-carbonyl)-amino]-benzoylamino]-3-phenyl-propionate, rac 3-[3-[(2-guanidino-4-methyl-thiazole-5-carbonyl)-amino]-benzoylamino]-3-phenyl-propionic acid hydrochloride, ethyl rac 3-[2-[(2-guanidino-thiazole-5-carbonyl)-amino]-acetylamino]-3-phenyl-propionate, rac 3-[2-[(2-guanidino-thiazole-5-carbonyl)-amino]-acetylamino]-3-phenyl-propionic acid hydrochloride, ethyl rac-6-{[2-(3-benzyl-ureido)-thiazole-4-carbonyl]-amino}-3-phenyl-hexanoate, rac-6-{[2-(3-benzyl-ureido)-thiazole-4-carbonyl]-amino}-3-phenyl-hexanoic acid, ethyl rac-6-[(2-guanidino-thiazole-4-carbonyl)-amino]-3-phenyl-hexanoate, rac-6-[(2-guanidino-thiazole-4-carbonyl)-amino]-3-phenyl-hexanoic acid, ethyl rac-3-{3-[(2-guanidino-thiazole-4-carbonyl)-amino]-benzoylamino}-3-phenyl-propionate, rac-3-{3-[(2-guanidino-thiazole-4-carbonyl)-amino]-benzoylamino}-3-phenyl-propionic acid, 3-[3-[(2-guanidino-thiazole-4-carbonyl)-amino]-benzoylamino]-propionic acid trifluoroacetate, tert-butyl 3-[3-[(2-guanidino-thiazole-4-carbonyl)-amino]-benzoylamino]-propionate, (S)-N-2-{2-[(2-guanidino-thiazole-4-carbonyl)-amino]-acetyl}-aspartic acid 1-N-phenyl-amide, ethyl rac-3-[2-[(2-guanidino-thiazole-4-carbonyl)-amino]-acetylamino]-3-phenyl-propionate, rac-3-[2-[(2-guanidino-thiazole-4-carbonyl)-amino]-acetylamino]-3-phenyl-propionic acid hydrochloride, ethyl rac-3-[3-[(2-guanidino-thiazole-4-carbonyl)-amino]-propionylamino]-3-phenyl-propionate, rac-3-[3-[(2-guanidino-thiazole-4-carbonyl)-amino]-propionylamino]-3-phenyl-propionic acid, ethyl rac-3-[3-[(2-guanidino-4-methyl-thiazole-5-carbonyl)-amino]-propionylamino]-3-phenyl-propionate, rac-3-[3-[(2-guanidino-4-methyl-thiazole-5-carbonyl)-amino]-propionylamino]-3-phenyl-propionic acid,

[2-guanidino-thiazole-4-carbonyl]-Gly-Asp-Val-OH hydrochloride, ethyl 3-[2-[(2-guanidino-thiazole-4-carbonyl)-amino]-acetylamino]-propionate, 3-[2-[(2-guanidino-thiazole-4-carbonyl)-amino]-acetylamino]-propionic acid, N-[4-(2-guanidino-4-methyl-thiazol-5-yl)-phenyl]-succinamic acid monoamide, N-[3-(2-guanidino-4-methyl-thiazol-5-yl)-phenyl]-succinamic acid monoamide, rac 4-[4-(2-guanidino-4-methyl-thiazol-5-yl)-phenylcarbamoyl]-3-phenyl-butyric acid, rac 4-[3-(2-guanidino-4-methyl-thiazol-5-yl)-phenylcarbamoyl]-3-phenyl-butyric acid, methyl 5-[4-(2-guanidino-4-methyl-thiazol-5-yl)-phenylcarbamoyl]-pentanoate, methyl 5-[3-(2-guanidino-4-methyl-thiazol-5-yl)-phenylcarbamoyl]-pentanoate, 5-[4-(2-guanidino-4-methyl-thiazol-5-yl)-phenylcarbamoyl]-pentanoic acid, 5-[3-(2-guanidino-4-methyl-thiazol-5-yl)-phenylcarbamoyl]-pentanoic acid, ethyl rac 3-(4-chloro-phenyl)-4-[4-(2-guanidino-4-methyl-thiazol-5-yl)-benzoylamino]-butyrate, ethyl rac 3-(4-chloro-phenyl)-4-[3-(2-guanidino-4-methyl-thiazol-5-yl)-benzoylamino]-butyrate, ethyl rac 3-[4-(2-guanidino-4-methyl-thiazol-5-yl)-benzoylamino]-3-phenyl-propionate, ethyl rac 3-[3-(2-guanidino-4-methyl-thiazol-5-yl)-benzoylamino]-3-phenyl-propionate, rac 3-(4-chloro-phenyl)-4-[4-(2-guanidino-4-methyl-thiazol-5-yl)-benzoylamino]-butyric acid, rac 3-(4-chloro-phenyl)-4-[3-(2-guanidino-4-methyl-thiazol-5-yl)-benzoylamino]-butyric acid, rac 3-[4-(2-guanidino-4-methyl-thiazol-5-yl)-benzoylamino]-3-phenyl-propionic acid, rac 3-[3-(2-guanidino-4-methyl-thiazol-5-yl)-benzoylamino]-3-phenyl-propionic acid, ethyl rac 3-[2-[(2-guanidino-4-methyl-thiazol-5-ylcarbonyl)-amino]-acetylamino]-3-phenyl-propionate hydrochloride, ethyl rac 3-[2-[(2-guanidino-4-propyl-thiazol-5-ylcarbonyl)-amino]-acetylamino]-3-phenyl-propionate, ethyl rac 3-[2-[(2-guanidino-4-phenyl-thiazol-5-ylcarbonyl)-amino]-acetylamino]-3-phenyl-propionate, ethyl rac 3-[2-[(4-tert-butyl-2-guanidino-thiazol-5-ylcarbonyl)-amino]-acetylamino]-3-phenyl-propionate, ethyl rac 3-[2-[[2-(tert-butoxycarbonylamino-methyl)-thiazol-4-ylcarbonyl]-amino]-acetylamino]-3-phenyl-propionate, ethyl rac 3-[2-[(2-aminomethyl-thiazol-4-ylcarbonyl)-amino]-acetylamino]-3-phenyl-propionate hydrochloride, ethyl rac 3-[2-[(2-guanidinomethyl-thiazol-4-ylcarbonyl)-amino]-acetylamino]-3-phenyl-propionate hydrochloride,
rac 3-[2-[(2-guanidino-4-methyl-thiazol-5-ylcarbonyl)-amino]-acetylamino]-3-phenyl-propionic acid,
rac 3-[2-[(2-guanidino-4-propyl-thiazol-5-ylcarbonyl)-amino]-acetylamino]-3-phenyl-propionic acid,
rac 3-[2-[(2-guanidino-4-phenyl-thiazol-5-ylcarbonyl)-amino]-acetylamino]-3-phenyl-propionic acid,
rac 3-[2-[(4-tert-butyl-2-guanidino-thiazol-5-ylcarbonyl)-amino]-acetylamino]-3-phenyl-propionic acid,
rac 3-[2-[(2-aminomethyl-thiazol-4-ylcarbonyl)-amino]-acetylamino]-3-phenyl-propionic acid,
rac 3-[2-[(2-guanidinomethyl-thiazol-4-ylcarbonyl)-amino]-acetylamino]-3-phenyl-propionic acid,
ethyl rac 3-[2-[[(2-(3-benzyl-ureido)-thiazol-4-ylcarbonyl]-amino]-acetylamino]-3-phenyl-propionate,
ethyl rac 3-[3-[(4-tert-butyl-2-guanidino-thiazol-5-ylcarbonyl)-amino]-benzoylamino]-3-pyridin-3-yl-propionate,
ethyl rac 3-[3-[[4-methyl-2-(3-methyl-ureido)-thiazol-5-ylcarbonyl]-amino]-benzoylamino]-3-pyridin-3-yl-propionate,
ethyl rac 3-[2-[Cyclopropyl-(2-guanidino-4-methyl-thiazol-5-ylcarbonyl)-amino]-acetylamino]-3-phenyl-propionate hydrochloride,
tert-butyl (S)-3-[2-[(2-guanidino-4-methyl-thiazol-5-ylcarbonyl)-amino]-acetylamino]-4-oxo-4-piperidin-1-yl-butyrate,
ethyl 3-[2-[(2-guanidino-4-methyl-thiazol-5-ylcarbonyl)-amino]-acetylamino]-propionate,
rac 3-[2-[[(2-(3-benzyl-ureido)-thiazol-4-ylcarbonyl]-amino]-acetylamino]-3-phenyl-propionic acid,
rac 3-[3-[(4-tert-butyl-2-guanidino-thiazol-5-ylcarbonyl)-amino]-benzoylamino]-3-pyridin-3-yl-propionic acid,
rac 3-[3-[[4-methyl-2-(3-methyl-ureido)-thiazol-5-ylcarbonyl]-amino]-benzoylamino]-3-pyridin-3-yl-propionic acid,
rac 3-[2-[cyclopropyl-(2-guanidino-4-methyl-thiazol-5-ylcarbonyl)-amino]-acetylamino]-3-phenyl-propionic acid,
3-[2-[(2-guanidino-4-methyl-thiazol-5-ylcarbonyl)-amino]-acetylamino]-propionic acid,
(S)-3-[2-[(2-guanidino-4-methyl-thiazol-5-ylcarbonyl)-amino]-acetylamino]-4-oxo-piperidin-1-yl-butyric acid,
tert-butyl (S)-3-[2-[(2-guanidino-thiazol-4-ylcarbonyl)-amino]-acetylamino]-4-oxo-4-piperidin-1-yl-butyrate,
(S)-3-[2-[(2-guanidino-thiazol-4-ylcarbonyl)-amino]-acetylamino]-4-oxo-piperidin-1-yl-butyric acid,
ethyl rac 3-[3-[(2-guanidino-4-methyl-thiazol-5-ylcarbonyl)-amino]-phenyl-sulphonylamino]-3-phenyl-propionate,
rac 3-[3-[(2-guanidino-4-methyl-thiazol-5-ylcarbonyl)-amino]-phenylsulphonylamino]-3-phenyl-propionic acid,
rac 4-[3-(2-guanidino-thiazol-4-yl)-phenylcarbamoyl]-3-phenyl-butyric acid,
rac 3-(4-chloro-phenyl)-4-[3-(2-guanidino-thiazol-4-yl)-benzoylamino]-butyric acid,
rac 4-[3-(2-guanidino-4-methyl-thiazol-5-yl)-phenylcarbamoyl]-3-(4-methoxy-phenyl)-butyric acid,
ethyl rac-3-[5-[(2-guanidino-4-methyl-thiazole-5-carbonyl)-amino]-2-(2-methoxy-ethoxy)-benzoylamino]-3-phenyl-propionate,
rac-3-[5-[(2-guanidino-4-methyl-thiazole-5-carbonyl)-amino]-2-(2-methoxy-ethoxy)-benzoylamino]-3-phenyl-propionic acid hydrochloride,
ethyl rac-3-{3-[(2-guanidino-thiazole-5-carbonyl)-amino]-benzoylamino}-3-phenyl-propionate,
rac-3-[3-[(2-guanidino-thiazole-5-carbonyl)-amino]-benzoylamino]-3-phenyl-propionic acid,
ethyl rac-3-{3-benzyloxy-5-[(2-guanidino-4-methyl-thiazole-5-carbonyl)-amino]-benzoylamino}-3-phenyl-propionate,
rac-3-{3-benzyloxy-5-[(2-guanidino-4-methyl-thiazole-5-carbonyl)-amino]-benzoylamino}-3-phenyl-propionic acid,
ethyl rac-7-{[2-(3-benzyl-ureido)-4-methyl-thiazole-5-carbonyl]-amino}-3-phenyl-heptanoate,
rac-7-{[2-(3-benzyl-ureido)-4-methyl-thiazole-5-carbonyl]-amino}-3-phenyl-heptanoic acid,
ethyl rac-3-{3-[(2-guanidino-4-methyl-thiazole-5-carbonyl)-amino]-4-methoxy-benzoylamino}-3-phenyl-propionate,
rac-3-{3-[(2-guanidino-4-methyl-thiazole-5-carbonyl)-amino]-4-methoxy-benzoylamino}-3-phenyl-propionic acid hydrochloride,
ethyl rac-3-{2-[(2-guanidino-thiazole-4-carbonyl)-amino]-acetylamino}-3-pyridin-3-yl-propionate,
rac-3-{2-[(2-guanidino-thiazole-4-carbonyl)-amino]-acetylamino}-3-pyridin-3-yl-propionic acid,
ethyl 6-{[2-(3-benzyl-ureido)-thiazole-4-carbonyl]-amino}-5-oxo-hexanoate,
6-{[2-(3-benzyl-ureido)-thiazole-4-carbonyl]-amino}-5-oxo-hexanoic acid,
ethyl rac-7-[(2-guanidino-4-methyl-thiazole-5-carbonyl)-amino]-3-phenyl-heptanoate,
rac-7-[(2-guanidino-4-methyl-thiazole-5-carbonyl)-amino]-3-phenyl-heptanoic acid,
(S)-3-(2-{[2-(3-benzyl-ureido)-thiazole-4-carbonyl]-amino}-acetylamino)-succinic acid 4-anilide 1-tert-butyl ester,
(S)-3-(2-{[2-(3-benzyl-ureido)-thiazole-4-carbonyl]-amino}-acetylamino)-succinic acid 4-anilide,
rac 4-{3-[2-(3-benzyl-ureido)-4-methyl-thiazol-5-yl]-phenylcarbamoyl}-3-phenyl-butyric acid,
rac 4-[3-(2-guanidino-4-methyl-thiazol-5-yl)-phenylcarbamoyl]-3-pyridin-3-yl-butyrate,
rac 4-[3-(2-guanidino-4-methyl-thiazol-5-yl)-phenylcarbamoyl]-3-pyridin-3-yl-butyric acid,
rac-4-[3-(4-ethyl-2-guanidino-thiazol-5-yl)-phenylcarbamoyl]-3-phenyl-butyric acid acetate,
rac-4-[3-(2-guanidino-4-propyl-thiazol-5-yl)-phenylcarbamoyl]-3-phenyl-butyric acid,
rac-4-[3-(4-butyl-2-guanidino-thiazol-5-yl)-phenylcarbamoyl]-3-phenyl-butyric acid,
rac-4-[3-(2-guanidino-4-pentyl-thiazol-5-yl)-phenylcarbamoyl]-3-phenyl-butyric acid,
rac-3-(4-chloro-phenyl)-4-[3-(2-guanidino-4-methyl-thiazol-5-yl)-phenylcarbamoyl]-butyric acid,
rac-4-[3-(2-guanidino-4-methyl-thiazol-5-yl)-phenylcarbamoyl]-3-hydroxy-butyric acid,
4-[3-(2-guanidino-4-methyl-thiazol-5-yl)-phenylcarbamoyl]-butyric acid,
rac-4-[3-(2-guanidino-4-methyl-thiazol-5-yl)-phenylcarbamoyl]-3-methyl-butyric acid,
rac-3-(3-bromo-phenyl)-4-[3-(2-guanidino-4-methyl-thiazol-5-yl)-phenylcarbamoyl]-butyric acid,
rac-3-(3,5-dichloro-2-hydroxy-phenyl)-4-[3-(2-guanidino-4-methyl-thiazol-5-yl)-phenylcarbamoyl]-butyric acid, rac-4-[3-(2-guanidino-4-methyl-thiazol-5-yl)-phenylcarbamoyl]-3-(3-methoxy-phenyl)-butyric acid,
rac-4-[4-chloro-3-(2-guanidino-4-methyl-thiazol-5-yl)-phenylcarbamoyl]-3-phenyl-butyric acid,
rac-4-[2-chloro-5-(2-guanidino-4-methyl-thiazol-5-yl)-phenylcarbamoyl]-3-phenyl-butyric acid
(S)-2-butylsulphonylamino-4-[3-(2-guanidino-4-methyl-thiazol-5-yl)-benzoylamino]-butyric acid hydrochloride,
ethyl rac-3-[3-[3-(2-guanidino-4-methyl-thiazol-5-yl)-phenyl]-ureido]-3-phenyl-propionate,
rac-3-[3-[3-(2-guanidino-4-methyl-thiazol-5-yl)-phenyl]-ureido]-3-phenyl-propionic acid,
ethyl rac-4-[3-(2-guanidino-4-methyl-thiazol-5-yl)-phenylcarbamoyl]-3-phenyl-butyrate hydrochloride,
rac-4-[[3-(2-guanidino-4-methyl-thiazol-5-yl)-phenyl]-methyl-carbamoyl]-3-phenyl-butyric acid,
methyl rac-4-benzyloxycarbonylamino-4-[3-(2-guanidino-4-methyl-thiazol-5-yl)-phenylcarbamoyl]-butyrate,
rac-4-benzyloxycarbonylamino-4-[3-(2-guanidino-4-methyl-thiazol-5-yl)-phenyl-carbamoyl]-butyric acid,
methyl rac-5-[3-(4-carboxy-3-phenyl-butyrylamino)-phenyl]-2-guanidino-thiazole-4-carboxylate,
rac-5-[3-(4-carboxy-3-phenyl-butyrylamino)-phenyl]-2-guanidino-thiazole-4-carboxylic acid,
ethyl rac-3-[2-[(2-guanidino-5-methyl-thiazol-4-ylcarbonyl)-amino]-acetylamino]-3-phenyl-propionate,
ethyl rac-3-[2-[(5-tert-butyl-2-guanidino-thiazol-4-ylcarbonyl)-amino]-acetylamino]-3-phenyl-propionate,
ethyl rac-3-[2-[(2-guanidino-5-phenyl-thiazol-4-ylcarbonyl)-amino]-acetylamino]-3-phenyl-propionate,
ethyl rac-3-[2-[[2-guanidino-5-(3-nitro-phenyl)-thiazol-4-ylcarbonyl]-amino]-acetyl-amino]-3-phenyl-propionate,
rac-3-[2-[(2-guanidino-5-methyl-thiazol-4-ylcarbonyl)-amino]-acetylamino]-3-phenyl-propionic acid,
rac-3-[2-[(5-tert-butyl-2-guanidino-thiazol-4-ylcarbonyl)-amino]-acetylamino]-3-phenyl-propionic acid,
rac-3-[2-[(2-guanidino-5-phenyl-thiazol-4-ylcarbonyl)-amino]-acetylamino}-3-phenyl-propionic acid,
rac-3-[2-[2-guanidino-5-(3-nitro-phenyl)-thiazol-4-ylcarbonyl]-amino]-acetylamino]-3-phenyl-propionic acid,
rac-3-[2-[[5-(3-amino-phenyl)-2-guanidino-thiazol-4-ylcarbonyl]-amino]-acetyl-amino]-3-phenyl-propionic acid,
ethyl rac-3-[2-[[2-(3-benzyl-ureido)-5-methyl-thiazol-4-ylcarbonyl]-amino]-acetylamino]-3-phenyl-propionate,
ethyl rac-3-[2-[[2-(3-benzyl-ureido)-5-phenyl-thiazol-4-ylcarbonyl]-amino]-acetylamino]-3-phenyl-propionate,
rac-3-[2-[[2-(3-benzyl-ureido)-5-methyl-thiazol-4-ylcarbonyl]-amino]-acetylamino]-3-phenyl-propionic acid,
rac-3-[2-[[2-(3-benzyl-ureido)-5-phenyl-thiazol-4-ylcarbonyl]-amino]-acetylamino]-3-phenyl-propionic acid,
rac-4-[3-[2-(3-benzyl-ureido)-5-methyl-thiazol-4-yl]-phenylcarbamoyl]-3-phenyl-butyric acid,
rac-4-[[3-[2-(3-benzyl-ureido)-5-methyl-thiazol-4-yl]-phenyl]-methyl-carbamoyl]-3-phenyl-butyric acid,
ethyl rac-3-phenyl-3-[2-[[2-(3-phenyl-ureido)-thiazol-4-ylcarbonyl]-amino]-acetyl-amino]-propionate,
ethyl rac-3-[2-[[2-(3-Phenethyl-ureido)-thiazol-4-ylcarbonyl]-amino-acetylamino]-3-phenyl-propionate,
ethyl rac-3-(2-[[2-(3-butyl-ureido)-thiazol-4-ylcarbonyl]-amino]-acetylamino)-3-phenyl-propionate,
rac-3-phenyl-3-[2-[[2-(3-phenyl-ureido)-thiazol-4-ylcarbonyl]-amino]-acetylamino]-propionic acid,
rac-3-[2-[[2-(3-Phenethyl-ureido)-thiazol-4-ylcarbonyl]-amino]-acetylamino]-3-phenyl-propionic acid,
rac-3-(2-[[2-(3-butyl-ureido)-thiazol-4-ylcarbonyl]-amino]-acetylamino)-3-phenyl-propionic acid,
ethyl rac-3-[4-[[2-(3-benzyl-ureido)-thiazol-4-ylcarbonyl]-amino]-phenyl]-3-tert-butoxycarbonylamino-propionate,
rac-3-[4-[[2-(3-benzyl-ureido)-thiazol-4-ylcarbonyl]-amino]-phenyl]-3-tert-carbonylamino-propionic acid,
rac-3-amino-3-[4-[[2-(3-benzyl-ureido)-thiazol-4-ylcarbonyl]-amino]-phenyl]-propionic acid,
ethyl rac-3-[4-[[2-(3-benzyl-ureido)-thiazol-4-ylcarbonyl]-amino]-phenyl]-3-propionyl-amino-propionate,
ethyl rac-3-[4-[[2-(3-benzyl-ureido)-thiazol-4-ylcarbonyl]-amino]-phenyl]-3-butyl-sulphonylamino-propionate,
rac-3-[4-[[2-(3-benzyl-ureido)-thiazol-4-ylcarbonyl]-amino]-phenyl]-3-propionyl-amino-propionic acid,
rac-3-[4-[[2-(3-benzyl-ureido)-thiazol-4-ylcarbonyl]-amino]-phenyl]-3-butylsulphonyl-amino-propionic acid,
diethyl 3-[4-[[2-(3-benzyl-ureido)-thiazol-4-ylcarbonyl]-amino]-phenyl]-glutarate,
3-[4-[[2-(3-benzyl-ureido)-thiazol-4-ylcarbonyl]-amino]-phenyl]-glutaric acid,
rac-4-[3-[2-(N'-benzyl-guanidino)-4-methyl-thiazol-5-yl]-phenylcarbamoyl]-3-phenyl-butyric acid,
ethyl rac-3-phenyl-3-[2-[[2-(pyridin-2-ylamino)-thiazol-4-ylcarbonyl]-amino]-acetyl-amino]-propionate,
rac-3-phenyl-3-[2-[[2-(pyridin-2-ylamino)-thiazol-4-ylcarbonyl]-amino]-acetylamino]-propionic acid,
ethyl rac-3-[2-[[2-(3-benzyl-ureido)-thiazole-4-carbonyl]-amino]-acetylamino]-3-pyridin-3-yl-propionate,
rac-3-[2-[[2-(3-benzyl-ureido)-thiazole-4-carbonyl]-amino]-acetylamino]-3-pyridin-3-yl-propionic acid acetate,
tert-butyl (S)-N-benzyl-3-[2-[[2-(3-benzyl-ureido)-thiazole-4-carbonyl]-amino]-acetylamino]-succinamate,
ethyl 3-[2-[[2-(3-benzyl-ureido)-thiazole-4-carbonyl]-amino]-acetylamino]-propionic acid hydrochloride,
tert-butyl (S)-3-[2-[[2-(3-benzyl-ureido)-thiazole-4-carbonyl]-amino]-acetylamino]-N-(3-methoxy-phenyl)-succinamate,
(S)-3-[2-[[2-(3-benzyl-ureido)-thiazole-4-carbonyl]-amino]-acetylamino]-N-(3-methoxy-phenyl)-succinamic acid,
tert-butyl (S)-2-[2-[2-[[2-(3-benzyl-ureido)-thiazole-4-carbonyl]-amino]-acetylamino]-3-tert-butoxycarbonyl-propionylamino]-benzoate,
(S)-2-[2-(2-{[2-(3-benzyl-ureido)-thiazole-4-carbonyl]-amino}-acetylamino)-3-carboxy-propionylamino]-benzoic acid,
methyl 6-{[2-(3-benzyl-ureido)-thiazole-4-carbonyl]-amino}-hexanoate, 6-{[2-(3-benzyl-ureido)-thiazole-4-carbonyl]-amino}-hexanoic acid, tert-butyl (S)-3-[3-[(2-guanidino-4-methyl-thiazole-5-carbonyl)-amino]-benzoyl-amino]-N-phenyl-succinamate, (S)-3-[3-[(2-guanidino-4-methyl-thiazole-5-carbonyl)-amino]-benzoylamino]-N-phenyl-succinamic acid trifluoroacetate, tert-butyl (S)-2-[(S)-2-[2-[[2-(3-benzyl-ureido)-thiazole-4-carbonyl]-amino]-acetyl-amino]-3-tert-butoxycarbonyl-propionylamino]-3-methyl-butyrate, tert-butyl (S)-3-[(S)-2-[[2-(3-benzyl-ureido)-thiazole-4-carbonyl]-amino]-acetyl-amino]-N-(tert-butoxycarbonyl-phenyl-methyl)-succinamate, (S)-3-[2-[[2-(3-benzyl-ureido)-thiazole-4-carbonyl]-amino]-acetylamino]-N-[(S)-carboxy-phenyl-methyl)-succinamic acid acetate/trifluoroacetate, methyl (S)-6-{[2-(3-benzyl-ureido)-thiazole-4-carbonyl]-amino}-2-tert-butoxycarbonyl-amino-hexanoate, (S)-6-{[2-(3-benzyl-ureido)-thiazole-4-carbonyl]-amino}-2-tert-butoxycarbonylamino-hexanoic acid, ethyl rac-3-benzylcarbamoyl-6-{[2-(3-benzyl-ureido)-thiazole-4-carbonyl]-amino}-hexanoate, rac-3-benzylcarbamoyl-6-{[2-(3-benzyl-ureido)-thiazole-4-carbonyl]-amino}-hexanoic acid, ethyl 5-oxo-6-{[2-(3-pyridin-2-ylmethyl-ureido)-thiazole-4-carbonyl]-amino}-hexnoate, 5-oxo-6-{[2-(3-pyridin-2-ylmethyl-ureido)-thiazole-4-carbonyl]-amino}-hexanoic acid hydrochloride, tert-butyl (S)-N-benzyl-3-{4-[2-(3-benzyl-ureido)-thiazol-4-yl]-butyrylamino}-succinamate, (S)-N-benzyl-3-{4-[2-(3-benzyl-ureido)-thiazol-4-yl]-butyrylamino}-succinamic acid trifluoroacetate, ethyl 3-[4-[[2-(3-benzyl-ureido)-thiazole-4-carbonyl]-amino]-phenyl]-propionate, 3-[4-[[2-(3-benzyl-ureido)-thiazole-4-carbonyl]-amino]-phenyl]-propionic acid, diethyl rac-2-[3-[[2-(3-benzyl-ureido)-thiazole-4-carbonyl]-amino]-2-oxo-propyl]-succinate, rac-2-[3-[[2-(3-benzyl-ureido)-thiazole-4-carbonyl]-amino]-2-oxo-propyl]-succinic acid, di-tert-butyl (S)-2-(2-{[2-(3-benzyl-ureido)-thiazole-4-carbonyl]-amino}-acetylamino)-succinate, (S)-2-(2-{[2-(3-benzyl-ureido)-thiazole-4-carbonyl]-amino}-acetylamino)-succinic acid trifluoroacetate, tert-butyl (S)-3-[2-[[2-(3-benzyl-ureido)-thiazole-4-carbonyl]-amino]-acetylamino]-N-isobutyl-succinamate, tert-butyl (S)-3-[2-[[2-(3-benzyl-ureido)-thiazole-4-carbonyl]-amino]-acetylamino]-N-pyridin-2-ylmethyl-succinamate, tert-butyl (S)-3-[2-[[2-(3-benzyl-ureido)-thiazole-4-carbonyl]-amino]-acetylamino]-N-pyridin-3-ylmethyl-succinamate, (S)-3-[2-[[2-(3-benzyl-ureido)-thiazole-4-carbonyl]-amino]-acetylamino]-N-pyridin-3-ylmethyl-succinamic acid trifluoroacetate, (S)-3-[4-[[2-(3-benzyl-ureido)-thiazole-4-carbonyl]-amino]-phenyl]-2-tert-butoxy-carbonylamino-propionic acid, (R)-3-[4-[[2-(3-benzyl-ureido)-thiazole-4-carbonyl]-amino]-phenyl]-2-tert-butoxy-carbonylamino-propionic acid, tert-butyl (S)-N-pyridin-2-ylmethyl-3-(2-{[2-(3-pyridin-2-ylmethyl-ureido)-thiazole-4-carbonyl]-amino}-acetylamino)-succinamate, (S)-N-pyridin-2-ylmethyl-3-(2-{[2-(3-pyridin-2-ylmethyl-ureido)-thiazole-4-carbonyl]-amino}-acetylamino)-succinamic acid, tert-butyl 3-(3-{[2-(3-benzyl-ureido)-thiazole-4-carbonyl]-amino}-benzoylamino)-propionate, 3-(3-{[2-(3-benzyl-ureido)-thiazole-4-carbonyl]-amino}-benzoylamino)-propionic acid, ethyl rac-3-(2-{[2-(imidazolidin-2-ylideneamino)-thiazole-4-carbonyl]-amino}-acetyl-amino)-3-pyridin-3-yl-propionate, 3-(2-{[2-(imidazolidin-2-ylideneamino)-thiazole-4-carbonyl]-amino}-acetylamino)-3-pyridin-3-yl-propionic acid hydrochloride, ethyl rac-7-[[4-methyl-2-(tetrahydro-pyrimidin-2-ylideneamino)-thiazole-5-carbonyl]-amino]-3-phenyl-heptanoate and prac-7-[[4-methyl-2-(tetrahydro-pyrimidin-2-ylideneamino)-thiazole-5-carbonyl]-amino]-3-phenyl-heptanoic acid hydrochloride acetate.

Examples of especially preferred compounds of formula I are:

rac 3-[2-[[(2-(3-Benzyl-ureido)-thiazol-4-ylcarbonyl]-amino]-acetylamino]-3-phenyl-propionic acid, rac 4-[3-(2-guanidino-4-methyl-thiazol-5-yl)-phenylcarbamoyl]-3-phenyl-butyric acid, rac 3-[2-[(2-guanidinomethyl-thiazol-4-ylcarbonyl)-amino]-acetylamino]-3-phenyl-propionic acid, rac 3-[3-[(2-guanidino-4-methyl-thiazol-5-ylcarbonyl)-amino]-phenylsulphonyl-amino]-3-phenyl-propionic acid, rac 3-[3-[(2-guanidino-4-methyl-thiazole-5-carbonyl)-amino]-benzoylamino]-3-phenyl-propionic acid hydrochloride, rac 3-[3-[(4-tert-butyl-2-guanidino-thiazol-5-ylcarbonyl)-amino]-benzoylamino]-3-pyridin-3-yl-propionic acid,

[2-guanidino-thiazole-4-carbonyl]-Gly-Asp-Val-OH hydrochloride, rac 3-(4-chloro-phenyl)-4-[3-(2-guanidino-4-methyl-thiazol-5-yl)-benzoylamino]-butyric acid, rac-3-[3-[(2-guanidino-4-methyl-thiazole-5-carbonyl)-amino]-propionylamino]-3-phenyl-propionic acid, rac 4-[3-(2-guanidino-4-methyl-thiazol-5-yl)-phenylcarbamoyl]-3-(4-methoxy-phenyl)-butyric acid, rac 4-[3-(2-guanidino-4-methyl-thiazol-5-yl)-phenylcarbamoyl]-3-pyridin-3-yl-butyric acid, 6-{[2-(3-benzyl-ureido)-thiazole-4-carbonyl]-amino}-5-oxo-hexanoic acid, (S)-3-(2-{[2-(3-benzyl-ureido)-thiazole-4-carbonyl]-amino}-acetylamino)-succinic acid 4-anilide, (S)-N-benzyl-3-[2-[[2-(3-benzyl-ureido)-thiazole-4-carbonyl]-amino]-acetylamino]-succinamic acid trifluoroacetate, (S)-2-[(S)-2-(2-{[2-(3-benzyl-ureido)-thiazole-4-carbonyl-amino}-acetylamino)-3-carboxy-propionylamino]-3-methyl-butyric acid acetate/trifluoroacetate, (S)-3-[2-[[2-(3-benzyl-ureido)-thiazole-4-carbonyl]-amino]-acetylamino]-N-isobutyl-succinamic acid trifluoroacetate and (S)-3-[2-[[2-(3-benzyl-ureido)-thiazole-4-carbonyl]-amino]-acetylamino]-N-pyridin-2-ylmethyl-succinamic acid trifluoroacetate.

Processes for the manufacture of compounds of formula of I are an object of the invention. The processes are preferably based on the reaction of a thiazole derivative, which represents the thiazole base member, with a reactive reagent, which represents the substituent $R^2$ or a reactive part and/or derivative thereof.

The following routes can be set out, for example, for the preparation of the corresponding thiazole base member, with the substituents and indices used in the following Schemes having the significances given above unless indicated to the contrary.

Suitable thiazole base members can be prepared, for example, by the method presented in Scheme 1a. In this, an α-bromo-ketone of formula VII, such as ethyl pyruvate, is reacted in a solvent, such as ethanol, with a thiourea derivative of formula VIII, such as 2-imino-4-thiobiuret, at elevated temperature [J. Med. Chem., 34: 914 (1991)]. A subsequent saponification of the ester group by means of a base, such as aqueous NaOH or KOH, yields a thiazole-4-carboxylic acid of type X (Scheme 1a).

In a process variant an optionally substituted thiourea of formula IX is used and, after cyclization to the thiazole, is reacted with an isocyanate, such as benzyl isocyanate, in a solvent, such as DMF, at room temperature, followed by a saponification of the ester as described above.

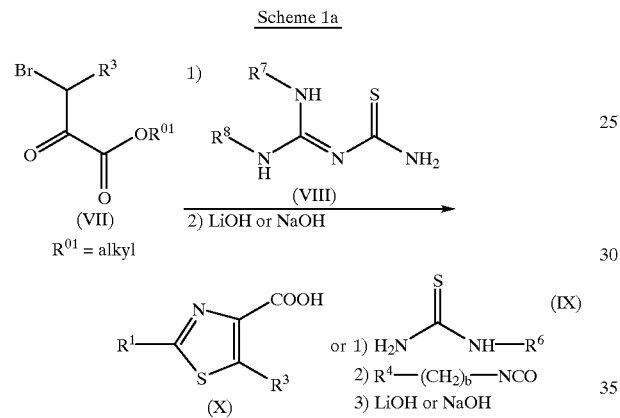

α-Halo-ketones are used in a further preparative process (Scheme 1b), which analogously to the process described yields thiazole-5-carboxylic acid derivatives of type XIII [Farmaco, 44: 1011 (1989)]. The α-halo-ketones of formula XII are prepared from the corresponding β-keto esters (formula XI), such as ethyl butyrylacetate, ethyl pivaloylacetate, etc., by halogenation with e.g. bromine in a solvent, such as water, conveniently at a temperature of 0–5° C. (J. Chem. Soc .Perkin I 1982, 162).

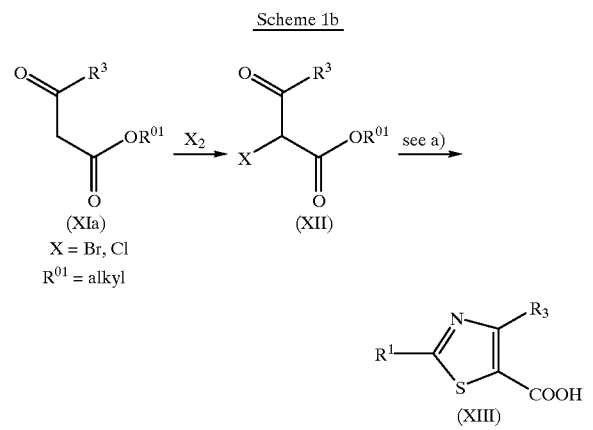

In another variant (Scheme 1c) the thiazole base member is synthezised by reaction of a N-protected amino acid thioamide optionally substituted on the amino nitrogen, such as N-Boc-glycine thioamide, with an α-halo-ketone of formula VII or XIb. A subsequent saponification of the ester group by means of a base, as described under Scheme 1a, yields thiazolecarboxylic acid derivatives of formula XIV. After removal of the protecting group these can be modified further in accordance with Scheme 10.

When a residue $((CH_2)_e$—NH-(protecting group) is used in place of the $COOR^{01}$ residue in compound XIb or XII, then amino-thiazole derivatives corresponding to XIII can be obtained. The analogous situation also applies to Scheme 1a.

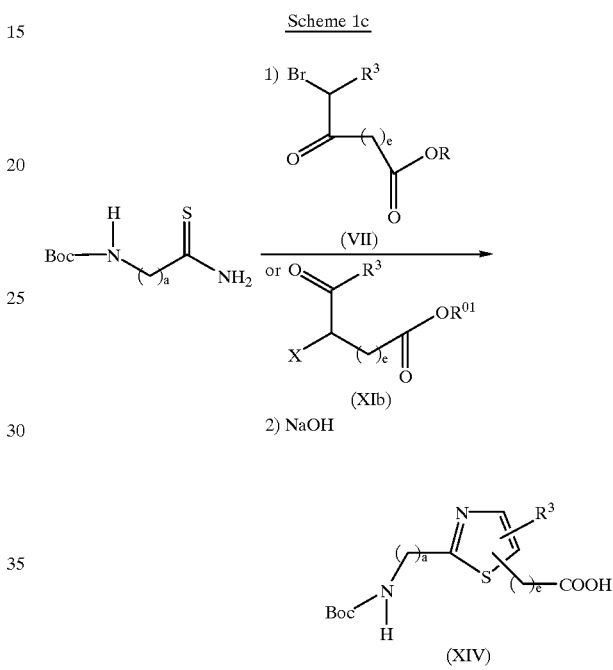

In an additional process variant (Scheme 1d) a substituted benzaldehyde, such as 3-nitrobenzaldehyde, or methyl 3-formyl-benzoate, is converted with a nitroalkane, such as nitroethane, in a suitable solvent, such as acetic acid, with the addition of ammonium acetate, conveniently at elevated temperature, such as reflux temperature, into the corresponding nitro-olefin (Org. Synth. Coll. IV, 573 or Synthesis 1994, 258). This is epoxidized by means of an oxidation agent, such as hydrogen peroxide, in a suitable solvent, such as water, with the addition of aqueous sodium hydroxide solution to give a nitroepoxide of formula XV (Synthesis 1976, 53). The reaction of such nitroepoxide with a thiourea derivative, such as 2-imino-4-thiobiuret, at elevated temperature, such as the reflux temperature, yields arylthiazoles of formula XVI.

By the use of an alternative thiourea derivative in the above reaction and subsequently reaction with an isocyanate, such as benzyl isocyanate, in a solvent, such as DMF, at room temperature there are obtained arylthiazoles of formula XVII, into which subsequently an additional substituent $R^5$ can be introduced by usual methods.

Scheme 1d

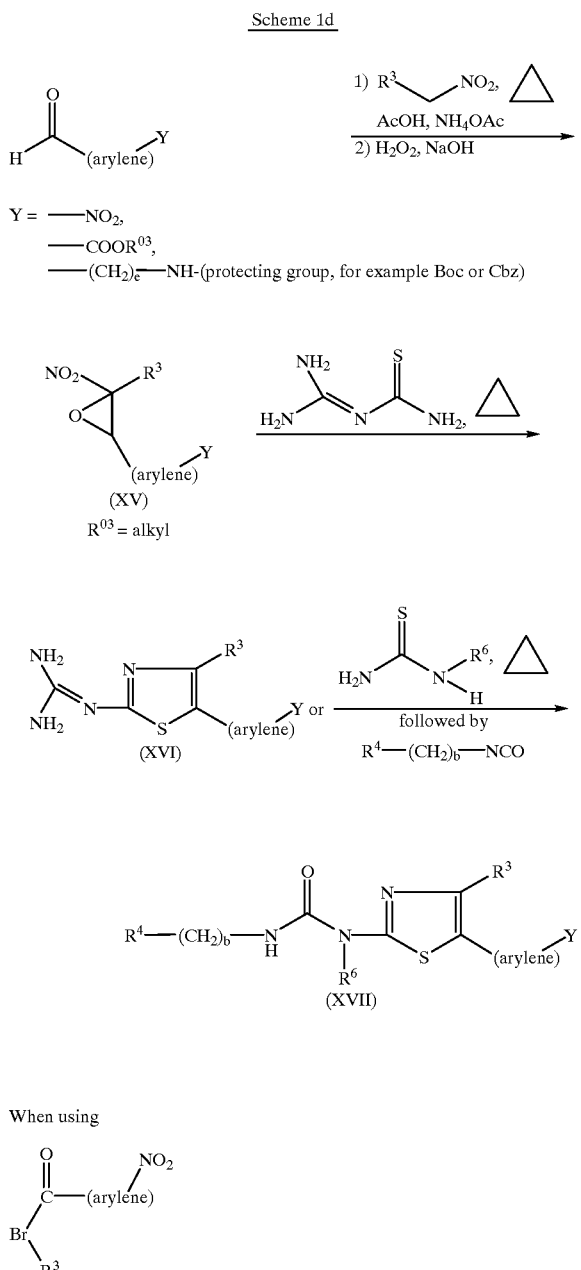

in place of compound XV in Scheme 1d there is obtained the compound corresponding to XVI and XVII in which, however, the arylene residue is bonded to position 4 of the thiazole and R³ is bonded to position 5 of the thiazole ring.

In order to prepare compounds analogous to XVI to XVII, with e being other than zero in accordance with formula (I), in place of the thiourea derivative used in Scheme 1d there can be used, for example, the thioamide used as the starting material in Scheme 1c.

The thiazole base members obtainable in accordance with the above processes are converted in a subsequent reaction with reactive components and/or reactive derivatives of the R² substituent to give a compound of general formula I in one or more reaction steps.

In the cases where c is equal to 1, i.e. an amide bond is present on the thiazole structure, a corresponding thiazole-carboxylic acid can be reacted with a corresponding amine to give a compound of formula I according to known methods. In principle, the following route can be set out:

In the following process variant (Scheme 2) by coupling a thiazolecarboxylic acid of formula XXXI with an amine of formula XXXVII using BOP, HBTU or CDMT and with subsequent hydrolysis of the ester function there is prepared the desired thiazole I in this connection, see also Z. J. Kaminski, Synthesis, 1987, 917.

Scheme 2

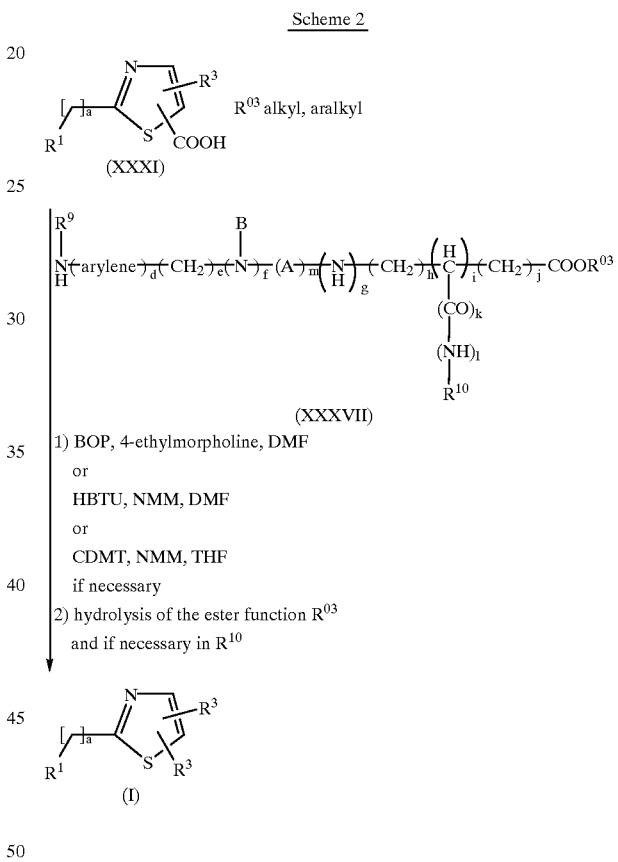

For example, when f equals zero and g equals 1 the following process can be used for the manufacture of compounds of formula I:

A thiazolecarboxylic acid of formula XXXI (Scheme 3) is coupled with a amine of formula XXXII by means of a usual coupling reagent, such as HBTU CDMT, etc., in the presence of a base, such as N-methylmorpholine, in a solvent, such as DMF or THF. A subsequent hydrolysis by means of a strong base, such as NaOH in a solvent, such as water-ethanol, yields the thiazole acid XXXIV. This is reacted with amine XXXV in a further coupling using HBTU or CDMT and subsequently hydrolyzed to XXXVI by ester cleavage using strong acid, such as trifluoroacetic acid in methylene chloride or aqueous hydrochloric acid, or using a strong base, such as NaOH.

Scheme 3

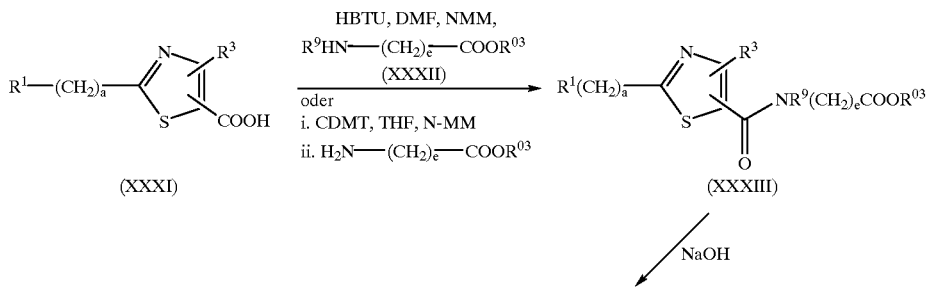

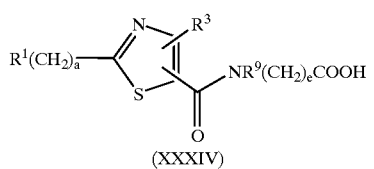

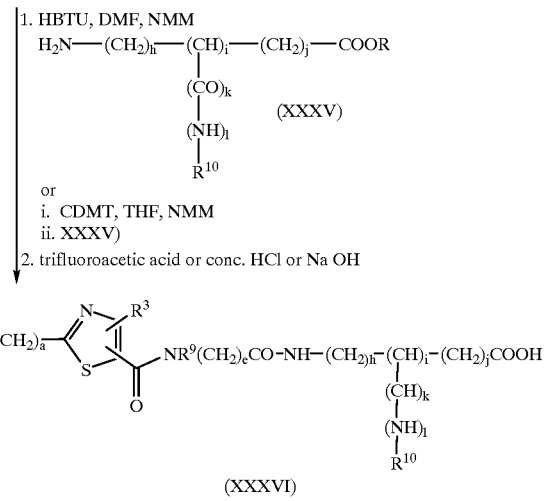

$R^{03}$ = alkyl, aralkyl

The preparation of the corresponding amine components is effected according to methods known per se. When g and f in general formula I are not equal, the amide or sulphonamide bonding which then occurs can be achieved, for example, by reaction of the corresponding amine component with an acid component according to known methods.

The following process can be used e.g. for the preparation of the amine component:

N-Protected amino acids XXI are (Scheme 4) coupled with an amino acid ester XXII by means of a coupling reagent, such as CDMT, in the presence of a base, such as N-methylmorpholine, in a suitable solvent, such as THF. N-Protecting groups, such as BOC, are then cleaved off with HCl in ethyl acetate or with trifluoroacetic acid and those such as Cbz are cleaved off by catalytic hydrogenation, e.g. on Pd/C in a solvent, such as ethanol, to give compounds of type XXIII.

Scheme 4

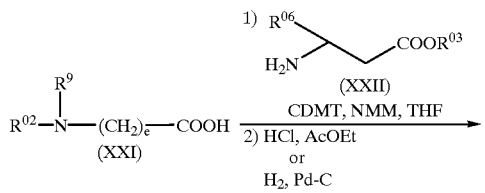

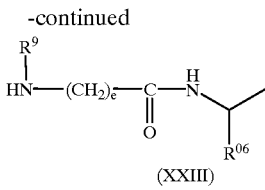

(XXIII)

$R^{02}$ = Boc, Cbz
$R^{03}$ = alkyl, aralkyl
$R^{06}$ = H, aryl, heteroaryl

For example, other amine components (formula XXV; Scheme 5a) can be prepared by coupling an optionally substituted, N-protected aminobenzoic acid XXIV with an amino acid ester XXII using a coupling reagent, such as CDMT or BOP, in the presence of a base, such as NMM or N-ethyl-morpholine, in a suitable solvent, such as DMF or THF, at RT or, if necessary, elevated temperature and subsequently removing the protecting groups as described in Scheme 4.

Scheme 5a

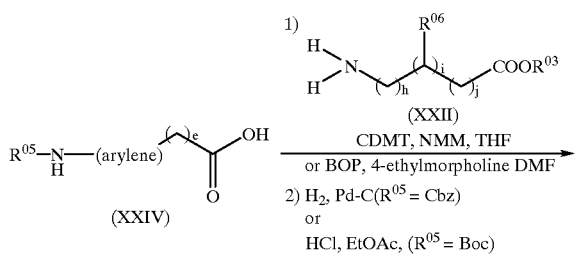

$R^{03}$ = alkyl, aralkyl
$R^{05}$ = Boc, Cbz
$R^{06}$ = ——$(CO)_k$——$(NH)_l$——$R^{10}$ Further amino components can be prepared e.g. as follows: Nitrosulphochlorides are reacted (Scheme 5b) with an amine component XXII in the presence of the strong base, such as aqueous NaOH, in a solvent, such as ether. Esterification of the free carboxylic acids followed by a reduction of the nitro group according to usual methods, such as hydrogen in the presence Raney-nickel as the catalyst, yields the anilino-esters XXVI.

Scheme 5b

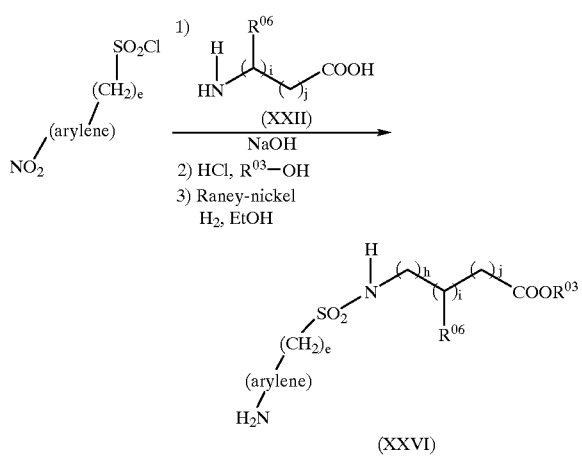

$R^{03}$ = alkyl, aralkyl
$R^{06}$ = ——$(CO)_k$——$(NH)_l$——$R^{10}$

Further amine components can be prepared, for example, as follows: Intermediates XXX (Scheme 6a) are prepared by coupling an appropriate aspartic acid derivative, such as XXIX, with an amine HNRR' using the methods already described.

Scheme 6a

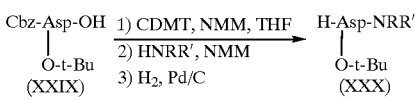

R = H, alkyl
R' = aryl, heteroaryl
or R and R' together with the N atom form a ring Compounds of formula XXXXII can be prepared as further intermediates. For this, amine components of formula XXXXI, the carboxylic acid function of which is protected suitably as an ester, are reacted with an acid chloride, such as phosgene or sulphuryl chloride, in the presence of a base, such as e.g. 4-ethylmorpholine, and in a suitable solvent, such as e.g. toluene.

Scheme 6b

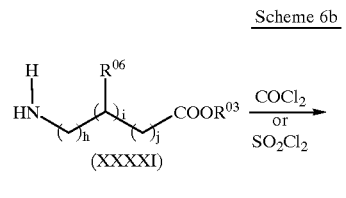

$R^{06}$ = ——$(CO)_k$——$(NH)_l$——$R^{10}$

When f and g of general formula both equal zero, then the corresponding compound (A is —C(O)—) can be obtained according to known methods for the preparation of ketones [such as e.g. *Biochem. Med.*, 17: 31–44 (1977)].

When A equals $SO_2$, the corresponding sulphones are obtained by oxidation of the thioethers, which are prepared according to known methods, e.g. by reaction of a thiazole with the corresponding alkyl halide.

When f and g are both equal to 1, the compounds are corresponding ureas or sulphamides. The manufacture is effected when c is equal to zero by reaction of the compound XXXXII with the compounds e.g. of formula XVI and XVII reduced to the amine. When c is equal to 1, the acid chloride of formula XXXXII is reacted with a corresponding mono-protected diamine, which after cleavage of the protecting group is reacted with the thiazolecarboxylic acid of formula XXXI. Boc or Cbz comes into consideration, for example, as the protecting group. When d is equal to 1, i.e. arylene is present, then a corresponding diamine in which the arylene is already present is used.

Alternatively, the above compounds of general formula I can also be obtained by reaction of a reactive fragment of the amine described in Scheme 2 and subsequent addition of the still missing substituent part of $R^2$.

When the compounds of formula I are substances in which c is equal to zero, then it is possible to proceed analogously to Scheme 2 with the formation of an amide bond. When f is equal to 1 and g is equal to zero or f is equal to zero and g is equal to 1, the corresponding compound of formula I can be manufactured by reaction of an amino aryl thiazole with an acid derivative (f equals 1 and g equals zero).

For example, the following methods can be used:

Reduction of the nitro-arylthiazoles of formula XVI (Scheme 7a) with a suitable reducing agent, such as hydrogen in the presence of a suitable catalyst, such as Raney-nickel, in a solvent, such as aqueous hydrochloric acid-methanol, or as an alternative, tin-II chloride in aqueous hydrochloric acid, preferably at elevated temperatures, such as 50° C., yields the corresponding aniline derivative. This is reacted with a carboxylic acid anhydride, such as succinic acid anhydride, glutaric acid anhydride etc., in the presence of a base, such as 4-ethylmorpholine, in a solvent, such as DMF, at room temperature and yields a guanidino-arylthiazole of formula XVIII.

In a process variant the aniline derivative obtained after the reduction is reacted with a dicarboxylic acid protected as the mono-ester, such as mono-methyl adipate, under the influence of a coupling reagent, such as BOP, and a base, such as 4-ethylmorpholine, in a solvent, such as DMF, at room temperature, followed by an ester hydrolysis by means of a strong base, such as lithium hydroxide, in a suitable solvent, such as water-tetrahydrofuran, preferably at room temperature.

When Y is equal to —$(CH_2)_e$—NH-(protecting group), then no reduction is required. The corresponding protecting group, for example Boc or Cbz, can be removed using usual methods (e.g. HCl in ethyl acetate).

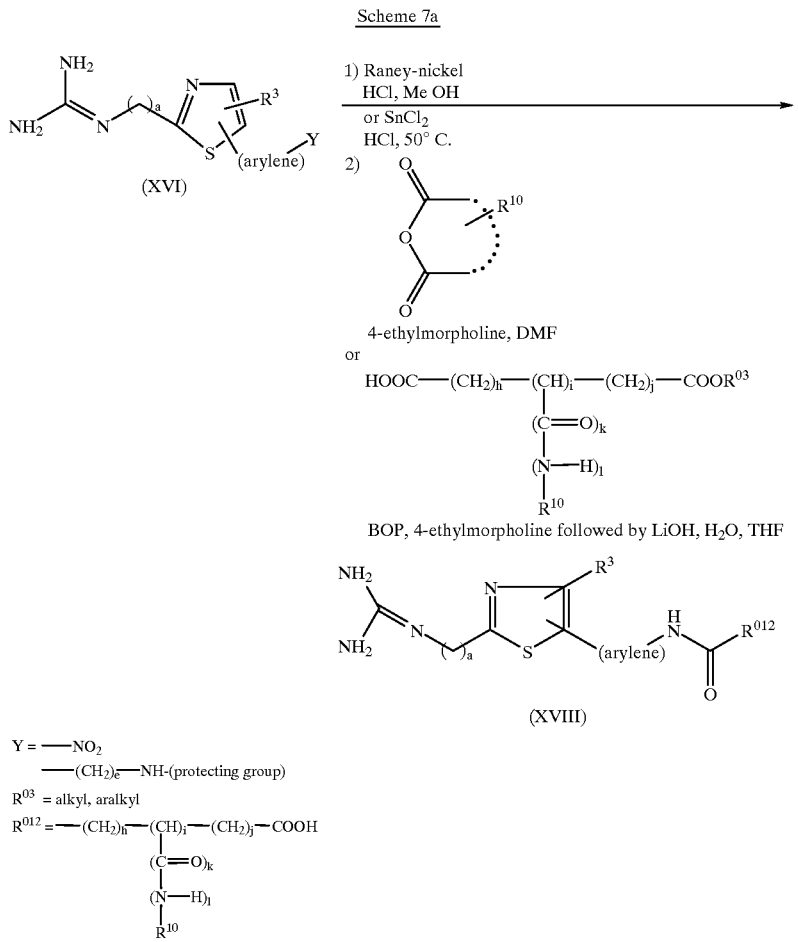

In a manner analogous to Scheme 7a, nitro-arylthiazoles of formula XVII are converted into the corresponding ureido-aryl-thiazoles of formula XIX (Scheme 7b).

Also analogously to Scheme 7a, the corresponding 4-(nitro-aryl)-2-ureido-thiazoles are reduce and acylated. Also here in the case where Y is equal to —$(CH_2)_e$—NH-(protecting group) no reduction is required. When B is other than hydrogen, the corresponding amines, as described for Scheme 7a, are alkylated prior to the acylation with an aldehyde in the presence of $NaBH_4$ or $NaCNBH_3$.

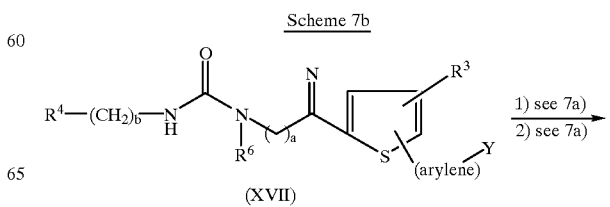

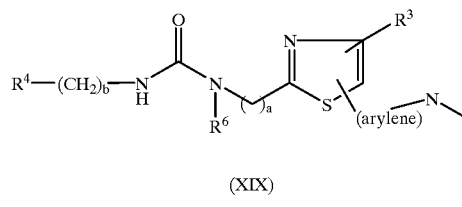

(XIX)

Y = —NO$_2$
—(CH$_2$)$_e$—NH-(protecting group)
R$^{012}$ = —(CH$_2$)$_h$—(CH)$_i$—(CH$_2$)$_j$—COOH
            |
          (C=O)$_k$
            |
          (N—H)$_l$
            |
          R$^{10}$ Also, compounds of the type

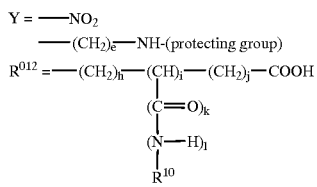

can be used analogously to Schemes 7a and 7b, although in this case the amino group must be protected with e.g. Boc or Cbz.

When f is equal to zero and g is equal to 1, the corresponding compounds of formula I can be obtained by reaction of a thiazole acid derivative with an amine:

The carboxylic esters of the arylthiazoles of formula XVI and XVII (Scheme 1d) are hydrolyzed by means of a strong base, such as lithium hydroxide, in a suitable solvent, such as water-tetrahydrofuran, preferably at room temperature (Scheme 8). Coupling of the acids with an amine component, the carboxylic acid function of which is suitably protected as an ester, using a coupling reagent, such as BOP and a base, such as 4-ethylmorpholine, in a solvent, such DMF, at room temperature, followed by an ester hydrolysis using a strong base, such as lithium hydroxide, in a suitable solvent, such as water-tetrahydrofuran, preferably at room temperature, yields the guanidino-aryl-thiazoles of formula XX. When R$^1$ is amino, this must be present as Boc- or Cbz-protected amino.

The carboxylic acid esters of the 2-ureido-aryl thiazoles of formula XVII are coupled and saponified in a manner analogous to Scheme 8. The corresponding 4-(hydroxycarbonylaryl)-thiazoles are reacted analogously.

Scheme 8

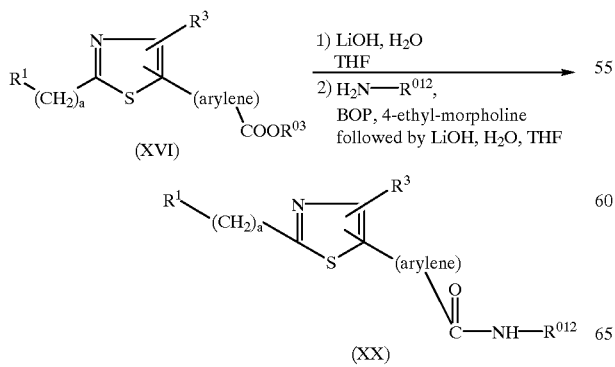

R$^{03}$ = alkyl, aralkyl

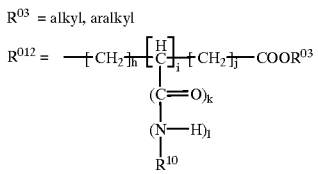

The corresponding aminoarylthiazoles and carboxyarylthiazoles are accessible e.g. by the reaction route set forth in Scheme 1d. The amine derivatives (g equals 1) or acid derivatives (f equals 1) required for the generation of the substituent R$^2$ are obtainable according to methods known per se.

Compounds of the formula H$_2$N—R$^{012}$ are commercially available or can be synthesized according to, for example, one of the following routes: when R$^{10}$ is an amino acid bonded via the amino group and k is equal to 1 and l is equal to zero, the synthesis is effected according to usual methods and protecting group techniques as used in peptide synthesis. When R$^{10}$ is aryl, aralkyl, heterocyclyl, heterocyclylalkyl, hydroxy, hydrogen or alkyl, with l being equal to 1 and k being equal to 1, the same procedure can be used. When k is equal to zero, l is equal to 1 and j is equal to 1, then the amine R$^{10}$—NH$_2$ can be added to the corresponding α,β-unsaturated carboxylic acid derivative in the sense of a Michael addition. The primary amines obtained in this manner can subsequently be derivatized by reaction with carboxylic acid chlorides or anhydrides, chloroformic acid esters or sulphochlorides according to conventional methods. Where k is equal to zero, l is equal to 1 and j is equal to zero, the corresponding α-amino acids are commercially available or can be obtained according to syntheses described in the literature. Where k is equal to zero, l is equal to 1 and j is equal to 2, corresponding γ-keto esters can be used and can be converted into the desired amines by reductive amination with R$^{10}$—NH$_2$. Where l is equal to zero and k is equal to 1, corresponding ketones can be prepared according to methods described by L. E. Fisher et al., *Org. Prep. Proc. Int.*, 22: 399–484 (1990), or by K. Matsumoto et al., *Chem. Pharm. Bull.*, 34: 4516 (1986). Where R$^{10}$ is hydroxy, with l being equal to zero and k being equal to zero, an ester of the commercially available DL-4-amino-3-hydroxybutyric acid can, for example, be used. Where R$^{10}$ is carboxyalkyl, the procedure described by O. Tsuge et al. [*Bull. Chem. Soc. Jpn.* 59: 2537–45 (1986)] can be used.

Compounds of formula XXVII (Scheme 9) can be reacted e.g. with a Wittig-Horner reagent, such as triethyl phosphonoacetate, and a base, such as sodium alcoholate, in a solvent, such as ethanol, at RT or elevated temperature. The thereby obtained unsaturated compounds are hydrogenated on a catalyst, such a Pd/C, in a solvent, such as ethanol, and subsequently converted into the compounds XXVIII by removal of the protecting group.

Scheme 9

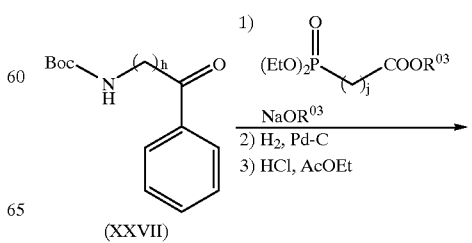

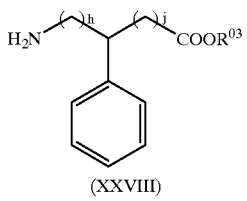

(XXVIII)

$R^{03}$ = alkyl, aralkyl

In addition to the processes described above, the substituent $R^1$ can be varied in the scope of the definitions of general formula 1. In this process variant (Scheme 10), a thiazole derivative of formula XXXVIII with intermediate protection of the acid functions in $R^2$ and $R^3$ can be guanidated [Tet. Lett., 29: 3183–86 (1988)]. Compound XXVIII is reacted with an isocyanate for the manufacture of the corresponding urea derivatives.

Compounds of the type XXXVIII can be obtained, for example, from compounds XIV after reaction with the corresponding amine components and removal of the Boc protecting group. When a is equal to zero, the procedure starts from corresponding thiazole base compounds of Schemes, 1a, 1b and 1d.

Scheme 10

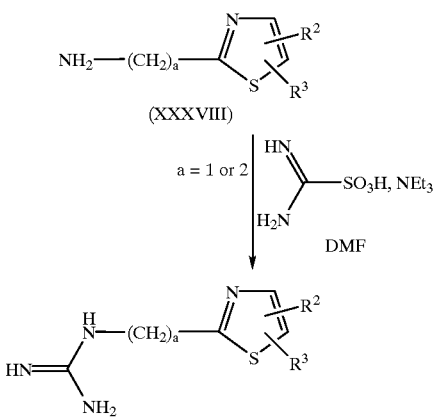

In the case where m is equal to zero and f and g are equal to zero and c is equal to 1 the corresponding compounds can be prepared according to Scheme 2, wherein the substituent $R^2$ is introduced by formation of an amide bond on the thiazole structure.

The invention also includes intermediates of the formulas

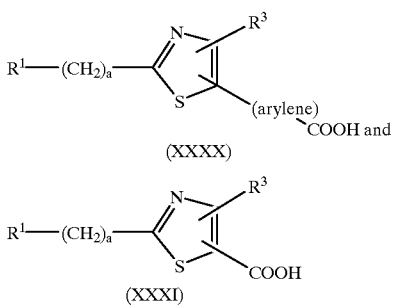

and their salts in which $R^1$, $R^3$ and a have the previously given significance and wherein in formula XXXI $R^3$ is not hydrogen or methyl when $R^1$ is

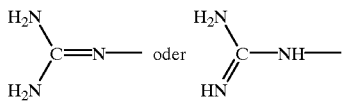

Especially preferred intermediates are:
Ethyl 2-guanidino-4-propyl-thiazole-5-carboxylate hydrobromide,
ethyl 2-guanidino-4-phenyl-thiazole-5-carboxylate hydrobromide,
ethyl 4-tert-butyl-2-guanidino-thiazole-5-carboxylate hydrobromide,
ethyl 4-cyclopentyl-2-guanidino-thiazole-5-carboxylate hydrobromide,
ethyl 3-(3-amino-benzoylamino)-3-phenyl-propionate hydrochloride,
ethyl rac-3-(2-benzyloxycarbonylamino-acetylamino)-3-phenyl-propionate,
ethyl rac-6-tert-butoxycarbonylamino-3-phenyl-hexanoate,
ethyl rac-6-amino-3-phenyl-hexanoate hydrochloride,
ethyl [(2-guanidino-thiazole-4-carbonyl)-amino]-acetate,
[(2-guanidino-thiazole-4-carbonyl)-amino]-acetic acid,
Cbz-(L)-aspartic acid 4-tert-butyl ester 1-N-phenyl-amide,
(L)-aspartic acid 4-tert-butyl ester 1-N-phenyl-amide,
ethyl rac-3-(3-benzyloxycarbonylamino-propionylamino)-3-phenyl-propionate,
ethyl rac-3-(3-amino-propionylamino)-3-phenyl-propionate,
2-guanidino-4-methyl-thiazole-5-carboxylic acid,
2-guanidino-4-propyl-thiazole-5-carboxylic acid hydrochloride,
2-guanidino-4-phenyl-thiazole-5-carboxylic acid,
4-tert-butyl-2-guanidino-thiazole-5-carboxylic acid hydrochloride,
4-cyclopentyl-2-guanidino-thiazole-5-carboxylic acid hydrochloride,
2-(tert-butoxycarbonylamino-methyl)-4-methyl-thiazole-5-carboxylic acid,
1-nitro-4-(2-nitro-propenyl)-benzene,
N-[4-methyl-5-(4-nitro-phenyl)-thiazol-2-yl]-guanidine,
N-[4-methyl-5-(3-nitro-phenyl)-thiazol-2-yl]-guanidine,
methyl 4-(2-guanidino-4-methyl-thiazol-5-yl)-benzoate,
methyl 3-(2-guanidino-4-methyl-thiazol-5-yl)-benzoate,
N-[5-(4-amino-phenyl)-4-methyl-thiazol-2-yl]-guanidine hydrochloride,
N-[5-(3-amino-phenyl)-4-methyl-thiazol-2-yl]-guanidine hydrochloride,
4-(2-guanidino-4-methyl-thiazol-5-yl)-benzoic acid,
3-(2-guanidino-4-methyl-thiazol-5-yl)-benzoic acid,
4-methyl-2-(3-methyl-ureido)-thiazole-5-carboxylic acid,
ethyl 2-(3-benzyl-ureido)-4-methyl-thiazole-5-carboxylate,
2-(3-benzyl-ureido)-4-methyl-thiazole-5-carboxylic acid,
ethyl 2-(3-benzyl-ureido)-thiazole-4-carboxylate,
2-(3-benzyl-ureido)-thiazole-4-carboxylic acid,
ethyl rac 3-(3-tert-butoxycarbonylamino-benzoylamino)-3-pyridin-3-yl-propionate,
ethyl rac 3-(3-amino-benzoylamino)-3-pyridin-3-yl-propionate,
ethyl rac 3-[2-(tert-butoxycarbonyl-cyclopropyl-amino)-acetylamino]-3-phenyl-propionate, ethyl rac 3-(2-cyclopropylamino-acetylamino)-3-phenyl-propionate hydrochloride,
rac 3-(3-nitro-phenylsulphonylamino)-3-phenyl-propionic acid,
ethyl rac 3-(3-nitro-phenylsulphonylamino)-3-phenyl-propionate,
ethyl rac 3-(3-amino-phenylsulphonylamino)-3-phenyl-propionate,
ethyl rac-3-[5-amino-2-(2-methoxy-ethoxy)-benzoylamino]-3-phenyl-propionate,
ethyl rac-3-(3-amino-5-benzyloxy-benzoylamino)-3-phenyl-propionate hydrochloride,
ethyl rac-7-tert-butoxycarbonylamino-3-phenyl-heptanoate,
ethyl rac-7-amino-3-phenyl-heptanoate hydrochloride,
ethyl rac-3-(3-amino-4-methoxy-benzoylamino)-3-phenyl-propionate,
ethyl 6-amino-5-oxo-hexanoate hydrochloride,
4-methyl-5-(3-nitro-phenyl)-thiazol-2-yl-amine,
1-benzyl-3-[4-methyl-5-(3-nitro-phenyl)-thiazol-2-yl]-urea,
1-[5-(3-amino-phenyl)-4-methyl-thiazol-2-yl]-3-benzyl-urea,
rac 3-pyridin-3-yl-pentanedicarboxylic acid monoethyl ester
ethyl [[2-(3-benzyl-ureido)-thiazole-4-carbonyl]-amino]-acetate,
[[2-(3-benzyl-ureido)-thiazole-4-carbonyl]-amino]-acetic acid,
tert-butyl (S)-N-benzyl-3-benzyloxycarbonylamino-succinamate,
tert-butyl (S)-3-amino-N-benzyl-succinamate,
tert-butyl (S)-3-benzyloxycarbonylamino-N-(3-methoxy-phenyl)-succinamate,
tert-butyl (S)-3-amino-N-(3-methoxy-phenyl)-succinamate,
tert-butyl (S)-2-(2-benzyloxycarbonylamino-3-tert-butoxycarbonyl-propionylamino)-benzoate,
tert-butyl (S)-2-(2-amino-3-tert-butoxycarbonyl-propionylamino)-benzoate,
ethyl 3-[(2-guanidino-4-methyl-thiazole-5-carbonyl)-amino]-benzoate,
3-[(2-guanidino-4-methyl-thiazole-5-carbonyl)-amino]-benzoic acid,
tert-butyl rac-3-tert-butoxycarbonylmethyl-2-oxo-piperidine-1-carboxylate,
tert-butyl rac-3-benzylcarbamoyl-6-tert-butoxycarbonylamino-hexanoate,
ethyl rac-6-amino-3-benzylcarbamoyl-hexanoate hydrochloride,
ethyl 2-phenoxycarbonylamino-thiazole-4-carboxylate,
ethyl 2-(3-pyridin-2-ylmethyl-ureido)-thiazole-4-carboxylate,
2-(3-pyridin-2-ylmethyl-ureido)-thiazole-4-carboxylic acid,
ethyl 4-[2-(3-benzyl-ureido )-thiazol-4-yl-butyrate,
4-[2-(3-benzyl-ureido)-thiazol-4-yl]-butyric acid,
diethyl rac-2-(3-bromo-2-oxo-propyl)-succinate,
diethyl rac-2-(3-azido-2-oxo-propyl)-succinate,
diethyl rac-2-(3-amino-2-oxo-propyl)-succinate,
tert-butyl (S)-3-benzyloxycarbonylamino-N-pyridin-2-ylmethyl-succinamate,
tert-butyl (S)-3-amino-N-pyridin-2-ylmethyl-succinamate,
tert-butyl (S)-3-benzyloxycarbonylamino-N-pyridin-3-ylmethyl-succinamate,
tert-butyl (S)-3-amino-N-pyridin-3-ylmethyl-succinamate,
tert-butyl (S)-3-(2-benzyloxycarbonylamino-acetylamino)-N-pyridin-2-ylmethyl-succinamate,
tert-butyl (S)-3-(2-amino-acetylamino)-N-pyridin-2-ylmethyl-succinamate,
ethyl 2-(imidazolidin-2-ylideneamino)-thiazole-4-carboxylate hydrobromide,
2-(imidazolidin-2-ylideneamino)-thiazole-4-carboxylic acid,
ethyl rac-3-(2-benzyloxycarbonylamino-acetylamino)-3-pyridin-3-yl-propionate,
ethyl 3-(2-amino-acetylamino)-3-pyridin-3-yl-propionate hydrochloride,
ethyl 4-methyl-2-(tetrahydro-pyrimidin-2-ylidenamino)-thiazole-5-carboxylate hydrochloride and
4-methyl-2-(tetrahydro-pyrimidin-2-ylideneamino)-thiazole-5-carboxylic acid.

The compounds of formula I described above for use as therapeutically active substances are a further object of the invention.

Also an object of the invention are compounds described above for the production of medicaments for the prophylaxis and therapy of illnesses which are caused by a malfunction of the binding of adhesive proteins to vitronectin receptors.

Likewise an object of the invention are pharmaceutical compositions containing a compound of formula I described above and a therapeutically inert carrier. The invention likewise relates to a pharmaceutical composition as previously described, which additonally contains one or more compounds of general formula I or additionally one or more compounds selected from the group comprising anticoagulants, fibrinolytics as well as medicaments for the prophylaxis and therapy of illnesses which are caused by a malfunction of the binding of adhesive proteins to vitronectin receptors.

An object of the invention is also the use of the compounds described above for the production of medicaments for the treatment or prophylaxis of illnesses which are caused by a malfunction of the binding of adhesive proteins to vitronectin receptors.

Also an object of the invention is the use of one of the compounds described above for the production of medicaments e.g. for the treatment or prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi.

A further object of the invention comprises compounds which are manufacturable according to one of the described processes.

Likewise an object of the invention are methods for the treatment and prophylaxis of illnesses which are caused by a malfunction of the binding of adhesive proteins to vitronectin receptors and which are comprise by the administration of an effective amount of a compound of formula I.

A further object of the invention is a method for the treatment and phophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi, whereby an effective amount of one of the compounds described above is administered.

Likewise an object of the invention are compounds described above for the treatment and prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infection caused by viruses, bacteria or fungi.

The conversion of a compound of formula I into a pharmaceutical usable salt can be carried out by treatment of such a compound with an inorganic acid, for example a hydrohalic acid, such as, for example, hydrochloric acid or hydrobromic acid, sulphuric acid, nitric acid, phosphoric acid etc., or with an organic acid, such as, for example, acetic acid, citric acid, maleic acid, fumaric acid, tartaric acid, methanesulphonic acid or p-toluenesulphonic acid.

The corresponding carboxylate salts can also be prepared from the compounds of formula I by treatment with physiologically compatible bases.

The conversion of a compound of formula I into a pharmaceutically usable ester can be accomplished by treatment of such a compound in the usual or as described in the Examples.

As mentioned previously, the compounds of formula I and their pharmaceutically usable salts and esters inhibit especially the binding of various adhesive proteins such as fibrinogen, vitronectin, von Willebrand factor, fibronectin, thrombospondin and osteopontin to the vitronectin receptors (such as e.g. $\alpha_v\beta_3$, $\alpha_v\beta_5$, $\alpha_v\beta_6$, $\alpha_v\beta_8$, etc.) on the surface of different types of cell. The compounds therefore influence cell-cell and cell-matrix interactions. Since the vitronectin receptors play a rôle, inter alia, in the spread of tumor cell, in vascular regeneration, in the degredation of bone tissue, in the migration of smooth muscle cells in vascular walls and in the invasion of virus particles into target cells, the said compounds can be used as vitronectin receptor antagonists in the control or prevention of neoplasms, tumor metestasing, osteoporosis, Paget's disease, diabetic retinopathy, macular degeneration, restenosis following vascular intervention, psoriasis, arthritis, kidney failure as well as infections caused by viruses, bacteria or by fungi. Since the binding of the adhesive proteins to the fibrinogen receptor ($\alpha_{IIb}\beta_3$) on the surface of blood platelets is practically not inhibited, undesired side effects, such as e.g. bleeding, can be suppressed with the therapeutic application of the said compounds.

The inhibition of the binding of adhesive proteins such as e.g. fibrinogen to vitronectin receptors (such as e.g. $\alpha_v\beta_3$, $\alpha_v\beta_5$, $\alpha_v\beta_6$, $\alpha_v\beta_8$, etc.) by compounds of the present invention can be determined as described by L. Alig et al. [*J. Med. Chem.*, 35: 4393–4407 (1992)].

In detail thereto, the wells of microtitre plates (Nunc-Immunoplate MaxiSorp) were coated overnight at 4° C. with the vitronectin receptor $\alpha_v\beta_3$ (from human placenta, 100 μl/well) in a buffer system with 150 mmol/l NaCl, 1 mmol/ CaCl$_2$, 1 mmol/l MgCl$_2$, 0.0005% Triton X-100 and 20 mmol/l Tris HCl, pH 7.4. The non-specific binding sites were blocked by incubation with 3.5% bovine serum albumin (BSA from Fluka) at 20° C. for at least 1 h. Before the beginning of the test the plates were washed in each case once with 150 mmol/l NaCl, 1 mmol/l CaCl$_2$, 1 mmol/l MgCl$_2$ and 20 mmol/l Tris HCl, pH 7.4 (buffer A). The thus-coated plates can be stored for at least 2 months in the presence of 0.05% NaN$_3$ (in buffer A) at 4° C. in a humidity chamber without loss of binding activity. Fibrinogen (IMCO, free from fibronectin) was diluted to 1.5 μg/ml in buffer A in the presence of 1% BSA. The wells coated with the receptor were incubated with fibrinogen (100 μl/well) overnight at room temperature in the absence of or in the presence of increasing concentrations of RGDS (as the reference substance) or the compounds to be measured. Non-bound fibrinogen was removed by three-fold washing with buffer A, bound fibrinogen was detected by an ELISA procedure. Antibodies of rabbits directed against human fibrinogen (Dakopatts, Denmark), diluted in buffer A in the presence of 0.1% BSA, were added at room temperature for 1 h., followed by incubation with biotinylated antibodies directed against rabbit immunoglobulin (Amersham) for 30 min. Non-bound antibodies were removed by three-fold washing with buffer A. Thereafter, the pre-formed streptavidin-biotinylated peroxidase complex (Amersham) was added for 30 min. three-fold washing with buffer A was again carried out. After addition of the peroxidase substrate ABTS (2,2'-azino-bis(3-ethylbenzothiazoline-6-sulphonic acid), Boehringer Mannheim) the enzyme activity was measured with a multichannel photometer (UVmax, Molecular Devices). The difference between total binding activity (in the absence of a test substance) and non-specific binding activity (in the presence of 100 μM RGDS) is taken as the specific binding activity. The concentration of a test substance which is required to inhibit the specific binding activity by 50% was defined as the IC$_{50}$.

The isolation of the receptor $\alpha_v\beta_3$ used in the test can be carried out as follows: Human placenta is stored at –80° C. immediately after its excision. In order to extract the receptor, each placenta is superficially thawed and cut into narrow strips with a scalpel. The pieces are washed twice with a buffer of 150 mmol/l NaCl, 1 mmol/l CaCl$_2$, 1 mmol/l MgCl$_2$ and 20 mmol/l Tris HCl (pH 7.4). The proteins are extracted at room temperature for one hour with a buffer solution from 1% Triton X-100, 150 mmol/l NaCl, 1 mmol/l CaCl$_2$, 1 mmol/l MgCl$_2$, 20 mmol/l Tris HCl, 0.02% NaN$_3$, 0.5 mmol/l phenylmethane-sulphonyl fluoride, 1 mmol/l leupeptin and 2 mmol/l N-ethylmaleimide (pH 7.4) and filtered through sterile gauze. The filtrate is centrifuged at 30000 g for 30 min. at 4° C. The glycoproteins are firstly separated with the aid of a concanavalin A-Sepharose 4B column. The proteins bound to the column are eluted and then added to a Aeg-RGDS column. After repeated washing the bound vitronectin receptor is eluted by 3 mmol/l RGDS in a buffer of 0.1% Triton X-100, 150 mmol/l NaCl, 20 mmol/l Tris HCl, 1 mmol/l CaCl$_2$, 1 mmol/l MgCl$_2$, 0.05% NaN$_3$ (pH 7.0).

Table 1 shows examples of compounds according to formula 1, wherein these compounds have IC$_{50}$ values below 1 μM. These results have been obtained by using the foregoing test.

Table 1 rac 3-[2-[[(2-(3-Benzyl-ureido)-thiazol-4-ylcarbonyl]-amino]-acetylamino]-3-phenyl-propionic acid rac 4-[3-(2-Guanidino-4-methyl-thiazol-5-yl)-phenylcarbamoyl]-3-phenyl-butyric acid rac 3-[2-[(2-Guanidinomethyl-thiazol-4-ylcarbonyl)-amino]-acetylamino]-3-phenyl-propionic acid rac 3-[3-[(2-Guanidino-4-methyl-thiazol-5-carbonyl)-amino]-benzoylamino]-3-phenyl-propionic acid-hydrochloride rac 3-[3-[(4-tert-Butyl-2-guanidino-thiazol-5-ylcarbonyl)-amino]-benzoylamino]-3-pyridin-3-yl-propionic acid

[2-Guanidino-thiazol-4-carbonyl]-Gly-Asp-Val-OH hydrochloride (S)-N-Benzyl-3-(2-((2-(3-benzyl-ureido)-thiazole-4-carbonyl)-amino)-acetylamino)-succinamate trifluoroacetate Preferred compounds as described above have an IC$_{50}$ which is below 100 μM; especially preferred compounds have a value below 10 μM, particularly preferred compounds have a value below 1 μM.

The compounds of formula I and their pharmaceutically usable salts and esters can be used as medicaments (e.g. in the form of pharmaceutical preparations). The pharmaceutical preparations can be administered internally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula I and their pharmaceutical usable salts and esters can be processed with pharmaceutically inert, inorganic or organic adjuvants for the production of tablets, coated tablets, dragées and hard gelatine capsules. Lactose, corn starch or derivatives thereof, talc, stearic acid or its salts etc. can be used, for example, as such adjuvants for tablets, dragées and hard gelatine capsules.

Suitable adjuvants for soft gelatine capsules, are, for example, vegetable oils, waxes, fats, semi-solid substances and liquid polyols, etc.

Suitable for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations, can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

In accordance with the invention the compounds of formula I and their pharmaceutically usable salts and esters can be used as vitronectin receptor antagonists especially for the treatment or prophylaxis of neoplasms, tumor metastasing, tumor growth, osteoporosis, Paget's disease, diabetic retinopathy, macular degeneration, restenosis following vascular intervention, psoriasis, arthritis, fibrosis, kidney failure as well as infections caused by viruses, bacteria or fungi. The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1–3 individual doses, which can consist, for example, of the same amounts, should be appropriate. It will, however, be clear that the upper limit given above can be exceeded when this is shown to be indicated.

The invention is illustrated hereinafter by Examples, which having no limiting character.

EXAMPLE 1

13.9 ml of ethyl bromopyruvate are added to a solution of 11.81 g of 2-imino-4-thiobiuret (Aldrich) in 100 ml of ethanol and the reaction mixture is heated under reflux for 3 hours (J. Med. Chem. 34, 914–918 (1991)). Subsequently, the mixture is cooled to room temperature and the reaction product is precipitated by the addition of 550 ml of ethyl acetate and filtered off. There are obtained 4.6 g of yellowish ethyl 2-guanidino-thiazole-4-carboxylate hydrobromide. MS: 214 $(M)^+$.

EXAMPLE 2 a) 1.62 ml of bromine are added dropwise while stirring and cooling at 0–5° C. within 10 minutes to a 2-phase mixture of 5.06 ml of ethyl butyrylacetate and 14.4 ml of water (J. Chem. Soc. Perkin I 1982, 162). The mixture is stirred at 0° C. for a further 30 minutes, then the product is extracted with ether. After drying there are obtained 7.6 g of crude bromoketone, which is used immediately in Example 3.

b) Analogously to the procedure from Example 2a, using ethyl benzoylacetate or ethyl pivaloylacetate or ethyl cyclopentyl-carbonyl-acetate in place of ethyl butyrylacetate there is prepared the corresponding bromoketone.

EXAMPLE 3

Analogously to the procedure from Example 1, using ethyl 2-chloroacetate or the bromoketones prepared under Example 2 in place of ethyl bromopyruvate there are prepared the following compounds:
a) Ethyl 2-guanidino-4-methyl-thiazole-5-carboxylate hydrochloride. MS: 228 $(M^+)$
b) Ethyl 2-guanidino-4-propyl-thiazole-5-carboxylate hydrobromide, MS: 256 $(M^+)$
c) Ethyl 2-guanidino-4-phenyl-thiazole-5-carboxylate hydrobromide, MS: 290 $(M^+)$
d) Ethyl 4-tert-butyl-2-guanidino-thiazole-5-carboxylate hydrobromide, MS: 271 $(M+H)^+$
e) Ethyl 4-cyclopentyl-2-guanidino-thiazole-5-carboxylate hydrobromide, MS: 283 $(M+H)^+$.

EXAMPLE 4

146 ml of 3N sodium hydroxide solution are added to 14.6 g of the ester obtained under Example 1 and the reaction mixture is boiled under for reflux for 3 hours. (J. Med. Chem., 34, 914–918 (1991)). Then, the reaction mixture is cooled to RT, acidified with 73 ml of 6N hydrochloric acid and evaporated to ¼ of the volume. The precipitated material is filtered off and washed with water. After drying there are obtained 9.44 g of 2-guanidino-thiazole-4-carboxylic hydrochloride; MS: 186 $(M)^+$.

EXAMPLE 5

220 mg of 2-guanidino-4-methyl-thiazole-5-carboxylic acid (Example 29a), 225 mg of N-$\beta$-alanyl-$\beta$-alanine ethyl ester hydrochloride, 4 ml of DMF, 0.34 ml of N-methylmorpholine (NMM) and 455 mg of O-(benzotriaol-1-yl)-N,N,N',N'-tetra-methyluronium hexafluorophosphate (HBTU) are stirred at room temperature under argon for 21 hrs. The reaction mixture is diluted with ethyl acetate and washed firstly with a dilute aqueous solution of sodium carbonate and sodium chloride, then with dilute sodium chloride solution and finally with saturated sodium chloride solution. The organic phase is dried over sodium sulphate and evaporated in a vacuum. Chromatography on silica gel with ethyl acetate-ethanol 5:1 gives 190 mg of ethyl 3-[3-[(2-guanidino-4-methyl-thiazole-5-carbonyl)-amino-propionylamino]-propionate as a pale yellow foam; MS: 371 $(M+H)^+$.

EXAMPLE 6

144 mg of ethyl 3-[3-[(2-guanidino-4-methyl-thiazole-5-carbonyl)-amino]-propionylamino]-propionate are left to stand in 2.9 ml of 25% hydrochloric acid for seven hours. The reaction mixture is evaporated in a vacuum and the residue is triturated in 2.5 ml of acetonitrile, filtered off under suction, washed with acetonitrile and dried in a vacuum. There are obtained 125 mg of 3-[3-[(2-guanidino-4-methyl-thiazole-5-carbonyl)-aminol-propionylamino]-propionic acid hydrochloride (1:2) of m.p. 170° C. MS: 343 $(M+H)^+$.

EXAMPLE 7

In analogy to the method given in Example 5, from the sodium salt of 2-guanidino-thiazole-4-carboxylic acid and N-β-alanyl-β-alanine ethyl ester hydrochloride there is obtained ethyl 3-[3-[(2-guanidino-thiazole-4-carbonyl)-amino]-propionylamino]-propionate, m.p. 154–157° C., MS: 357 (M+H)⁺.

The sodium salt of 2-guanidino-thiazole-4-carboxylic acid is obtained from the acid described in Example 4 by crystallization from dilute NaOH, m.p. 206° C.

EXAMPLE 8

Analogously to Example 6, from ethyl 3-[3-[(2-guanidino-thiazole-4-carbonyl)-amino]-propionylamino]-propionate there is obtained 3-[3-[(2-guanidino-thiazole-4-carbonyl)-amino]-propionylamino]-propionic acid hydrochloride (1:1.35), m.p. 205–207° C., MS: 329 (M+H)⁺.

EXAMPLE 9

316 mg of tert.-butyl 3-[3-[(2-guanidino-4-methyl-thiazole-5-carbonyl)-amino]-benzoylamino]-propionate are stirred in 2.1 ml of methylene chloride and 2.1 ml of trifluoroacetic acid at RT for 2 hours. The solvents are evaporated and the residue obtained is triturated in MeCN. There are obtained 311 mg of 3-[3-[(2-guanidino-4-methyl-thiazole-5-carbonyl)-amino]-benzoylamino]-propionic acid trifluoroacetate (1:1.06) m.p. 212° C., MS: 391 (M+H)⁺.

The starting material can be prepared as follows:

a) 3.14 g of 3-benzyloxycarbonylamino-benzoic acid, 2.02 g of CDMT, 34 ml of THF and 1.3 ml of NMM are stirred RT for 2.5 hrs. After the addition of 2.1 g of β-alanine tert.-butyl ester hydrochloride and 1.3 ml of NMM the mixture is stirred RT overnight. The reaction mixture is diluted with ethyl acetate and washed in sequence with ice-cold dilute hydrochloric acid, water, dilute sodium carbonate solution, water and saturated sodium chloride solution. After drying over sodium sulphate and evaporation of the solvent and crystallization from AcOEt there are obtained 3.83 g of tert.-butyl 3-(3-benzyloxycarbonylamino-benzoylamino)-propionate, m.p. 62–163° C., MS: 399 (M+H)⁺.

b) By catalytic hydrogenation on Pd/C in alcohol there is obtained therefrom N-(3-aminobenzoyl)-β-alanine tert.-butyl ester as an oil, MS: 265 (M+H)⁺.

c) This is coupled with 2-guanidino-4-methyl-thiazole-5-carboxylic acid according to the method give in Example 5. Chromatography on silica gel with methylene chloride-alcohol give tert.-butyl 3-[3-[(2-guanidino-4-methyl-thiazole-5-carbonyl)-amino]-benzoylamino]-propionate as a pale yellow foam, MS: 447 (M+H)⁺.

EXAMPLE 10

Analogously to Example 5, from 2-guanidino-4-methyl-thiazole-5-carboxylic aid and ethyl rac-3-(3-amino-benzoylamino)-3-phenyl-propionate hydrochloride there is obtained ethyl rac-3-[3-[(2-guanidino-4-methyl-thiazole-5-carbonyl)-amino]-benzoylamino]-3-phenyl-propionate, m.p. 177° C., MS: 495 (M+H)⁺.

The starting material can be prepared as follows:
a) According to the method described in Example 9a), from 3-tert.-butoxycar-bonylamino-benzoic acid and ethyl rac-3-amino-3-phenyl-propionate hydrochoride there is obtained ethyl rac-3-(3-tert-butoxycarbonylamino-benzoylamino)-3-phenyl-propionate, m.p. 130–131° C., MS: 413 (M+H)⁺.
b) 985 mg thereof are dissolved in 4.5 ml of ethyl acetate, treated with 4.5 ml of 4N HCl in ethyl acetate and stirred at RT for 1 hr. After evaporation of the solvent in a vacuum there is obtained ethyl rac-3-(3-amino-benzoylamino)-3-phenyl-propionate hydrochloride (1:1.15) as a yellow foam, MS: 313 (M+H)⁺.

EXAMPLE 11

About 100 mg of ethyl rac 3-[3-[(2-guanidino-4-methyl-thiazole-5-carbonyl)-amino]-benzoylamino]-3-phenyl-propionate are left to stand in 2.1 ml of 25 percent hydrochloric acid at RT for 6 hrs. The solution is evaporated and the residue is taken up in water and again evaporated. There is obtained rac 3-[3-[(2-guanidino-4-methyl-thiazole-5-carbonyl)-amino]-benzoylamino]-3-phenyl-propionic acid hydrochloride (1:1.27), m.p. 155–162° C., MS: 467 (M+H)⁺.

EXAMPLE 12

In analogously to Example 5, from 2-guanidino-thiazole-5-carboxylic acid and ethyl rac 3-(2-amino-acetylamino)-3-phenyl-propionate hydrochloride there is obtained ethyl rac 3-[2-[(2-guanidino-thiazole-5-carbonyl)-amino]-acetylamino]-3-phenyl-propionate, m.p. 145° C., MS: 419 (M+H)⁺.

The starting material can be prepared as follows:
a) Following Example 9a), by coupling Z-glycine with ethyl rac 3-amino-3-phenyl-propionate hydrochloride there is obtained ethyl rac 3-(2-benzyloxycarbonyl-amino-acetylamino)-3-phenyl-propionate, MS: 385 (M+H)⁺.
b) This is hydrogenated on Pd/C in ethyl alcohol, the filtered solution is adjusted to pH 3 with ethanolic hydrogen chloride solution and evaporated in a vacuum. There is thus obtained ethyl rac 3-(2-amino-acetylamino)-3-phenyl-propionate hydrochloride (1:1) as a colorless foam, MS: 251 (M+H)⁺.

EXAMPLE 13

Analogously to Example 6, from ethyl rac 3-[2-[(2-guanidino-thiazole-5-carbonyl)-amino]-acetylamino]-3-phenyl-propionate there is obtained rac 3-[2-[(2-guanidino-thiazole-5-carbonyl)-amino]-acetylamino]-3-phenyl-propionic acid hydrochloride (1:1.15), m.p. 245° C., MS: 391 (M+H)⁺.

EXAMPLE 14

In analogy to the method given in Example 9a, from 2-(3-benzyl-ureido)-thiazole-4-carboxylic acid and ethyl (RS)-6-amino-3-phenyl-hexanoate hydrochloride after chromatography on silica gel with ethyl acetate/hexane and crystallization in ether there is obtained ethyl (RS)-6-{[2-(3-benzyl-ureido)-thiazole-4-carbonyl]-amino}-3-phenyl-hexanoate, m.p. 93° C., MS: 495 (M+H)⁺.

The starting material can be prepared as follows:
a) A solution of 1.725 g of sodium in 150 ml of ethanol is treated at RT with 15 ml of triethyl phosphonoacetate and 13.17 g of tert-butyl (4-oxo-4-phenyl-butyl)-carbamate and stirred at 70° C. for 6 hrs. The reaction mixture is concentrated in a vacuum, diluted with ethyl acetate and washed in sequence with dilute hydrochloric acid, water and saturated sodium chloride solution. The ethyl acetate solutions are dried over sodium sulphate and evaporated. After chromatography on silica gel with acetone-hexane there is obtained a mixture of ethyl 6-tert-butoxycarbonylamino-3-phenyl-hex-2-enoate and ethyl 6-tert-butoxycarbonylamino-3-phenyl-hex-3-enoate as an oil, MS: 334 (M+H)⁺.
b) By catalytic hydrogenation on Pd/C in ethanol there is obtained therefrom ethyl (RS)-6-tert-butoxycarbonylamino-3-phenyl-hexanoate as a colorless oil, MS: 336 (M+H)⁺.
c) Cleavage of the protecting group with HCl in ethyl acetate leads to the hydrochloride of ethyl (RS)-6-amino-3-phenyl-hexanoate, MS: 235 (M)⁺.

EXAMPLE 15

172 mg of ethyl (RS)-6-{[2-(3-benzyl-ureido)-thiazole-4-carbonyl]-amino}-3-phenyl-hexanoate in 3.5 ml of ethanol are treated with 0.52 ml of 1N NaOH and stirred at RT for 6 hrs. The reaction mixture is concentrated in a vacuum, diluted with ethyl acetate and washed with dilute hydrochloric acid, water and sodium chloride solution. The ethyl acetate solution is dried and evaporated in a vacuum. Chromatography on silica gel with ethyl acetate and ethyl acetate/acetic acid 99:1 gives 76 mg of (RS)-6-{[2-(3-benzyl-ureido)-thiazole-4-carbonyl]-amino}-3-phenyl-hexanoic acid as a white foam, MS: 467 $(M+H)^+$.

EXAMPLE 16

2-Guanidino-thiazole-4-carboxylic acid monohydrate is coupled with ethyl (RS)-6-amino-3-phenyl-hexanoate in analogy to Example 5. Chromatography on silica gel with $CHCl_3$-MeOH gives ethyl (RS)-6-[(2-guanidinothiazole-4-carbonyl)-amino]-3-phenyl-hexanoate as a white foam, MS: 404 $(M+H)^+$.

2-Guanidino-thiazole-4-carboxylic acid monohydrate (m.p. >270° C.) is obtained from ethyl 2-guanidino-thiazole-4-carboxylate by saponification with sodium hydroxide solution in ethanol. After evaporation of the solvent the residue is taken up in water and the product is precipitated with hydrochloric acid at pH 2.

EXAMPLE 17

234 mg of ethyl (RS)-6-[(2-guanidino-thiazole-4-carbonyl)-amino]-3-phenyl-hexanoate are stirred in 4.6 ml of 25% hydrochloric acid at RT for 28 hrs. The solution is evaporated in a vacuum, the residue is taken up in water and neutralized with ammonia. The precipitate obtained is filtered off under suction and triturated in ethanol for purification. There are obtained 96 mg of (RS)-6-[(2-guanidino-thiazole-4-carbonyl)-amino]-3-phenyl-hexanoic acid, m.p. 230° C., MS: 376 $(M+H)^+$.

EXAMPLE 18

306 mg of 2-guanidino-thiazole-4-carboxylic acid monohydrate, 570 mg of HBTU, 6 ml of DMF and 0.51 ml of NMM are stirred RT for 40 min. After the addition of 531 mg of ethyl (RS)-3-(3-amino-benzoylamino)-3-phenyl-propionate hydrochloride the mixture is stirred at RT overnight. Working up as given in Example 5. Chromatography on silica gel with methylene chloride-EtOH 9:1 and trituration in isopropyl ether gives 505 mg of ethyl (RS)-3-{3-[(2-guanidino-thiazole-4-carbonyl)-amino]-benzoylamino}-3-phenyl-propionate, m.p. 117° C., MS: 481 $(M+H)^+$.

EXAMPLE 19

470 mg of (RS)-3-{3-[(2-guanidino-thiazol-4-carbonyl)-amino]-benzoylamino}-3-phenyl-propionate, 5 ml of acetic acid and 14.1 ml of 25% HCl are stirred at RT for 24 hrs. The reaction mixture is evaporated to dryness in a vacuum, the residue is dissolved in water, adjusted to pH 9 with ammonia and the solution is again evaporated. The residue obtained is triturated in water, filtered off under suction and dried. There are obtained 290 mg of (RS)-3-{3-[(2-guanidino-thiazole-4-carbonyl)-amino]-benzoylamino}-3-phenyl-propionic acid of m.p. 235° C., MS: 453 $(M+H)^+$.

EXAMPLE 20

In analogy to Example 9, from tert-butyl 3-[3-[(2-guanidino-thiazole-4-carbonyl)-amino]-benzoylamino]-propionate there is obtained 3-[3-[(2-guanidino-thiazole-4-carbonyl)-amino]-benzoylamino]-propionic acid trifluoroacetate (1:1.05), m.p. 240° C., MS: 377 $(M+H)^+$.

The tert-butyl 3-[3-[(2-guanidino-thiazole-4-carbonyl)-amino]-benzoylamino]-propionate is obtained in analogy to Example 5 from the sodium salt of 2-guanidino-thiazole-4-carboxylic acid and N-(3-aminobenzoyl)-$\beta$-alanine tert-butyl ester.

EXAMPLE 21

116 mg of (S)-N2-{2-[(2-guanidino-thiazole-4-carbonyl)-amino]-acetyl}-aspartic acid 4-tert-butyl ester 1-N-phenyl-amide are stirred in 0.7 ml of methylene chloride and 0.7 ml of TFA at RT for 3 hrs. The reaction mixture is evaporated in a vacuum, the residue is dissolved in water and again evaporated. The residue is then adjusted in water to pH 8 with ammonia, triturated, filtered off under suction, washed with water and dried. There are obtained 86 mg of (S)-N2-{2-[(2-guanidino-thiazole-4-carbonyl)-amino]-acetyl}-aspartic acid 1-N-phenyl-amide, m.p. 192° C. MS: 434 $(M+H)^+$.

The starting material can be obtained as follows:

a) According to the method give in Example 5, by coupling the sodium salt of 2-guanidino-thiazole-4-carboxylic acid with glycine ethyl ester hydrochloride there is obtained ethyl [(2-guanidino-thiazole-4-carbonyl)-amino] acetate, m.p. 190° C.

b) By saponification with NaOH in EtOH there is obtained therefrom [(2-guanidino-thiazole-4-carbonyl)-amino]-acetic acid, m.p. 230° C., MS: 244 $(M+H)^+$.

c) As given in Example 12a, from Z-(L)-aspartic acid 4-tert-butyl ester and alanine there is obtained Z-(L)-aspartic acid 4-tert-butyl ester 1-N-phenyl-amide, m.p. 87–88° C., MS: 399 $(M+H)^+$.

d) By catalytic hydrogenation on Pd/C in EtOH there is obtained therefrom (L)-aspartic acid 4-tert-butyl ester 1-N-phenyl-amide, m.p. 70–71° C., MS: 265 $(M+H)^+$.

e) As given in Example 5, from [(2-guanidino-thiazole-4-carbonyl)-amino]-acetic acid and (L)-aspartic acid 4-tert-butyl ester 1-N-phenyl-amide there is obtained (S)-N2-{2-[(2-guanidino-thiazole-4-carbonyl)-amino-acetyl}-aspartic acid 4-tert-butyl ester 1-N-phenyl-amide, m.p. 150° C., MS: 490 $(M+H)^+$.

EXAMPLE 22

In analogy to Example 5, from 2-guanidino-thiazole-4-carboxylic acid [J. Med. Chem., 34: 914–918 (1991)] and ethyl rac-3-(2-amino-acetylamino)-3-phenyl-propionate (preparation see Example 12) after chromatography on silylated silica gel RP 18 (water/ethanol gradient) and trituration in diethyl ether there is obtained ethyl rac-3-[2-[(2-guanidino-thiazole-4-carbonyl)-amino]-acetylamino]-3-phenyl-propionate, m.p. 177–178° C. (dec.), MS (ISP): 419 $(M+H^+$.

EXAMPLE 23

From ethyl rac-3-[2-[(2-guanidino-thiazole-4-carbonyl)-amino]-acetylamino]-3-phenyl-propionate by hydrolysis with conc. aqueous sodium hydroxide solution/ethanol 1:20 after 1 h. at 60° C., cooling to room temperature and addition of 2N hydrochloric acid to pH 3 there is obtained rac-3-[2-[(2-guanidino-thiazole-4-carbonyl)-amino]-acetylamino]-3-phenyl-propionic acid as the hydrochloride in the form of a colorless solid, m.p. 202–205° C., MS (ISP): 391 $(M+H)^+$.

EXAMPLE 24

By reaction of 2-guanidino-thiazole-4-carboxylic acid N-succinimidyl ester [J. Med. Chem., 34: 914–918 (1991)] and ethyl rac-3-(3-amino-propionylamino)-3-phenyl-propionate in DMF in the presence of triethylamine at 60° C.

there is obtained, after concentration of the reaction mixture and chromatography on silica gel (dichloro-methane/methanol 20:1 to 10:1), ethyl rac-3-[3-[(2-guanidino-thiazole-4-carbonyl)-amino]-propionylamino]-3-phenyl-propionate, m.p. 85–87° C., MS (ISP): 433 (M+H)$^+$.

The starting material can be prepared as follows:

a) By reaction of Z-b-Ala-OSu (Bachem) with ethyl rac-3-amino-3-phenyl-propionate hydrochloride in DMF in the presence of triethylamine at 60° C. there is obtained after usual working up ethyl rac-3-(3-benzyloxycarbonylaminopropionyl-amino)-3-phenyl-propionate, m.p. 100–101° C., MS (ISP): 399 (M+H)$^+$.

b) By catalytic hydrogenation of the product of the previous step in ethanol in the presence of Pd-carbon at room temperature there is obtained after usual working up and trituration in n-hexane ethyl rac-3-(3-amino-propionylamino)-3-phenyl-propionate, m.p. 163–165° C., MS (EI): 264 (M)$^+$.

EXAMPLE 25

From ethyl rac-3-[3-[(2-guanidino-thiazole-4-carbonyl)-amino]-propionyl-amino]-3-phenyl-propionate (Example 24 there is obtained by hydrolysis with LiOH in ethanol, subsequent neutralization with 2N hydrochloric acid, chromatography on silylated silica gel RP 18 (water/methanol gradient) and trituration in ethyl acetate rac-3-[3-[(2-guanidino-thiazole-4-carbonyl)-amino]-propionylamino]-3-phenyl-propionic acid, m.p. 105–107° C. (dec.), MS (ISP): 405 (M+H)$^+$.

EXAMPLE 26

By reaction of ethyl rac-3-(3-amino-propionylamino)-3-phenyl-propionate (Example 24) with 2-guanidino-4-methyl-thiazole-5-carboxylic acid (Example 29) in the presence of BOP as described in Example 44 there is obtained after chromatography on silylated silica gel RP 18 (water/ethanol gradient) and trituration in acetone ethyl rac-3-[3-[(2-guanidino-4-methyl-thiazole-5-carbonyl)-amino]-propionylamino]-3-phenyl-propionate, m.p. 106–107° C., MS (ISP): 447 (M+H)$^+$.

EXAMPLE 27

By hydrolysis of the product of Example 26 with 2N sodium hydroxide solution/ethanol there is obtained after chromatography on silylated silica gel RP 18 (water/ethanol gradient) and trituration in ethyl acetate rac-3-[3-[(2-guanidino-4-methyl-thiazole-5-carbonyl)-amino]-propionylamino]-3-phenyl-propionate, m.p. 176–177° C., MS (ISP): 419 (M+H)$^+$.

EXAMPLE 28

By treatment of [2-guanidino-thiazole-4-carbonyl]-Gly-Asp(OtBu)-Val-OtBu with HCl gas, dissolved in ethyl acetate, there is obtained, after filtration of the precipitate and crystallization from ethyl acetate, [2-guanidino-thiazole-4-carbonyl]-Gly-Asp-Val-OH as the hydrochloride, m.p. 93° C., MS (FAB): 458 (M+H)$^+$.

The starting material can be prepared as follows:

By reaction of H-Gly-Asp(OtBu)-Val-OtBu (J. Med. Chem. 1992, 35, 4393–4407) with 2-guanidino-thiazole-4-carboxylic acid [J. Med. Chem., 34: 914–918 (1991)] in the presence of HBTU and N-methylmorpholine in DMF analogously to Example 5 there is obtained after chromatography on silica gel (ethyl acetate/methanol 98:2) and crystallization from ethyl acetate/hexane [2-guanidino-thiazole-4-carbonyl]-Gly-Asp(OtBu)-Val-OtBu, m.p. 134–135° C., MS (FAB): 569 (M+H)$^+$.

EXAMPLE 29

The following compounds are prepared analogously to the procedure of Example 4 from the esters obtained according to Example 3:

a) 2-guanidino-4-methyl-thiazole-5-carboxylic acid, MS: 200 (M$^+$), b) 2-guanidino-4-propyl-thiazole-5-carboxylic acid hydrochloride, MS: 229 (M+H)$^+$, c) 2-guanidino-4-phenyl-thiazole-5-carboxylic acid, MS: 263 (M+H)$^+$, d) 4-tert-butyl-2-guanidino-thiazole-5-carboxylic acid hydrochloride, MS: 243 (M+H)$^+$, e) 4-cyclopentyl-2-guanidino-thiazole-5-carboxylic acid hydrochloride, MS: 255 (M+H)$^+$.

EXAMPLE 30

A suspension of 15.1 g of Boc-glycine thioamide in 150 ml of ethanol is treated with 9.9 ml of ethyl bromopyruvate and stirred at RT overnight. Subsequently, the reaction mixture is evaporated, the residue is taken up in ethyl acetate and washed with water. After chromatography on silica gel with ethyl acetate-hexane there are obtained 5.1 g of yellowish ethyl 2-(tert-butoxycarbonylamino-methyl)-thiazole-4-carboxylate MS: 286 (M)$^+$.

EXAMPLE 31 a) A suspension of 9.0 g of N-Boc-glycine thioamide in 90 ml of ethanol is treated with 7.0 ml of ethyl 2-chloroacetoacetate and stirred at 50° C. for 4 hours. Subsequently, the reaction mixture is evaporated, the residue is suspended in ethyl acetate, filtered and the filtrate, after evaporation, is chromatographed on silica gel with ethyl acetate-hexane. There are thus obtained 6.0 g of brownish ethyl 2-(tert-butoxycarbonylamino-methyl-4-methyl-thiazole-5-carboxylate; MS: 300 (M)$^+$.

EXAMPLE 32

The following compounds are prepared analogously to the procedure in Example 4 from the esters obtained according to Examples 30 and 31:

a) 2-(tert-Butoxycarbonylamino-methyl)-thiazole-4-carboxylic acid, MS: 257 (M–H)$^-$, b) 2-(tert-butoxycarbonylamino-methyl)-4-methyl-thiazole-5-carboxylic acid, MS: 273 (M+H)$^+$.

EXAMPLE 33 a) A mixture of 15.1 g of 4-nitrobenzaldehyde, 90 ml of acetic acid, 9.15 g of ammonium acetate and 23 ml of nitroethane is boiled at reflux for 2 hours. The yellow solution is cooled and poured onto ice-water. The mixture is extracted twice with ethyl acetate and the organic phase is evaporated. After chromatography on silica gel with hexane-ethyl acetate there are obtained 12.5 g of yellow crystalline 1-nitro-4-(2-nitro-propenyl)-benzene; MS: 208 (M)$^+$.

b) A suspension of 12.2 g of the nitroolefin obtained according to Example 33a) in 117 ml of methanol is treated while cooling at 3° C. with 26.7 ml of 35% hydrogen peroxide and subsequently with 14.7 ml of 2N sodium hydroxide solution. The reaction mixture is stirred at room temperature for a further 2 hours, then poured on to ice-water, acidified to pH 1 with 2N hydrochloric acid and extracted twice with ether. The organic phases are washed in sequence with water, bicarbonate solution, 5% sulphuric acidic iron sulphate solution and sodium chloride solution, dried and evaporated. 9.88 g of yellow crystalline epoxide are obtained. This material is suspended in 370 ml of ethanol, treated with 5.21 g of 2-imino-4-thiobiuret and boiled at reflux for 4.5 hours. The brown suspension is evaporated to half on a rotary evaporator and the precipitated material is filtered off. There are thus obtained 5.95 g of brown crystalline N-[4-methyl-5-(4-nitro-phenyl)-thiazol-2-yl]-guanidine; MS 278 (M+H)$^+$.

EXAMPLE 34

The following compounds are prepared analogously to the procedure of Example 33, but using i) 3-nitrobenzaldehyde or ii) methyl 4-formylbenzoate or iii) methyl 3-formylbenzoate in place of 4-nitrobenzaldehyde:

ai) (E)-1-Nitro-3-(2-nitro-propenyl)-benzene, MS: 208 (M)$^+$, aii) methyl (E)-4-(2-nitro-propenyl)-benzoate, MS: 221 (M)$^+$;

aiii) methyl (E)-3-(2-nitro-propenyl)-benzoate, MS: 221 (M)$^+$, bi) N-[4-methyl-5-(3-nitro-phenyl)-thiazol-2-yl]-guanidine, MS: 278 (M+H)$^+$, bii) methyl 4-(2-guanidino-4-methyl-thiazol-5-yl)-benzoate, MS: 290 (M)$^+$, biii) methyl 3-(2-guanidino-4-methyl-thiazol-5-yl)-benzoate, MS: 291 (M+H)$^+$.

EXAMPLE 35 a) A solution or 1.0 g of the compound from Example 33b in 100 ml of methanol is treated with 7.22 ml of 1N hydrochloric acid and 3 g of Raney nickel and hydrogenated overnight. The reaction mixture is filtered off from the catalyst, the filtrate is evaporated, the residue is azeotroped twice with ethanol and dried. There are obtained 1.2 g of greenish N-[5-(4-amino-phenyl)-4-methyl-thiazol-2-yl]-guanidine hydrochloride; MS: 248 (M+H)$^+$.

b) In a analogous manner to a), but using the nitro compound from Example 34 bi) there is obtained N-5-(3-amino-phenyl)-4-methyl-thiazol-2-yl]-guanidine hydrochloride; MS: 248 (M+H)$^+$.

EXAMPLE 36

A solution of 2.33 g of ester from Example 34bii) in 23 ml of THF is treated with 24 ml of 1N lithium hydroxide solution and stirred at 50° C. for 2.5 hours. After cooling 24 ml of 1N hydrochloric acid are added thereto and the precipitated acid is filtered off. After drying there are obtained 1.8 g of 4-(2-guanidino-4-methyl-thiazol-5-yl)-benzoic acid; MS: 277 (M+H)$^+$.

EXAMPLE 37

A solution of 2.9 g of ester from Example 34 biii) in 58 ml of THF is treated with 30 ml of 1N lithium hydroxide solution and stirred at room temperature overnight. Then, 30 ml of 1N hydrochloric acid are added thereto and the precipitated acid is filtered off. After drying there are obtained 2.3 g of 3-(2-guanidino-4-methyl-thiazol-5-yl)-benzoic acid; MS: 277 (M+H)$^+$.

EXAMPLE 38

Ethyl 4-methyl-2-[[(methylamino)carbonyl]amino]-thiazole-5-carboxylate was hydrolyzed analogously to Example 4 to the corresponding 4-methyl-2-(3-methyl-ureido)-thiazole-5-carboxylic acid; MS: 214 (M–H)$^-$.

EXAMPLE 39 a) 4.05 mg of benzyl isocyanate are added to a solution of 5.0 g of ethyl 2-amino-4-methyl-thiazole-5-carboxylate in 50 ml of DMF. The reaction mixture is stirred at RT overnight, evaporated on a rotary evaporator and the residue is suspended in methylene chloride/methanol 1:1. The insoluble material is filtered off and dried. There are obtained 4.6 g of colorless ethyl 2(3-benzyl-ureido)-4-methyl-thiazole-5-carboxylate; MS: 320 (M+H)$^+$.

b) A suspension of 3.6 g of the ester obtained under a) in 36 ml of ethanol was treated with 68 ml of 1N sodium hydroxide solution and boiled at reflux for 8 hours. Subsequently, the reaction mixture is poured into 70 ml of 1N ice-cold hydrochloric acid and the solution is evaporated to half volume. After cooling the precipitated crystals are filtered off and dried. There are thus obtained 2.25 g of colorless 2-(3-benzyl-ureido)-4-methyl-thiazole-5-carboxylic acid; MS: 292 (M+H)$^+$.

EXAMPLE 40 a) Analogously to Example 39a, but using ethyl 2-amino-thiazole-4-carboxylate in place of ethyl 2-amino-4-methyl-thiazole-5-carboxylate there is obtained 2-(3-benzyl-ureido)-thiazole-4-carboxylate; MS: 305 (M)$^+$.

b) A suspension of 7.0 g of the ester obtained under a) in 140 ml of ethanol was treated with 79 ml of 1N sodium hydroxide solution and stirred at 50° C. for 6 hours. The reaction mixture is cooled, 79 ml of 1N hydrochloric acid are added and the mixture is concentrated on a rotary evaporator to half volume. After cooling the precipitated crystals are filtered off and dried. There are thus obtained 3.6 g of colorless 2-(3-benzyl-ureido)-thiazole-4-carboxylic acid; MS: 277 (M)$^+$.

EXAMPLE 41 a) 26.7 ml of 4-methylmorpholine, 13.5 g of ethyl rac beta-amino-3-pyridine-propionate and 18.7 g of BOP are added to a solution of 10.0 g of 3-tert-butoxycarbonylamino-benzoic acid in 100 ml of DMF and the reaction mixture is stirred at RT overnight. Then, insoluble material is filtered off and the filtrate is evaporated. The residue is taken up in ethyl acetate, shaken once with 5% potassium hydrogen sulphate-10% potassium sulphate solution and twice with water. The organic phase is dried, evaporated and the residue is chromatographed on silica gel with hexane/ethyl acetate 4:1. The product fractions are evaporated, the residue is taken up again in ethyl acetate, shaken once with ice-cold sodium carbonate solution and twice with sodium solution. After drying and evaporation of the organic phase there are obtained 8.2 g of yellow ethyl rac 3-(3-tert-butoxycarbonylamino-benzoylamino)-3-pyridin-3-yl-propionate; MS: 414 (M+H)$^+$.

b) 7.3 g of the product from Example 41a) are dissolved in 73 ml of ethyl acetate, cooled to 0°, treated with 88 ml of 4N HCl gas in ethyl acetate solution and stirred at room temperature for 5 hours. Subsequently, the reaction mixture is evaporated, the residue is taken up in ethyl acetate, shaken once with ice-cold sodium solution and twice with sodium chloride solution. After drying and evaporation of the organic phase there are obtained 3.9 g of ethyl rac 3-(3-amino-benzoylamino)-3-pyridin-3-yl-propionate; MS: 314 (M+H)$^+$.

EXAMPLE 42 a) A solution of 5.0 g of N-tert-butyl-N-cyclopropylglycine in 100 ml of methylene chloride is treated with 5.1 ml of 4-ethyl morpholine, 3.87 g of EDC, 0.25 g of 4-dimethylaminopyridine and 5.1 g of rac 3-phenyl-beta-alanine ethyl ester hydro-chloride and stirred at RT for 5 hours. The reaction mixture is taken up in ethyl acetate, shaken once with 5% potassium hydrogen sulphate- 10% potassium sulphate solution and twice with water. The organic phase is dried, evaporated and the residue is chromatographed on silica gel with hexane-ethyl acetate 3:1. There are thus isolated 5.3 g of colorless ethyl rac-3-[2(tert-butoxycarbonyl-cyclopropyl-amino)-acetylamino]-3-phenyl-propionate; MS: 391 (M+H)$^+$.

b) 75.2 g of the product of Example 42a are dissolved in 52 ml of methylene chloride, cooled to 0°, treated and with 66 ml of 4N HCl gas in ethyl acetate and stirred at room temperature for 5 hours. Subsequently, the reaction mixture is evaporated. There are obtained 3.8 g of colorless ethyl rac 3-[2-(tert-butoxy-carbonyl-cyclopropyl-amino)-acetylamino]-3-phenyl-propionate; MS: 391 (M+H)$^+$.

EXAMPLE 43 a) A solution of 9.5 g of Z-L-Asp(OtBu)-OH in 95 ml of methylene chloride is treated with 3.2 ml of piperidine, 5.64 g of EDC and 0.36 g of 4-dimethylaminopyridine and stirred at RT for 5 hours. The reaction mixture is taken up in ethyl acetate, shaken once with 5% potassium hydrogen sulphate-10% potassium sulphate solution and twice with water. The organic phase is dried, evaporated and the residue is chromatographed with hexane/ethyl acetate 3:1. There are thus isolated 9.9 g of colorless tert-butyl (S)-3-benzyloxycarbonylamino-4-oxo-4-piperidin-1-yl-butyrate; MS: 391 (M+H)$^+$.

b) A solution of 4.0 g of the product obtained under a) is dissolved in 40 ml of ethanol, treated with 0.4 g of palladium-on-carbon and hydrogenated. The reaction mixture is filtered off from the catalyst and the filtrate is evaporated. The residue is dissolved in 26 ml of methylene chloride, treated [with] 1.96 g of EDC and 0.12 g of 4-dimethylaminopyridine and 2.13 g of Z-glycine and stirred at RT for 5 hours. The reaction mixture is taken up in ethyl acetate, shaken once with 5% potassium hydrogen sulphate-10% potassium sulphate solution and twice with water. The organic phase is dried, evaporated and the residue is chromatographed on silica gel with hexane/ethyl acetate 2:1. There are thus isolated 3.6 of colorless tert-butyl (S)-3-(2-benzyloxycarbonylamino-acetylamino)-4-oxo-4-piperidin-1-yl-butyrate; MS: 448 (M+H)$^+$.

c) A solution of 3.6 g of the product obtained under b) is dissolved in 36 ml of ethanol, treated with 0.36 g of palladium-on-carbon and hydrogenated. The reaction mixture is filtered off from the catalyst and the filtrate is evaporated. There are thus obtained 2.4 g of free amine, which is used immediately.

EXAMPLE 44

0.9 g of glycyl-beta-alanine ethyl ester hydrochloride is dissolved in 10 ml of dimethylformamide, treated with 1.92 ml of 4-ethylmorpholine, 0.68 g of acid from Example 4 and 1.34 g of benzotriazol-1-yloxy-tris(dimethylamino) phosphonium hexafluorophosphate (BOP). The reaction is stirred at room temperature overnight, then filtered off from insoluble material and the filtrate is evaporated on a rotary evaporator. The residue is chromatographed on a RP-18 column with a water-acetonitrile gradient. There is thus obtained 0.7 g of crystalline ethyl 3-[2-[(2-guanidino-thiazol-4-ylcarbonyl)-amino]-acetylamino]-propionate; MS: 343 (M+H)$^+$.

EXAMPLE 45

0.29 g of the ester obtained under Example 44 is suspended in 3 ml of tetrahydrofuran and treated with 2.54 ml of a 3N aqueous lithium hydroxide (sic) solution. The reaction mixture is stirred at room temperature for 2 hours, neutralized by the addition of 2.54 ml of 1N hydrochloric acid and evaporated on a rotary evaporator. After chromatography of the residue on a RP-18 column with a water-acetonitrile gradient there is obtained 0.1 g colorless crystalline 3-[2-[(2-guanidino-thiazol-4-ylcarbonyl)-amino]-acetylamino]-propionic acid; MS: 315 (M+H)$^+$.

EXAMPLE 46 a) 0.6 g of the anilino compound obtained according to the Example 35a is issolved in 12 ml of DMF, treated with 1.2 ml of 4-ethylmorpholine and 0.23 g of succinic acid anhydride and stirred at RT overnight. After evaporation and chromatography on a RP-18 column with a water-acetonitrile gradient there is obtained 0.12 g of beige N-[4-(2-guanidino-4-methyl-thiazol-5-yl)-phenyl]-succinamic acid monoamide, MS: 348 (M+H)$^+$.

b) Analogously to Example a), but using the anilino compound from Example 35b (in place of 13a) there is obtained N-[3-(2-guanidino-4-methyl-thiazol-5-yl)-phenyl]-succinamic acid monamide; MS: 348 (M+H)$^+$.

EXAMPLE 47

The following compounds are obtained analogously to Example 46, but using 3-phenylglutaric acid anhydride in place of succinic acid anhydride:

a) rac 4-[4-(2-Guanidino-4-methyl-thiazol-5-yl)-phenylcarbamoyl]-3-phenyl-butyric acid; MS: 438 (M+H)$^+$;

b) rac 4-[3-(2-guanidino-4-methyl-thiazol-5-yl)-phenylcarbamoyl]-3-phenyl-butyric acid; MS: 438 (M+H)$^+$.

EXAMPLE 48 a) 0.8 g of the anilino compound obtained according to Example 35a is dissolved in 16 ml of DMF, treated with 1.6 ml of 4-ethylmorpholine and 0.44 ml of adipic acid monomethyl ester and 1.11 g of BOP and stirred at RT overnight. After evaporation and chromatography of the residue on a RP-18 column with a water-acetonitrile gradient there is obtained 0.21 g of orange methyl 5-[4-(2-guanidino-4-methyl-thiazol-5-yl)-phenylcarbamoyl]-pentanoate; MS: 390 (M+H)$^+$.

b) Analogously to Example a), but using the anilino compound from Example 35b) in place of Example 35a) there is obtained methyl 5-[3-(2-guanidino-4-methyl-thiazol-5-yl)-phenylcarbamoyl]-pentanoate; MS: 390 (M+H)$^+$.

EXAMPLE 49

The following compounds are obtained analogously to the procedure described in Example 45, but using the ester from 48a) and, respectively, Example 48b):

a) 5-[4-(2-Guanidino-4-methyl-thiazol-5-yl)-phenylcarbamoyl]-pentanoic acid MS: 376 (M+H)$^+$;

b) 5-[3-(2-guanidino-4-methyl-thiazol-5-yl)-phenylcarbamoyl]-pentanoic acid MS: 376 (M+H)$^+$.

EXAMPLE 50 a) 0.6 g of the carboxylic acid obtained according to Example 36 is dissolved in 10 ml of DMF, treated with 0.82 ml of 4-ethylmorpholine and 0.72 g of ethyl rac$^\beta$-(aminomethyl)-4-chlorophenyl-propanecarboxylate and 0.96 g of BOP and stirred at RT overnight. After evaporation and chromatography of the residue on a RP-18 column with a water-acetonitrile gradient there is obtained 0.76 g of yellow ethyl rac 3-(4-chloro-phenyl)-4-[4-(2-guanidino-4-methyl-thiazol-5-yl)-benzoylamino]butyrate; MS: 500 (M+H)$^+$.

b) Analogously to Example a), but using the carboxylic acid from Example 37 (in place of Example 36) there is obtained ethyl rac 3-(4-chloro-phenyl)-4-[3-(2-guanidino-4-methyl-thiazol-5-yl)-benzoylamino]-butyrate; MS: 500 (M+H)+.

EXAMPLE 51

The following products are obtained analogously to Example 45, but using rac$^\beta$-phenyl-$^\beta$-alanine ethyl ester hydrochloride in place of ethyl $^\beta$-(aminomethyl)-4-chlorophenyl-propionate hydrochloride:
  a) Ethyl rac 3-[4-(2-guanidino-4-methyl-thiazol-5-yl)-benzoylamino]-3-phenyl-propionate; MS: 452 (M+H)+;
  b) ethyl rac 3-[3-(2-guanidino-4-methyl-thiazol-5-yl)-benzoylamino]-3-phenyl-propionate; MS: 452 (M+H)+.

EXAMPLE 52

The following products are obtained analogously to Example 45, but using the esters from Example 50 and, respectively, Example 51:
  a) rac 3-(4-Chloro-phenyl)-4-[4-(2-guanidino-4-methyl-thiazol-5-yl)-benzoylamino]-butyric acid; MS: 472 (M+H)+;
  b) rac 3-(4-chloro-phenyl)-4-[3-(2-guanidino-4-methyl-thiazol-5-yl)-benzoylamino]-butyric acid; MS: 472 (M+H)+;
  c) rac 3-[4-(2-guanidino-4-methyl-thiazol-5-yl)-benzoylamino]-3-phenyl-propionic acid; MS: 424 (M+H)+;
  d) rac 3-[3-(2-guanidino-4-methyl-thiazol-5-yl)-benzoylamino]-3-phenyl-propionic acid; MS: 424 (M+H)+.

EXAMPLE 53

The following compounds are obtained analogously to Example 44, but using (RS)-glycyl-3-phenyl-beta-alanine ethyl ester hydrochloride in place of glycyl-beta-alanine ethyl ester hydrochloride and with the acids from Example 29a–d) and, respectively, Example 32a):
  a) Ethyl rac 3-[2-[(2-guanidino-4-methyl-thiazol-5-ylcarbonyl)-amino]-acetylamino]-3-phenyl-propionate hydrochloride; MS: 433 (M+H)+;
  b) ethyl rac 3-[2-[(2-guanidino-4-propyl-thiazol-5-ylcarbonyl)-amino]-acetylamino]-3-phenyl-propionate; MS: 461 (M+H)+:
  c) ethyl rac 3-[2-[(2-guanidino-4-phenyl-thiazol-5-ylcarbonyl)-amino]-acetylamino]-3-phenyl-propionate; MS: 495 (M+H)+;
  d) ethyl rac 3-[2-[(4-tert-butyl-2-guanidino-thiazol-5-ylcarbonyl)-amino]-acetylamino]-3-phenyl-propionate; MS: 475 (M+H)+;
  e) ethyl rac 3-[2-[[2-(tert-butoxycarbonylamino-methyl)-thiazol-4-ylcarbonyl]-amino]-acetylamino]-3-phenyl-propionate; MS: 491 (M+H)+.

EXAMPLE 54

1.6 g of the product from Example 53e are dissolved in 16 ml of methylene chloride, treated at 0° with 16 ml of 4N HCl gas in ethyl acetate and stirred at room temperature for 5 hours. Subsequently, the reaction mixture is evaporated and there are obtained 1.6 g of ethyl rac 3-[2-[(2-aminomethyl-thiazol-4-ylcarbonyl)-amino]-acetylamino]-3-phenyl-propionate hydrochloride; MS: 391 (M+H)+.

EXAMPLE 55

1.35 ml of triethylamine and 0.41 g of formamidinesulphonic acid are added to a solution of 1.3 g of the product obtained according to Example 54 in 13 ml of DMF. The reaction mixture is stirred at RT overnight, then evaporated and the residue is chromatographed on a RP-18 column with a water-acetonitrile gradient. After evaporation of the product fractions and filtration of the residue over a Dowex column (Cl$^-$ form) there is isolated 0.65 g of colorless ethyl rac 3-[2-[(2-guanidinomethyl-thiazol-4-ylcarbonyl)amino]-acetylamino]-3-phenyl-propionate hydrochloride; MS: 433 (M+H)+.

EXAMPLE 56

The following products are obtained analogously to Example 45, but using the esters from Example 53a–d and, respectively, Example 54 and, respectively, Example 55:
  a) rac 3-[2-[(2-Guanidino-4-methyl-thiazol-5-ylcarbonyl)-amino]-acetylamino]-3-phenyl-propionic acid; MS: 405 (M+H)+;
  b) rac 3-[2-[(2-guanidino-4-propyl-thiazol-5-ylcarbonyl)-amino]-acetylamino]-3-phenyl-propionic acid; MS: 433 (M+H)+;
  c) rac 3-[2-[(2-guanidino-4-phenyl-thiazol-5-ylcarbonyl)-amino]-acetylamino]-3-phenyl-propionic acid; MS: 467 (M+H)+;
  d) rac 3-[2-[(4-tert-butyl-2-guanidino-thiazol-5-ylcarbonyl)-amino]-acetylamino]-3-phenyl-propionic acid; MS: 447 (M+H)+;
  e) rac 3-[2-[(2-aminomethyl-thiazol-4-ylcarbonyl)-amino]-acetylamino]-3-phenyl-propionic acid; MS: 363 (M+H)+;
  f) rac 3-[2-[(2-guanidinomethyl-thiazol-4-ylcarbonyl)-amino]-acetylamino]-3-phenyl-propionic acid; MS: 405 (M+H)+.

EXAMPLE 57

Analogously to Example 44, but using (RS)-glycyl-3-phenyl-beta-alanine ethyl ester hydrochloride in place of glycyl-beta-alanine ethyl ester hydrochloride and with the acid from Example 40b) there is obtained the following compound: ethyl rac 3-[2-[[(2-(3-benzyl-ureido)-thiazol-4-ylcarbonyl]-amino-acetylamino]-3-phenyl-propionate; MS: 510 (M+H)+.

Example 58

The following esters are obtained analogously to Example 44, but using the amine from Example 41b) in place of glycyl-beta-alanine ethyl ester hydrochloride and the acids from Example 29d) and, respectively, Example 38 in place of the acid from Example 4:
  a) Ethyl rac 3-[3-[(4-tert-butyl-2-guanidino-thiazol-5-ylcarbonyl)-amino]-benzoylamino]-3-pyridin-3-yl-propionate; MS: 538 (M+H)+;
  b) ethyl rac 3-[3-[[4-methyl-2-(3-methyl-ureido)-thiazol-5-ylcarbonyl]-amino]-benzoylamino]-3-pyridin-3-yl-propionate; MS: 511 (M+H)+.

EXAMPLE 59

The following esters are obtained analogously to Example 44, but using the amines from Example 42b) and, respectively, Example 43c) in place of glycyl-beta-alanine ethyl ester hydrochloride and the acid from Example 29 in place of the acid from Example 4:
  a) Ethyl rac 3-[2-[cyclopropyl-(2-guanidino-4-methyl-thiazol-5-ylcarbonyl)-amino]-acetylamino]-3-phenyl-propionate hydrochloride; MS: 473 (M+H)+;
  b) tert-butyl (S)-3-[2-[(2-guanidino-4-methyl-thiazol-5-ylcarbonyl)-amino]-acetylamino]-4-oxo-piperidin-1-yl-butyrate; MS: 496 (M+H)+.

EXAMPLE 60

Analogously to Example 44, but using the acid from Example 29a in place of the acid from Example 4there is obtained: ethyl 3-[2-[(2-guanidino-4-methyl-thiazol-5-ylcarbonyl)-amino]-acetylamino]-propionate; MS: 357 (M+H)$^+$.

EXAMPLE 61

The following products are obtained analogously to Example 45, but using the esters from Example 57 and, respectively, Example 58 and, respectively, Example 59 and, respectively, Example 60:

a) rac 3-[2-[[(2-(3-Benzyl-ureido)-thiazol-4-ylcarbonyl]-amino]-acetylamino]-3-phenyl-propionic acid; MS: 480 (M–H)$^-$;

b) rac 3-[3-[(4-tert-butyl-2-guanidino-thiazol-5-ylcarbonyl)-amino]-benzoyl-amino]-3-pyridin-3-yl-propionic acid; MS: 510 (M+H)$^+$;

c) rac 3-[3-[[4-methyl-2-(3-methyl-ureido)-thiazol-5-ylcarbonyl]-amino]-benzoylamino]-3-pyridin-3-yl-propionic acid; MS: 483 (M+H)$^+$;

d) rac 3-[2-[cyclopropyl-(2-guanidino-4-methyl-thiazol-5-ylcarbonyl)-amino]-acetylamino]-3-phenyl-propionic acid; MS: 445 (M+H)$^+$;

e) 3-[2-[(2-guanidino-4-methyl-thiazol-5-ylcarbonyl)-amino]-acetylamino]-propionic acid; MS: 329 (M+H)$^+$.

EXAMPLE 62

0.6 g of the product from Example 59b) is dissolved in 6 ml of methylene chloride, treated at 0° with 6 ml of 4N HCl gas in ethyl acetate and stirred at room temperature for 2.5 hours. Subsequently, the reaction mixture is evaporated and the residue is chromatographed on a RP-18 column with a water-acetonitrile gradient. There is obtained 0.37 g of colorless (S) 3-[2-[(2-guanidino-4-methyl-thiazol-5-ylcarbonyl)-amino]-acetylamino]-4-oxo-piperidin-1-yl-butyric acid; MS: 440 (M+H)$^+$.

EXAMPLE 63

Analogously to Example 44, but using the amine from Example 43c in place of glycyl-beta-alanine ethyl ester hydrochloride there is obtained: tert-butyl (S)-3-[2-[(2-guanidino-thiazol-4-ylcarbonyl)-amino]-acetylamino]-4-oxo-4-piperidin-1-yl-butyrate; MS: 482 (M+H)$^+$.

EXAMPLE 64

Analogously to Example 62, but starting from the product of Example 63 there is prepared (S)-3-[2-[(2-guanidino-thiazol-4-ylcarbonyl)-amino]-acetylamino]-4-oxo-4-piperidin-1-yl-butyric acid; MS: 426 (M+H)$^+$.

EXAMPLE 65

In analogy to Example 44, from 2-guanidino-4-methyl-thiazol-5-carboxylic acid (Example 29a) and ethyl rac 3-(3-amino-phenylsulphonylamino)-3-phenyl-propionate there is obtained ethyl rac 3-[3-[(2-guanidino-4-methyl-thiazol-5-ylcarbonyl)-amino]-benzenesulphonylamino]-3-phenyl-propionate; MS: 531 (M+H)$^+$.

The starting material can be prepared as follows:

a) A solution of 3-nitrophenylsulphochloride in 60 ml of ether is added dropwise within 20 minutes at 20–25° C. to a solution of 5.0 g of rac 3-amino-3-phenyl-propionic acid in 30 ml of 1N sodium hydroxide solution. 30 ml of 1N sodium hydroxide solution are added thereto after 30 minutes, 1 hour and 2 hours with vigorous stirring at room temperature. After stirring for a total of 6 hours the precipitated material is filtered off and washed with ether. Then, the residue is suspended in water-ethyl acetate, acidified with conc. hydrochloric acid and extracted with ethyl acetate. There are obtained 7.2 g of brownish rac-3-(3-nitro-phenylsulphonylamino)-3-phenyl-propionic acid; MS: 349 (M–H)$^-$.

b) Hydrogen chloride gas is conducted for 10 minutes into a solution of the residue obtained under a) in 70 ml of ethanol at 0° C. Then, the reaction mixture is stirred at 0° C. for a further 2 hours, subsequently evaporated on a rotary evaporator and the residue is dried. There are obtained 7.6 g of colorless ethyl rac-3-(3-nitro-phenylsulphonylamino)-3-phenyl-propionate; MS: 379 (M+H)$^+$.

c) A solution of 1.9 g of the ester obtained under b) in 19 ml of ethanol is treated with 0.5 g of Raney nickel and hydrogenated for 25 hours under normal conditions. After filtration of the catalyst and evaporation of the filtrate there are obtained 1.8 g of colorless ethyl rac-3-(3-amino-phenylsulphonylamino)-3-phenyl-propionate; MS: 349 (M+H)$^+$.

EXAMPLE 66

Analogously to Example 45, but using the ester from Example 65 there is obtained rac 3-[3-[(2-guanidino-4-methyl-thiazol-5-ylcarbonyl)-amino]-phenylsulphonylamino]-3-phenyl-propionic acid; MS: 503 (M+H)$^+$.

EXAMPLE 67

Analogously to the procedure described in Example 46, but using N-[4-(3-amino-phenyl)-thiazol-2-yl]-guanidine hydrobromide (see below for preparation) and 3-phenylglutaric anhydride there is obtained rac 4-[3-(2-guanidino-thiazol-4-yl)-phenylcarbamoyl]-3-phenyl-butyric acid, MS: 424 (M+H)$^+$.

Preparation of the educt:

a) Analogously to the procedure in Example 1, using 2-bromo-3'-nitro-acetophenone in place of ethyl bromopyruvate there is prepared N-[4-(3-nitro-phenyl)-thiazol-2-yl]-guanidine hydrobromide, MS: 264 (M+H)$^+$.

b) A solution of 3.0 g of the product obtained under a) in 80 ml of methanol and 5 ml of water is treated with 3 g of palladium-on-carbon and hydrogenated for 4 hours. Then, the catalyst is filtered off and the filtrate is evaporated. There are thus obtained 2.7 g of brownish N-[4-(3-amino-phenyl)-thiazol-2-yl]-guanidine hydrobromide, MS: 234 (M+H)$^+$.

EXAMPLE 68

Analogously to the procedure described in Example 50, but using 3-(2-guanidino-thiazol-4-yl)-benzoic acid hydrobromide (see below for preparation) in place of the carboxylic acid used there, there is obtained rac. 3-(4-chloro-phenyl)-4-[3-(2-guanidino-thiazol-4-yl)-benzoylamino]-butyric acid, MS: 458 (M+H)$^+$.

Preparation of the educt:

Analogously to the procedure in Example 1, but using 3-bromoacetylbenzoic acid in place of ethyl bromopyruvate there is prepared 3-(2-guanidino-thiazol-4-yl)-benzoic acid hydrobromide, MS: 263 (M+H)$^+$.

EXAMPLE 69

Analogously to the procedure described in Example 46b, but using 3-(4-methoxy-phenyl)-glutaric acid anhydride in place of succinic acid anhydride there is obtained:

rac 4-[3-(2-Guanidino-4-methyl-thiazol-5-yl)-phenylcarbamoyl]-3-(4-methoxy-phenyl)-butyric acid, MS: 468 (M+H)$^+$.

EXAMPLE 70

In analogy to Example 18, from 2-guanidino-4-methyl-thiazole-5-carboxylic acid and ethyl (RS)-3-[5-amino-2-(2-methoxy-ethoxy)-benzoylamino]-3-phenyl-propionate there is obtained ethyl (RS)-3-[5-[(2-guanidino-4-methyl-thiazole-5-carbonyl)-amino]-2-(2-methoxy-ethoxy)-benzoylaminol-3-phenyl-propionate as a pale yellow foam. MS: 569 (M+H)$^+$.

Preparation of ethyl (RS)-3-[5-amino-2-(2-methoxy-ethoxy)-benzoylamino]-3-phenyl-propionate:

a) 5-Benzyloxycarbonylamino-2-hydroxy-benzoic acid (J. Med. Chem. (1993), 36(26), 4201-7) is reacted with 1-chloro-2-methoxy-ethane in DMF at 0° C. in the presence of $K_2CO_3$ and sodium iodide to give 2-methoxyethyl 5-benzyloxycarbonylamino-2-(2-methoxy-ethoxy)-benzoate. M.p. 104–105° C., MS: 404 (M+H)$^+$.

b) This is saponified with 2N NaOH in methanol to give 5-benzyloxycarbonyl-amino-2-(2-methoxy-ethoxy)-benzoic acid, m.p. 130–131° C., MS: 346 (M+H)$^+$.

c) This is coupled with ethyl (RS)-3-amino-3-phenyl-propionate hydrochloride according to the method given in Example 9a) to give ethyl (RS)-3-[5-benzyloxycarbonyl-amino-2-(2-methoxy-ethoxy)-benzoylamino]-3-phenyl-propionate, m.p. 139–140° C., MS: 521 (M+H)$^+$.

d) By catalytic hydrogenation on Pd/C in ethanol there is obtained therefrom ethyl (RS)-3-[5-amino-2-(2-methoxy-ethoxy)-benzoylamino]-3-phenyl-propionate, m.p. 105–106° C., MS: 387 (M+H)$^+$.

EXAMPLE 71

197 mg of ethyl (KS)-3-[5-[(2-guanidino-4-methyl-thiazole-5-carbonyl)-amino]-2-(2-methoxy-ethoxy)-benzoylamino]-3-phenyl-propionate are left to stand at RT for 23 hrs. in 2 ml of acetic acid and 4 ml of 25% hydrochloric acid. The reaction mixture is evaporated to dryness and [the residue] is dried in a vacuum. The residue is lyophilized from acetic acid. There are obtained 192 mg of (RS)-3-[5-[(2-guanidino-4-methyl-thiazole-5-carbonyl)-amino]-2-(2-methoxy-ethoxy)-benzoylamino]-3-phenyl-propionic acid hydrochloride (1:1) as a white powder, MS: 451 (M+H)$^+$.

EXAMPLE 72

In the same manner as described in Example 18, from ethyl 2-guanidino-thiazole-5-carboxylic acid and ethyl (RS)-3-(3-amino-benzoylamino)-3-phenyl-propionate hydrochloride there is obtained ethyl (RS)-3-{3-[(2-guanidino-thiazole-5-carbonyl)-amino]-benzoylamino}-3-phenyl-propionate, m.p. 149° C., MS: 481 (M+H)$^+$.

EXAMPLE 73

In analogy to Example 19, from ethyl (RS)-3-{3-[(2-guanidino-thiazole-5-carbonyl)-amino]-benzoylamino}-3-phenyl-propionate there is obtained (RS)-3-[3-[(2-guanidino-thiazole-5-carbonyl)-amino]-benzoylamino]-3-phenyl-propionic acid, m.p. 196° C., MS: 453 (M+H)$^+$.

EXAMPLE 74

In a similar manner to that described in Example 5, but at 70° C., from 2-guanidino-4-methyl-thiazole-5-carboxylic acid and ethyl (RS)-3-(3-amino-5-benzyloxy-benzoylamino)-3-phenyl-propionate hydrochloride there is obtained ethyl (RS)-3-{3-benzyloxy-5-[(2-guanidino-4-methyl-thiazole-5-carbonyl)-amino]-benzoylamino}-3-phenyl-propionate, m.p. 116° C., MS: 601 (M+H)$^+$.

The starting material can be prepared as follows:

a) 3-Amino-5-hydroxy-benzoic acid (Tetrahedron (1983), 39(24), 4189–92) is converted in t-BuOH/water with di-tert.-butyl dicarbonate and triethylamine into 3-tert-butoxycarbonylamino-5-hydroxy-benzoic acid; m.p. 175° C., MS: 254 (M+H)$^+$.

b) This is converted at 56° C. in acetone in the presence of $K_2CO_3$ with benzyl bromide into benzyl 3-benzyloxy-5-tert-butoxycarbonylamino-benzoate; m.p. 130–131° C., MS: 433 (M)$^+$.

c) Saponification with sodium hydroxide solution in methanol at 40° C. gives 3-benzyloxy-5-tert-butoxycarbonylamino-benzoic acid, m.p. 194° C., MS: 343 (M)$^+$.

d) The latter is coupled with ethyl (RS)-3-amino-3-phenyl-propionate hydrochloride as given in Example 9a to give ethyl (RS)-3-(3-benzyloxy-5-tert-butoxycarbonylamino-benzoylamino)-3-phenyl-propionate, m.p. 115° C., MS: 519 (M+H)$^+$.

e) By treatment with HCl in ethyl acetate there is obtained therefrom ethyl (RS)-3-(3-amino-5-benzyloxy-benzoylamino)-3-phenyl-propionate hydrochloride as a white foam, MS: 418 (M)$^+$.

EXAMPLE 75

In analogy to Example 19, from ethyl (RS)-3-{3-benzyloxy-5-[(2-guanidino- 4-methyl-thiazole-5-carbonyl)-amino]-benzoylamino}-3-phenyl-propionate there is obtained (RS)-3-{3-benzyloxy-5-[(2-guanidino-4-methyl-thiazole-5-carbonyl)-amino]-benzoylamino}-3-phenyl-propionate, which is purified by trituration in acetone; m.p. 235° C., MS: 573 (M+H)$^+$.

EXAMPLE 76

According to the method given in Example 9a), from 2-(3-benzyl-ureido)-4-methyl-thiazole-5-carboxylic acid and ethyl (RS)-7-amino-3-phenyl-heptanoate hydrochloride there is obtained ethyl (RS)-7-{[2-(3-benzyl-ureido)-4-methyl-thiazole-5-carbonyl]-amino}-3-phenyl-heptanoate as a white foam, MS: 523 (M+H)$^+$.

The starting material can be prepared as follows:

a) In analogy to the method given in Example 14, from tert-butyl (5-oxo-5-phenyl-pentyl)-carbamate (J. Org. Chem. (1989), 54, 228–34) there is obtained a mixture of ethyl 7-tert-butoxycarbonylamino-3-phenyl-hept-2-enoate and ethyl 7-tert-butoxycarbonylamino-3-phenyl-hept-3-enoate as an oil, MS: 348 (M+H)$^+$.

b) By catalytic hydrogenation on Pd/C in alcohol there is obtained therefrom ethyl (RS)-7-tert-butoxycarbonylamino-3-phenyl-heptanoate as a colorless oil, MS: 350 (M+H)$^+$.

c) Cleavage of the protecting group with HCl in ethyl acetate gives the hydrochloride of ethyl (RS)-7-amino-3-phenyl-heptanoate, MS: 250 (M+H)$^+$.

EXAMPLE 77

Analogously to Example 15, from ethyl (RS)-7-{[2-(3-benzyl-ureido)-4-methyl-thiazole-5-carbonyl]-amino}-3-phenyl-heptanoate there is obtained (RS)-7-{[2-(3-benzyl-ureido)-4-methyl-thiazole-5-carbonyl]-amino}-3-phenyl-heptanoic acid as a colorless foam, MS: 495 (M+H)$^+$.

EXAMPLE 78

In analogy to Example 18, but at 50–60° C., from 2-guanidino-4-methyl-thiazole-5-carboxylic acid and ethyl (RS)-3-(3-amino-4-methoxy-benzoylamino)-3-phenyl-propionate there is obtained ethyl (RS)-3-{3-[(2-guanidino-4-methyl-thiazole-5-carbonyl)-amino]-4-methoxy-benzoylamino}-3-phenyl-propionate, m.p. 123–126° C., MS: 525 (M+H)$^+$.

The ethyl (RS)-3-(3-amino-4-methoxy-benzoylamino)-3-phenyl-propionate can be prepared according to the method given in Example 5 from 3-amino-4-methoxy-benzoic acid and ethyl (RS)-3-amino-3-phenyl-propionate hydrochloride; m.p. 116–118° C., MS: 343 (M+H)+.

EXAMPLE 79

205 mg of ethyl (RS)-3-{3-[(2-guanidino-4-methyl-thiazole-5-carbonyl)-amino]-4-methoxy-benzoylamino}-3-phenyl-propionate are stirred in 2 ml of ethyl acetate and 4 ml of 25% hydrochloric acid at RT. The precipitated (RS)-3-{3-[(2-guanidino-4-methyl-thiazole-5-carbonyl)-amino]-4-methoxy-benzoylamino}-3-phenyl-propionic acid hydrochloride (1:1) is filtered off under suction, washed with water and dried; m.p. 176–179° C., MS: 497 (M+H)+.

EXAMPLE 80

227 mg of [(2-guanidino-thiazole-4-carbonyl)-amino]-acetic acid, 249 mg of ethyl (RS)-3-amino-3-pyridin-3-yl-propionate dihydrochloride, 3 ml of DMF, 0.41 ml of N-MM and 354 mg of HBTU are stirred at RT for 23 hrs. and at 50° C. for 4 hrs. The reaction mixture is diluted with ethyl acetate and washed firstly with a dilute aqueous solution of sodium carbonate and sodium chloride, then with dilute sodium chloride solution and finally with saturated sodium chloride solution. The organic phase is dried over sulphate and evaporated in a vacuum. Chromatography on silica gel with methylene chloride-ethanol gives 101 mg of ethyl (RS)-3-{2-[(2-guanidino-thiazol-4-carbonyl)-amino]-acetylamino}-3-pyridin-3-yl-propionate- m.p. 114° C., MS: 420 (M+H)+.

[2-Guanidino-thiazole-4-carbonyl)-amino]-acetic acid is prepared as follows:

a) 2-Guanidino-thiazole-4-carboxylic acid is coupled according to the method just described to [give] ethyl [(2-guanidino-thiazole-4-carbonyl)-amino]-acetate, m.p. 190° C.

b) By saponification with NaOH in aqueous alcohol there is obtained, after evaporation of the solvent and acidification with dilute hydrochloric acid, [(2-guanidino-thiazole-4-carbonyl)-amino]-acetic acid, m.p. 230° C., MS: 244 (M+H)+.

EXAMPLE 81

84 mg of ethyl (RS)-3-{2-[(2-guanidino-thiazole-4-carbonyl)-amino]-acetylamino}-3-pyridin-3-yl-propionate are stirred at RT in 1 ml of acetic acid and 1.5 ml of 25% hydrochloric acid. After evaporation of the solvent mixture in a vacuum [the residue] is neutralized with dilute ammonia and again evaporated to dryness. The residue is triturated in a small amount of water, filtered off under suction, purified by trituration in alcohol and dried. There are obtained 55 mg of (RS)-3-{2-[(2-guanidino-thiazole-4-carbonyl)-amino]-acetylamino}-3-pyridin-3-yl-propionic acid, m.p. 186° C., MS: 392 (M+H)+.

EXAMPLE 82

In analogy to the method given in Example 9a, from 2-(3-benzyl-ureido)-thiazole-4-carboxylic acid and ethyl 6-amino-5-oxo-hexanoate hydrochloride there is obtained ethyl 6-{[2-(3-benzyl-ureido)-thiazole-4-carbonyl]-amino}-5-oxo-hexanoate, m.p. 135–136° C., MS: 433 (M+H)+.

The ethyl 6-amino-5-oxo-hexanoate hydrochloride (m.p. 74–76° C.) is obtained from 6-amino-5-oxo-hexanoic acid [J. MacGee et al., *Biochem. Med.* 17: 31–44 (1977)] by esterification in 5N HCl in EtOH.

EXAMPLE 83

According to the method described in Example 15, from ethyl 6-{[2-(3-benzyl-ureido)-thiazole-4-carbonyl]-amino}-5-oxo-hexanoate there is obtained 6-{[2-( 3-benzyl-ureido)-thiazole-4-carbonyl]-amino}-5-oxo-hexanoic acid, m.p. 169° C., MS: 405 M+H)+.

EXAMPLE 84

In the same manner as described in Example 5, from 2-guanidino-4-methyl-thiazole-5-carboxylic acid and ethyl (RS)-7-amino-3-phenyl-heptanoate hydrochloride there is obtained ethyl (RS)-7-[(2-guanidino-4-methyl-thiazole-5-carbonyl)-amino]-3-phenyl-heptanoate, m.p. 138° C., MS: 432 (M+H)+.

EXAMPLE 85

In analogy to Example 19, from ethyl (RS)-7-[(2-guanidino-4-methyl-thiazole-5-carbonyl)-amino]-3-phenyl-heptanoate there is obtained (RS)-7-[(2-guanidino-4-methyl-thiazole-5-carbonyl)-amino]-3-phenyl-heptanoic acid, m.p. 125° C., MS: 404 (M+H)+.

EXAMPLE 86

In analogy to the method given in Example 9a, from {[2-(3-benzyl-ureido)-thiazole-4-carbonyl]-amino}-acetic acid and (S)-aspartic acid 1-anilide 4-tert-butyl ester there is obtained(S)-3-(2-{[2-(3-benzyl-ureido)-thiazole-4-carbonyl]-amino}-acetylamino)-succinic acid 4-anilide 1-tert-butyl ester, m.p. 133° C., MS: 581 (M+H)+.

The starting material can be obtained as follows:

a) In analogy to the method given in Example 9a, from [[2-(3-benzyl-ureido)-thiazole-4-carboxylic acid and glycine ethyl ester hydrochloride there is obtained ethyl [[2-(3-benzyl-ureido)-thiazole-4-carbonyl]-amino]-acetate, m.p. 134° C., MS: 362 (M+H)+.

b) By saponification with sodium hydroxide solution in ethanol there is obtained therefrom [[2-(3-benzyl-ureido)-thiazole-4-carbonyl]-amino]-acetic acid, m.p. 185° C., MS: 335 (M+H)+.

EXAMPLE 87

240 mg of (S)-3-(2-{[2-(3-benzyl-ureido)-thiazole-4-carbonyl]-amino}-acetylamino)-succinic acid 4-anilide-1-tert-butyl ester are stirred in 2.4 ml of methylene chloride and 2.4 ml of trifluoroacetic acid at RT for 2 hrs. The reaction mixture is evaporated in a vacuum, the residue is taken up in toluene and the solution is again evaporated. The residue is crystallized from acetonitrile, filtered off under suction and dried. There are obtained 189 mg of (S)-3-{[2-(3-benzyl-ureido)-thiazole-4-carbonyl]-amino}-acetylamino)-succinic acid 4-anilide, m.p. 217° C., MS: (M+H)+.

EXAMPLE 88

Analogously to the procedure described in Example 46, from 1-[5-(3-amino-phenyl)-4-methyl-thiazol-2-yl]-3-benzyl-urea and 3-phenylglutaric anhydride there is obtained rac 4-{3-[2-(3-benzyl-ureido)-4-methyl-thiazol-5-yl]-phenylcarbamoyl}-3-phenyl-butyrate, MS: 529 (M+H)+.

The starting material can be prepared as follows:

a) Analogously to Example 38, but using thiourea in place of 2-imino-4-thiobiuret there is obtained 4-methyl-5-(3-nitro-phenyl)-thiazol-2-yl-amine, MS: 235 (M)+.

b) Analogously to the procedure descried in Example 39a, from 4-methyl-5-(3-nitro-phenyl)-thiazol-2-yl-amine there is obtained 1-benzyl-3-[4-methyl-5-(3-nitro-phenyl)-thiazol-2-yl]-urea MS: 369 (M+H)+.

c) 2.0 g of tin-II chloride dihydrate are added portionwise to a suspension of 1.0 g of the urea derivative prepared above in 9 ml of conc. hydrochloric acid and the mixture is stirred at 50° C. After 18 hrs. a further 0.5 g of tin-II chloride dihydrate is added and after a further 6 hrs. an additional 0.5 g of tin-II chloride dihydrate is added. Then, the reaction mixture is poured on to ice-water, made alkaline with sodium hydroxide solution and extracted twice with methylene chloride. There is obtained 0.86 g of brownish 1-[5-(3-amino-phenyl)-4-methyl-thiazol-2-yl]-3-benzyl-urea, MS: 339 (M+H)$^+$.

EXAMPLE 89

Analogously to the procedure described in Example 48a, from N-[5-(3-amino-phenyl)-4-methyl-thiazol-2-yl]-guanidine hydrochloride and rac 3-pyridin-3-yl-pentanedicarboxylic acid monoethyl ester there is obtained ethyl rac 4-[3-(2-guanidino-4-methyl-thiazol-5-yl)-phenylcarbamoyl]-3-pyridin-3-yl-butyrate, MS: 467 (M+H)$^+$.

The starting material can be prepared as follows:

2.2 ml of piperidine are added to a mixture of 10.7 g of pyridine-3-carbaldehyde and 24.8 ml of ethyl acetoacetate and the mixture is stirred for 3 hrs. Subsequently, a solution of 22.7 g of sodium hydroxide in 114 ml of ethanol is added thereto, diluted with 50 ml of ethanol and the reaction mixture is boiled under reflux overnight. After cooling 130 ml of ether are added thereto and the precipitated residue is filtered off under suction. This is dissolved in water, the solution is adjusted pH 5 and extracted with ethyl acetate. After evaporation of the organic phase there are obtained 4.2 g of rac 3-pyridin-3-yl-pentanedicarboxylic acid monoethyl ester, MS: 236 (M–H)$^-$.

EXAMPLE 90

Analogously to the procedure described in Example 45, from the ester from Example 89 there is obtained rac 4-[3-(2-guanidino-4-methyl-thiazol-5-yl)-phenyl-carbamoyl]-3-pyridin-3-yl-butyric acid, MS: 439 (M+H)$^+$.

EXAMPLE 91

By reacting N-5-(3-amino-phenyl)-4-ethyl-thiazol-2-yl]-guanidine with 3-phenylglutaric acid anhydride, as described in Example 46, there is obtained, after crystallization from methanol/acetic acid, the acetate salt of rac-4-[3-(4-ethyl-2-guanidino-thiazol-5-yl)-phenylcarbamoyl]-3-phenyl-butyric acid. M.p. 186–188° C.; MS: 452 (M+H)$^+$.

The starting material can be prepared as follows:

a) By reacting 3-nitrobenzaldehyde with 1-nitropropane, as described in Example 33 a), there is obtained E/Z-1-nitro-3-(2-nitro-but-1-enyl)-benzene in the form of yellow crystals. M.p. 68–72° C.; MS: 222 (M)$^+$.

b) By epoxidizing E/Z-1-nitro-3-(2-nitro-but-1-enyl)-benzene and subsequent reaction of the product obtained with 2-imino-4-thiobiuret, as described in Example 33 b), there is obtained N-[4-ethyl-5-(3-nitro-phenyl)-thiazol-2-yl]-guanidine. M.p. 149–151° C.; MS: 292 (M+H)$^+$.

c) By catalytically hydrogenating N-[4-ethyl-5-(3-nitro-phenyl)-thiazol-2-yl]-guanidine in ethanol/2N hydrochloric acid 3:1 in the presence of 10% palladium-charcoal there is obtained, after crystallization from ethanol, the hydrochloride salt of N-[5-(3-amino-phenyl)-4-ethyl-thiazol-2-yl]-guanidine. M.p. above 250° C.; MS: 262 (M+H)$^+$.

EXAMPLE 92

By reacting N-[5-(3-amino-phenyl)-4-propyl-thiazol-2-yl]-guanidine with 3-phenylglutaric acid anhydride, as described in Example 46, there is obtained rac-4-[3-(2-guanidino-4-propyl-thiazol-5-yl)-phenylcarbamoyl]-3-phenyl-butyric acid. M.p. 245–247° C. (dec.); MS: 466 (M+H)$^+$.

The starting material can be prepared as follows:

a) By reacting 3-nitrobenzaldehyde with 1-nitrobutane, as described in Example 33 a), there is obtained E/Z-1-nitro-3-(2-nitro-pent-1-enyl)-benzene in the form of yellow crystals. M.p. 45–47° C.; MS: 236 (M)$^+$.

b) By epoxidizing E/Z-1-nitro-3-(2-nitro-pent-1-enyl)-benzene and subsequent reaction of the product obtained with 2-imino-4-thiobiuret, as described in Example 33 b), there is obtained N-[5-(3-nitro-phenyl)-4-propyl-thiazol-2-yl]-guanidine. M.p. 137–139° C.; MS: 306 (M+H)$^+$.

c) By catalytically hydrogenating N-[5-(3-nitro-phenyl)-4-propyl-thiazol-2-yl]-guanidine in ethanol/2N hydrochloric acid 3:1 in the presence of platinum oxide there is obtained the hydrochloride salt of N-[5-(3-amino-phenyl)-4-propyl-thiazol-2-yl]-guanidine. M.p. 247–249° C.; MS: 276 (M+H)$^+$.

EXAMPLE 93

By reacting N-[5-(3-amino-phenyl)-4-butyl-thiazol-2-yl]-guanidine with 3-phenylglutaric acid anhydride, as described in Example 46, there is obtained rac-4-[3-(4-butyl-2-guanidino-thiazol-5-yl)-phenylcarbamoyl]-3-phenyl-butyric acid; MS: 480 (M+H)$^+$.

The starting material can be prepared as follows:

a) By reacting 3-nitrobenzaldehyde with 1-nitropentane, as described in Example 33 a), there is obtained E/Z-1-nitro-3-(2-nitro-hex-1-enyl)-benzene in the form of an orange colored oil; MS: 250 (M)$^+$.

b) By epoxidizing E/Z-1-nitro-3-(2-nitro-hex-1-enyl)-benzene and subsequent reaction of the product obtained with 2-imino-4-thiobiuret, as described in Example 33 b), there is obtained N-[4-butyl-5-(3-nitro-phenyl)-thiazol-2-yl]-guanidine. M.p. 140–142° C.; MS: 320 (M+H)$^+$.

c) By catalytically hydrogenating N-[4-butyl-5-(3-nitro-phenyl)-thiazol-2-yl]-guanidine in methanol/2N hydrochloric acid 3:1 in the presence of platinum there is obtained the hydrochloride salt of N-[5-(3-amino-phenyl)-4-butyl-thiazol-2-yl]-guanidine. M.p. 247–249° C.; MS: 290 (M+H)$^+$.

EXAMPLE 94

By reacting N-[5-(3-amino-phenyl)-4-pentyl-thiazol-2-yl]-guanidine with 3-phenylglutaric acid anhydride, as described in Example 46, there is obtained rac-4-[3-(2-guanidino-4-pentyl-thiazol-5-yl)-phenylcarbamoyl]-3-phenyl-butyric acid. M.p. 186–188° C. (dec.); MS: 494 (M+H)$^+$.

The starting material can be prepared as follows:

a) By reacting 3-nitrobenzaldehyde with 1-nitrohexane, as described in Example 33 a), there is obtained E/Z-1-nitro-3-(2-nitro-hept-1-enyl)-benzene in the form of an orange colored oil; MS: 264 (M)$^+$.

b) By epoxidizing E/Z-1-nitro-3-(2-nitro-hept-1-enyl)-benzene and subsequent reaction of the product obtained with 2-imino-4-thiobiuret, as described in Example 33 b), there is obtained N-[5-(3-nitro-phenyl)-4-pentyl-thiazol-2-yl]-guanidine. M.p. 135–137° C.; MS: 334 (M+H)$^+$.

c) By catalytically hydrogenating N-[5-(3-nitro-phenyl)-4-pentyl-thiazol-2-yl]-guanidine in methanol/2N hydrochloric acid 20:1 in the presence of 10% palladium-charcoal there is obtained the hydrochloride salt of N-[5-(3-amino-phenyl)-4-pentyl-thiazol-2-yl]-guanidine. M.p. 218–219° C.; MS: 304 (M+H)$^+$.

EXAMPLE 95

Analogously to Example 46, but using the corresponding 3-substituted glutaric acid anhydride, there are obtained:

a) rac-3-(4-Chloro-phenyl)-4-[3-(2-guanidino-4-methyl-thiazol-5-yl)-phenyl-carbamoyl]-butyric acid; MS: 472 (M+H)$^+$.

b) rac-4-[3-(2-Guanidino-4-methyl-thiazol-5-yl)-phenylcarbamoyl]-3-hydroxy-butyric acid; MS: 378 (M+H)$^+$.

c) 4-[3-(2-Guanidino-4-methyl-thiazol-5-yl)-phenylcarbamoyl]-butyric acid; MS: 362 (M+H)$^+$.

d) rac-4-[3-(2-Guanidino-4-methyl-thiazol-5-yl)-phenylcarbamoyl]-3-methyl-butyric acid; MS: 376 (M+H)$^+$.

EXAMPLE 96

Analogously to Example 46, using the 3-substituted glutaric acid anhydride described below, there are obtained:

a) rac-3-(3-Bromo-phenyl)-4-[3-(2-guanidino-4-methyl-thiazol-5-yl)-phenyl-carbamoyl]-butyric acid; MS: 516 (M+H)$^+$.

b) rac-3-(3,5-Dichloro-2-hydroxy-phenyl)-4-[3-(2-guanidino-4-methyl-thiazol-5-yl)-phenylcarbamoyl]-butyric acid; MS: 522 (M+H)$^+$.

c) rac-4-[3-(2-Guanidino-4-methyl-thiazol-5-yl)-phenylcarbamoyl]-3-(3-methoxy-phenyl)-butyric acid; MS: 468 (M+H)$^+$.

Preparation of the 3-substituted glutaric acid anhydride ai) 0.23 ml of piperidine is added to a solution of 1.85 g of 3-bromobenzaldehyde in 2.53 ml of ethyl acetoacetate and the mixture is shaken at room temperature for 5 hours. Subsequently, 2.27 g of solid sodium hydroxide and 10 ml of ethanol are added thereto and the mixture is shaken at 55° C. for 18 hours. The cooled mixture is treated with 20 ml of ether, the precipitated material is filtered off, taken up in water and acidified with conc. hydrochloric acid. The mixture is extracted twice with ethyl acetate and there is obtained from the organic phase 3.2 g of brown oily (RS)-3-(3-bromo-phenyl)-glutaric acid; MS: 284 (M–H)$^-$.

The corresponding glutaric acids are obtained in an analogous manner to ai) from 3,5-dichloro-2-hydroxy-benzaldehyde and, respectively, 3-methoxy-benzaldehyde.

bi) The material obtained under a) is dissolved in 30 ml of methylene chloride and treated with a solution of 2.17 g of DCC in 14 ml of methylene chloride. The mixture is stirred at room temperature overnight, then treated with 30 ml of hexane and the precipitated material is filtered off. There are thus obtained 1.2 g of brown crystalline (RS)-3-(3-bromo-phenyl)-glutaric acid anhydride; MS: 270 (M+H)$^+$.

The corresponding glutaric acid anhydrides are obtained in an analogous manner to bi) from 3-(3,5-dichloro-2-hydroxy-phenyl)-glutaric acid and, respectively, 3-(3-methoxy-phenyl)-glutaric acid.

EXAMPLE 97

Analogously to Example 46, but starting from N-[5-(5-amino-2-chloro-phenyl)-4-methyl-thiazol-2-yl]-guanidine and, respectively, N-[5-(3-amino-4-chloro-phenyl)-4-methyl-thiazol-2-yl]-guanidine, by reaction with 3-phenylglutaric acid anhydride there are obtained:

a) rac-4-[4-Chloro-3-(2-guanidino-4-methyl-thiazol-5-yl)-phenylcarbamoyl]-3-phenyl-butyric acid; MS: 472 (M+H)$^+$.

b) rac-4-[2-Chloro-5-(2-guanidino-4-methyl-thiazol-5-yl)-phenylcarbamoyl]-3-phenyl-butyric acid; MS: 472 (M+H)$^+$.

Preparation of the educt:

Analogously to Example 33, but using 2-chloro-5-nitro-benzaldehyde and, respectively, 4-chloro-3-nitro-benzaldehyde, there are obtained:

ai) N-[5-(2-Chloro-5-nitro-phenyl)-4-methyl-thiazol-2-yl]-guanidine; MS: 312 (M+H)$^+$;

bi) N-[5-(4-chloro-3-nitro-phenyl)-4-methyl-thiazol-2-yl]-guanidine; MS: 312 (M+H)$^+$.

Analogously to Example 35, but using the products from ai) and bi), there are obtained:

ci) N-[5-(5-Amino-2-chloro-phenyl)-4-methyl-thiazol-2-yl]-guanidine MS: 282 (M+H)$^+$;

di) N-[5-(3-amino-4-chloro-phenyl)-4-methyl-thiazol-2-yl]-guanidine MS: 282 (M+H)$^+$.

EXAMPLE 98

Analogously to Example 50, by reacting the acid from Example 37 with (S)-4-amino-2-butylsulphonylamino-butyric acid there is obtained (S)- 2-butylsulphonyl-amino-4-[3-(2-guanidino-4-methyl-thiazol-5-yl)-benzoylamino]-butyric acid hydrochloride (1:1); MS: 497 (M+H)$^+$.

Preparation of the educt:

The desired (S)-4-amino-2-butylsulphonylamino-butyric acid, MS: 239 (M+H)$^+$, is obtained from L-glutamine via N-butylsulphonyl-L-glutamine [MS: 267 (M+H)$^+$] analogously to a procedure described in J. Med. Chem. 40, 1779–88 (1997).

EXAMPLE 99

0.77 ml of 4-ethylmorpholine and a solution of 1.66 g of activated carbamic acid ester in 8 ml of acetonitrile are added to a solution of 0.75 g of aniline compound from Example 35b in 8 ml of acetonitrile. The reaction mixture is stirred at room temperature overnight, then evaporated and the residue is chromatographed on a RP-18 column with a water-acetonitrile gradient. There are thus obtained 0.23 g of orange ethyl rac-3-[3-[3-(2-guanidino-4-methyl-thiazol-5-yl)-phenyl]-ureido]-3-phenyl-propionate; MS: 467 (M+H)$^+$.

Preparation of the activated carbamic acid ester:

A solution of 4.0 g of ethyl rac-3-amino-3-phenyl-propionate hydrochloride in 94 ml of acetonitrile is treated with 2.2 ml of 4-ethylmorpholine, cooled to 0° C. and treated portionwise with 5.35 g of DSC (di-(N-succinimidyl)-carbonate). The reaction mixture is stirred at room temperature for 5 hours and then evaporated. The residue is taken up in ethyl acetate, washed with sodium chloride solution and evaporated. There are obtained 6.33 g of crude activated carbamate, which is used immediately.

EXAMPLE 100

Analogously to Example 45, from the ester prepared in Example 99 there is prepared rac-3-[3-[3-(2-guanidino-4-methyl-thiazol-5-yl)-phenyl]-ureido]-3-phenyl-propionic acid; MS: 439 (M+H)$^+$.

EXAMPLE 101

Analogously to Example 48, from the aniline compound from Example 35b with 3-phenylglutaric acid mono-ethyl ester there is prepared ethyl rac-4-[3-(2-guanidino-4-methyl-thiazol-5-yl)-phenylcarbamoyl]-3-phenyl-butyrate hydrochloride (1:1); MS: 466 (M+H)$^+$.

EXAMPLE 102

Analogously to Example 46, from the aniline compound prepared below with 3-phenylglutaric acid anhydride there is prepared rac-4-[[3-(2-guanidino-4-methyl-thiazol-5-yl)-phenyl]-methyl-carbamoyl]-3-phenyl-butyrate; MS: 452 (M+H)$^+$.

Preparation of the educt:

ai) 1.0 g of the aniline compound prepared in Example 35b is dissolved in 9 ml of ethanol, treated with 0.48 g of succinimide and the reaction mixture is heated to 45° C. 0.39 ml of 35% formaldehyde solution is added thereto and the mixture is boiled at reflux for 1 hour. After cooling and evaporation there are obtained 1.66 g of beige N-[5-[3-[(2,5-dioxo-pyrrolidin-1-ylmethyl)-amino]-phenyl]-4-methyl-thiazol-2-yl]-guanidine, MS: 359 (M+H)$^+$.

bi) 1.45 g of the material prepared under ai) are dissolved in 10 ml of DMSO and treated with 0.15 g of sodium borohydride. The reaction mixture is stirred at 110° C. for 15 minutes and, after cooling, poured on to ice-water. The precipitated material is filtered off and chromatographed on a RP-18 column with a water-acetonitrile gradient. There is obtained 0.28 g of beige N-[4-methyl-5-(3-methylamino-phenyl)-thiazol-2-yl]-guanidine, MS: 262 (M+H)$^+$.

EXAMPLE 103

Analogously to Example 48, from the aniline compound from Example 35b and methyl D,L-Z-glutamate there is obtained methyl rac-4-benzyloxycarbonylamino-4-[3-(2-guanidino-4-methyl-thiazol-5-yl)-phenylcarbamoyl]-butyrate; MS: 525 (M+H )$^+$.

EXAMPLE 104

Analogously to Example 45, from the ester prepared in Example 103 there is prepared rac-4-benzyloxycarbonylamino-4-[3-(2-guanidino-4-methyl-thiazol-5-yl)-phenylcarbamoyl]-butyric acid; MS: 511 (M+H)$^+$.

EXAMPLE 105

Analogously to Example 46, from the aniline compound prepared below with 3-phenylglutaric acid anhydride there is prepared methyl rac-5-[3-(4-carboxy-3-phenyl-butyrylamino)-phenyl]-2-guanidino-thiazole-4-carboxylate; MS: 482 (M+H)$^+$.

Preparation of the aniline component:

ai) A solution of 1.29 g of sodium in 22 ml methanol is added dropwise at 0° C. to a solution of 10 g of 3-nitrobenzaldehyde and 7.43 ml of dichloroacetic acid in 22 ml of ether. The reaction mixture is stirred at room temperature for 1 hour, poured into water and extracted with ether . After evaporation of the organic phase there are obtained 11.0 g of yellow crystalline chloroepoxide, which is further reacted immediately.

bi) A suspension of 11 g of the chloroepoxide prepared under ai) in 100 ml of methanol is treated with 4.83 g of 2-imino-4-thiobiuret and boiled at reflux for 4 hours. The reaction mixture is cooled to room temperature, evaporated to ⅓ of the volume and the precipitated material is filtered off. After washing and drying there are obtained 9.45 g of yellow methyl 2-guanidino-5-(3-nitro-phenyl)-thiazole-4-carboxylate hydrochloride; MS: 322 (M+H)$^+$.

ci) 4.5 g of the nitro compound obtained under bi) are dissolved in 200 ml methanol, treated with Raney-nickel and hydrogenated. After filtration and evaporation there are obtained 3.68 g of the desired methyl 5-(3-amino-phenyl)-2-guanidino-thiazole-4-carboxylate hydrochloride (1:1); MS: 292 (M+H)$^+$.

EXAMPLE 106

0.25 g of the ester prepared in Example 105 is dissolved in 2.5 ml of 3N potassium hydroxide solution and boiled at reflux for 30 minutes. After cooling the reaction mixture is acidified with 3 ml of 6N hydrochloric acid and evaporated. After chromatography on a RP-18 column with a water-acetonitrile gradient there is isolated 0.09 g of colorless rac-5-[3-(4-carboxy-3-phenyl-butyrylamino)-phenyl]-2-guanidino-thiazole-4-carboxylic acid; MS: 466 (M–H)$^-$.

EXAMPLE 107

The following compounds are prepared analogously to Example 41 from the acids described below and ethyl rac-3-(2-amino-acetylamino)-3-phenyl-propionate (see Example 12 for preparation):

a) Ethyl rac 3[2-[(2-guanidino-5-methyl-thiazol-4-ylcarbonyl)-amino]-acetylamino]-3-phenyl-propionate; MS: 433 (M+H)$^+$.

b) Ethyl rac-3-[2-[(5-tert-butyl-2-guanidino-thiazol-4-ylcarbonyl)-amino]-acetylamino]-3-phenyl-propionate; MS: 475 (M+H)$^+$.

c) Ethyl rac-3-[2-[(2-guanidino-5-phenyl-thiazol-4-ylcarbonyl)-amino]-acetylamino]-3-phenyl-propionate; MS: 495 (M+H)$^+$.

d) Ethyl rac-3-[2-[[2-guanidino-5-(3-nitro-phenyl)-thiazol-4-ylcarbonyl]-amino]-acetylamino]-3-phenyl-propionate; MS: 540 (M+H)$^+$.

Preparation of the acid components:

The following esters are prepared analogously to Example 105ai) and 105bi), but using acetaldehyde, pivaldehyde and, respectively, benzaldehyde in place of nitro-benzaldehyde:

ai) Methyl 2-guanidino-5-methyl-thiazole-4-carboxylate; MS: 214 (M)$^+$.

aii) Methyl 5-tert-butyl-2-guanidino-thiazole-4-carboxylate; MS: 257 (M+H)$^+$.

aiii) Methyl 2-guanidino-5-phenyl-thiazole-4-carboxylate; MS: 277 (M+H)$^+$.

The following acids are prepared analogously to Example 106 from the products of Example 107ai), 107aii), 107aiii) and 107bi):

bi) 2-Guanidino-5-methyl-thiazole-4-carboxylic acid; MS: 199 (M–H)$^-$.

bii) 5-tert-Butyl-2-guanidino-thiazole-4-carboxylic acid; MS: 243 (M+H)$^+$.

biii) 2-Guanidino-5-phenyl-thiazole-4-carboxylic acid; MS: 263 (M+H)$^+$.

biv) 2-Guanidino-5-(3-nitro-phenyl)-thiazole-4-carboxylic acid hydrochloride (1:1); MS: 306 (M–H)$^-$.

EXAMPLE 108

The following acids are prepared analogously to Example 45 from the esters of Example 107:

a) rac-3-[2-[(2-Guanidino-5-methyl-thiazol-4-ylcarbonyl)-amino]-acetylamino]-3-phenyl-propionic acid; MS: 405 (M+H)$^+$.

b) rac-3-[2-[(5-tert-Butyl-2-guanidino-thiazol-4-ylcarbonyl)-amino]-acetylamino]-3-phenyl-propionic acid; MS: 447 (M+H)$^+$.

c) rac-3-[2-[(2-Guanidino-5-phenyl-thiazol-4-ylcarbonyl)-amino]-acetylamino}-3-phenyl-propionic acid; MS: 467 (M+H)$^+$.

d) rac-3-[2-[2-Guanidino-5-(3-nitro-phenyl)-thiazol-4-ylcarbonyl]-amino]-acetyl-amino]-3-phenyl-propionic acid; MS: 512 (M+H)$^+$.

EXAMPLE 109

Analogously to the procedure described in Example 105ci), the nitro compound from Example 107d) is reduced to (RS)-3-[2-[[5-(3-amino-phenyl)-2-guanidino-thiazol-4-ylcarbonyl]-amino]-acetylamino]-3-phenyl-propionic acid; MS: 482 (M+H)$^+$.

EXAMPLE 110

The following compounds are prepared analogously to Example 41 from the acids described below and ethyl rac-3-(2-amino-acetylamino)-3-phenyl-propionate (see Example 12 for preparation):

a) Ethyl rac-3-[2-[[2-(3-benzyl-ureido)-5-methyl-thiazol-4-ylcarbonyl]-amino]-acetylamino]-3-phenyl-propionate; MS: 524 (M+H)+.

b) Ethyl rac-3-2-[[2-(3-benzyl-ureido)-5-phenyl-thiazol-4-ylcarbonyl]-amino]-acetylamino]-3-phenyl-propionate; MS: 475 (M+H)+.

Preparation of the acid components:

Analogously to Example 105ai), but using acetaldehyde in place of nitro-benzaldehyde, there is obtained the corresponding chloroepoxide and therefrom according to the procedure described in Example 105bi), but using thiourea in place of 2-imino-4-thiobiuret, there is obtained the compound ai) methyl 2-amino-5-methyl-thiazole-4-carboxylate; MS: 172 (M)+.

Analogously to Example 39, from the product from ai) prepared above there are prepared the compounds bi) methyl 2-(3-benzyl-ureido)-5-methyl-thiazole-4-carboxylate; MS: 305 (M)+, and ci) 2-(3-benzyl-ureido)-5-methyl-thiazole-4-carboxylic acid; MS: 291 (M)+.

The following compound is prepared according to the procedure described in Example 39a from 2-amino-5-phenyl-thiazole-4-carboxylic acid:

di) 2-(3-Benzyl-ureido)-5-phenyl-thiazole-4-carboxylic acid; MS: 353 (M)+.

EXAMPLE 111

The following acids are prepared analogously to Example 45 from the esters of Example 110:

a) rac-3-[2-[[2-(3-Benzyl-ureido)-5-methyl-thiazol-4-ylcarbonyl]-amino]-acetylamino]-3-phenyl-propionic acid; MS: 496 (M+H)+.

b) rac-3-[2-[[2-(3-Benzyl-ureido)-5-phenyl-thiazol-4-ylcarbonyl]-amino]-acetylamino]-3-phenyl-propionic acid; MS: 558 (M+H)+.

EXAMPLE 112

(RS)-4-[3-[2-(3-Benzyl-ureido)-5-methyl-thiazol-4-yl]-phenylcarbamoyl]-3-phenyl-butyric acid, MS: 529 (M+H)+, is prepared analogously to Example 47.

Preparation of the starting material:

a) Analogously to Example 39a, from 2-amino-5-methyl-4-(m-nitrophenyl)-thiazole hydrobromide there is prepared 1-benzyl-3-[5-methyl-4-(3-nitro-phenyl)-thiazol-2-yl]-urea; MS: 368 (M)+.

b) The product obtained under a) is reduced analogously to Example 105ci) to 1-[4-(3-amino-phenyl)-5-methyl-thiazol-2-yl]-3-benzyl-urea; MS: 339 (M+H)+.

EXAMPLE 113 rac-4-[[3-[2-(3-Benzyl-ureido)-5-methyl-thiazol-4-yl]-phenyl]-methyl-carbamoyl]-3-phenyl-butyric acid, MS: 543 (M+H)+, is prepared analogously to Example 46 from the aniline compound prepared below:

Preparation of the educt:

a) Analogously to Example 102ai, from the product of Example 112b there is prepared 1-benzyl-3-[4-[3-[(2,5-dioxo-pyrrolidin-1-ylmethyl)-amino]-phenyl]-5-methyl-thiazo-2-yl]-urea; MS: 450 (M+H)+.

b) Analogously to Example 102bi, from the product obtained above there is prepared 1-benzyl-3-[5-methyl-4-(3-methylamino-phenyl)-thiazol-2-yl]-urea; MS: 353 (M+H)+.

EXAMPLE 114

The following products are prepared analogously to Example 39, but using the 2-amino-thiazole prepared below and phenyl isocyanate, phenylethyl isocyanate and, respectively, butyl isocyanate:

a) Ethyl rac-3-phenyl-3-[2-[[2-(3-phenyl-ureido)-thiazol-4-ylcarbonyl]-amino]-acetyl-amino]-propionate; MS: 496 (M+H)+.

b) Ethyl rac-3-[2-[[2-(3-phenethyl-ureido)-thiazol-4-ylcarbonyl]-amino]-acetylamino]-3-phenyl-propionate; MS: 524 (M+H)+.

c) Ethyl rac-3-(2-[[2-(3-butyl-ureido)-thiazol-4-ylcarbonyl]-amino]-acetylamino)-3-phenyl-propionate; MS: 476 (M+H)+.

Preparation of the 2-amino-thiazole:

Analogously to Example 44, from 2-aminothiazole-4-carboxylic acid and (RS)-glycyl-3-phenyl-beta-alanine ethyl ester hydrochloride there is prepared ethyl (RS)-3-[2-[(2-amino-thiazol-4-ylcarbonyl)-amino]-acetylamino]-3-phenyl-propionate; MS: 377 (M+H)+.

EXAMPLE 115

The following acids are prepared analogously to Example 45 from the products of Example 114a–c:

a) rac-3-Phenyl-3-[2-[[2-(3-phenyl-ureido)-thiazol-4-ylcarbonyl]-amino]-acetylamino]-propionic acid; MS: 468 (M+H)+.

b) rac-3-[2-[[2-(3-Phenethyl-ureido)-thiazol-4-ylcarbonyl]-amino]-acetylamino]-3-phenyl-propionic acid; MS: 496 (M+H)+.

c) rac-3-(2-[[2-(3-Butyl-ureido)-thiazol-4-ylcarbonyl]-amino]-acetylamino]-3-phenyl-propionic acid; MS: 448 (M+H)+.

EXAMPLE 116

Analogously to Example 57, but using the amine components prepared below in place of rac-glycyl-3-phenyl-beta-alanine ethyl ester hydrochloride, there is prepared ethyl (RS)-3-[4-[[2-(3-benzyl-ureido)-thiazol-4-ylcarbonyl]-amino]-phenyl]-3-tert-butoxycarbonylamino-propionate; MS: 568 (M+H)+.

Preparation of the amine component:

a) 2.74 g of ethyl rac-3-amino-3-(4-nitro-phenyl)-propionate are dissolved in 50 ml of dioxan, treated with 2.40 g of di-tert-butyl dicarbonate and 2.5 ml of 4-ethylmorpholine and stirred at room temperature overnight. The reaction mixture is taken up in ethyl acetate and extracted once with 5% potassium hydrogen sulphate-10% potassium sulphate solution and once with water. After evaporation of the organic phase and chromatography of the residue on silica gel with hexane-ethyl acetate 4:1 there are obtained 1.56 g of colorless ethyl rac-3-tert-butoxycarbonylamino-3-(4-nitro-phenyl)-propionate; MS: 338 (M)+.

b) The product o0btained under a) is reduced analogously to Example 105ci) to ethyl rac-3-(4-amino-phenyl)-3-tert-butoxycarbonylamino-propionate; MS: 308 (M)+.

EXAMPLE 117

Analogously to Example 45, from the product of Example 116 there is prepared rac-3-[4-[[2-(3-benzyl-ureido)-thiazol-4-ylcarbonyl]-amino]-phenyl]-3-tert-buyoxy-carbonylamino-propionic acid; MS: 540 (M+H)+.

EXAMPLE 118

237 mg of the product prepared under Example 117 are dissolved in 2 ml of dimethylformamide, treated with 6N hydrochloric acid and stirred at room temperature overnight. After evaporation and chromatography of the residue on a RP-18 column with a water-acetonitrile gradient there are isolated 75 mg of colorless rac-3-amino-3-[4-[[2-(3-benzyl-ureido)-thiazol-4-ylcarbonyl]-amino]-phenyl]-propionic acid; MS: 438 (M−H)⁻.

EXAMPLE 119

0.51 g of the deduct prepared below is dissolved in 10 ml of DMF, treated with 0.4 ml of 4-ethylmorpholine and 0.21 ml of propionic anhydride and stirred at room temperature overnight. The reaction mixture is evaporated and the residue is chromato-graphed on silica gel with ethyl acetate. There is thus obtained 0.42 g of pale yellow ethyl rac-3-[4-[[2-(3-benzyl-ureido)-thiazol-4-ylcarbonyl]-amino]-phenyl]-3-propionylamino-propionate; MS: 524 (M+H)⁺.

Preparation of the educt:

a) Analogously to the procedure described in Example 54, from the product of Example 116 there is obtained ethyl rac-3-amino-3-[4-[[2-(3-benzyl-ureido)-thiazol-4-ylcarbonyl]-amino]-phenyl]-propionate; MS: 468 (M+H)⁺.

EXAMPLE 120

1.0 g of the educt prepared in Example 119a is dissolved in 4.4 ml of 1N sodium hydroxide solution and 5 ml of dioxan and treated at 0° C. within 15 minutes with 0.4 ml of butylsulphochloride and 2.4 ml of 1N sodium hydroxide solution. The reaction mixture is stirred at room temperature for 2.5 hours and then evaporated. The residue is treated with water, adjusted to pH1 with concentrated hydrochloric acid and extracted twice with ethyl acetate. The organic phases are evaporated and the residue is chromatographed on silica gel with hexane-ethyl acetate 1:2. There is isolated 0.1 g of beige ethyl rac-3-[4-[[2-(3-benzyl-ureido)-thiazol-4-ylcarbonyl]-amino]-phenyl]-3-butylsulphonylamino-propionate; MS: 586 (M−H)⁻.

EXAMPLE 121

The following acids are prepared analogously to Example 45 from the esters of Examples 119 and 120:

a) rac-3-[4-[[2-(3-Benzyl-ureido)-thiazol-4-ylcarbonyl]-amino]-phenyl]-3-propionyl-amino-propionic acid; MS: 496 (M+H)⁺.

b) rac-3-[4-[[2-(3-Benzyl-ureido)-thiazol-4-ylcarbonyl]-amino]-phenyl]-3-butyl-sulphonylamino-propionic acid; MS: 558 (M−H)⁻.

EXAMPLE 122

Analogously to Example 57, but using the amine component prepared below in place of rac-glycyl-3-phenyl-beta-alanine ethyl ester hydrochloride, there is prepared diethyl 3-[4-[[2-(3-benzyl-ureido)-thiazol-4-ylcarbonyl]-amino]-phenyl]-glutarate; MS: 539 (M+H)⁺.

Preparation of the amine component:

a) Hydrogen chloride is conducted for 10 minutes at 0° C. into a suspension of 3.0 g of 3-(4-nitro-phenyl)-glutaric acid in 30 ml of ethanol. The reaction mixture is stirred for 2 hours at 0° C., evaporated and the residue is chromato-graphed on silica gel with hexane-ethyl acetate 3:1. There are thus obtained 2.2 g of yellow diethyl 3-(4-nitro-phenyl)-glutarate; MS: 309 (M)⁺.

b) The product obtained under a) is reduced analogously to Example 105ci) to diethyl 3-(4-amino-phenyl)-glutarate; MS: 279 (M)⁺.

EXAMPLE 123

Analogously to Example 45, from the ester of Example 122, but using 6 equivalents of 1N lithium hydroxide solution, there is prepared 3-[4-[[2-(3-benzyl-ureido)-thiazol-4-ylcarbonyl]-amino]-phenyl]-glutaric acid; MS: 483 (M+H)⁺.

EXAMPLE 124

Analogously to Example 46, but using the aniline aniline compound prepared below and using 3-phenylglutaric acid anhydride in place of succinic acid anhydride, there is prepared rac-4-[3-[2-(N'-Benzyl-guanidino)-4-methyl-thiazol-5-yl]-phenyl-carbamoyl]-3-phenyl-butyric acid; MS: 528 (M+H)⁺.

Preparation of the aniline compound:

a) Analogously to Example 33b), but using the nitroolefin from Example 34ai) and using 2,4-dithiobiuret in place of 2-imino-4-thiobiuret, there is obtained [4-methyl-5-(3-nitro-phenyl)-thiazol-2-yl]-thiourea; MS: 294 (M+H)⁺.

b) 1.7 ml of methyl iodide are added to a suspension of 1.6 g of the thiourea obtained under a) in 32 ml of acetone and the mixture is boiled under reflux for 2 hours. Insoluble material is filtered off and the filtrate is evaporated to give 1.1 g of brown 2-methyl-1-[4-methyl-5-(3-nitro-phenyl)-thiazol-2-yl]-isothiourea hydroiodide (1:1); MS: 309 (M+H)⁺.

c) A solution of 1.1 g of the material obtained under b) in 7 ml of methanol is treated with 2.8 ml of benzylamine and boiled at reflux for 6 hours. The reaction mixture is evaporated and the residue is chromatographed on silica gel with hexane-ethyl acetate 1:1. There is isolated 0.23 g of orange N-benzyl-N'-[4-methyl-5-(3-nitro-phenyl)-thiazol-2-yl]-guanidine; MS: 368 (M+H)⁺.

d) The product obtained under c) is reduced analogously to Example 105ci) to N-[5-(3-amino-phenyl)-4-methyl-thiazol-2-yl]-N'-benzyl-guanidine; MS: 338 (M+H )⁺.

EXAMPLE 125

Analogously to Example 44, but using the acid component prepared below and using rac-glycyl-3-phenyl-beta-alanine ethyl ester hydrochloride in place of glycyl-beta-alanine ethyl ester hydrochloride, there is prepared ethyl rac-3-phenyl-3-[2-[[2-(pyridin-2-ylamino)-thiazol-4-ylcarbonyl]-amino]-acetylamino]-propionate; MS: 454 (M+H)⁺.

Preparation of the acid component:

a) Analogously to Example 1, but using pyridyl-thiourea in place of 2-imino-4-thiobiuret, there is obtained ethyl 2-(pyridin-2-ylamino)-thiazole-4-carboxylate; MS: 250 (M+H)⁺.

b) Analogously to Example 4, from the ester prepared above there is obtained 2-(pyridin-2-ylamino)-thiazole-4-carboxylic acid; MS: 222 (M+H)⁺.

EXAMPLE 126

Analogously to Example 45, from the ester of Example 125 there is obtained rac-3-phenyl-3-[2-[[2-(pyridin-2-ylamino)-thiazol-4-ylcarbonyl]-amino]-acetylamino]-propionic acid; MS: 426 (M+H)⁺.

EXAMPLE 127

In Analogy to the method given in Example 9a, from [[2-(3-benzyl-ureido)-thiazol-4-carbonyl]-amino]-acetic acid and ethyl rac-3-amino-3-pyridin-3-yl-propionate hydrochloride there is obtained ethyl rac-3-[2-[[2-(3-benzyl-ureido)-thiazol-4-carbonyl]-amino]-acetylamino]-3-pyridin-3-yl-propionate, m.p. 194° C., MS: 511 (M+H)⁺.

EXAMPLE 128

208 mg of ethyl rac-3-[2-[[2-(3-benzyl-ureido)-thiazole-4-carbonyl]-amino]-acetylamino]-3-pyridin-3-yl-propionate are stirred at RT for 12 hours in 4.2 ml of 25 percent hydrochloric acid. After evaporation of the hydrochloric acid in a vacuum the residue is taken up in water, neutralized with ammonia and purified on Kieselgel 100 (C18-reverse phase) with water-methanol (4:1). The pure fractions are combined and the residue is lyophilized from acetic acid. There are obtained 136 mg of rac-3-[2-[[2-(3-benzyl-ureido)-thiazole-4-carbonyl]-amino]-acetylamino]-3-pyridin-3-yl-propionic acid acetate (1:1), m.p. 177° C., MS: 483 (M+H)$^+$.

EXAMPLE 129

In Analogy to the method given in Example 9a, from [[2-(3-benzyl-ureido)-thiazole-4-carbonyl]-amino]-acetic acid and tert-butyl (S)-3-amino-N-benzyl-succinamate there is obtained tert-butyl (S)-N-benzyl-3-[2-[[2-(3-benzyl-ureido)-thiazole-4-carbonyl]-amino]-acetylamino]-succinamate, m.p. 123° C., MS: 595 (M+H)$^+$.

Preparation of the starting material:

a) Z-Aspartic acid 4-tert-butyl ester is coupled with benzylamine to tert-butyl (S)-N-benzyl-3-benzyloxycarbonylamino-succinamate, MS: 413 (M+H)$^+$.

b) By hydrogenation on Pd/C in ethanol there is obtained therefrom tert-butyl (S)-3-amino-N-benzyl-succinamate, MS: 279 (M+H)$^+$.

EXAMPLE 130

In analogy to Example 87, from tert-butyl (S)-N-benzyl-3-[2-[[2-(3-benzyl-ureido)-thiazole-4-carbonyl]-amino]-acetylamino]-succinamate there is obtained (S)-N-benzyl-3-[2-[[2-(3-benzyl-ureido)-thiazole-4-carbonyl]-amino]-acetylamino]-succinamic acid as the trifluoroacetate (1:0.4), m.p. 193° C., MS: 539 (M+H)$^+$.

EXAMPLE 131

In analogy to the method given in Example 9a, from 2-[[2-(3-benzyl-ureido)-thiazole-4-carbonyl]-amino]-acetic acid and ethyl 3-aminopropionate there is obtained ethyl 3-[2-[[2-(3-benzyl-ureido)-thiazole-4-carbonyl]-amino]-acetylamino]-propionate, m.p. 187° C., MS: 434 (M+H)$^+$.

EXAMPLE 132

236 mg of ethyl 3-[2-[[2-(3-benzyl-ureido)-thiazole-4-carbonyl]-amino]-acetylamino]-propionate are stirred in 4.7 ml of 25 percent hydrochloric acid and 4 ml of acetic acid for 24 hours at 20° C. The reaction mixture is evaporated in a vacuum and the residue is recrystallized from acetonitrile. There are obtained 213 mg of 3-[2-[[2-(3-benzyl-ureido)-thiazole-4-carbonyl]-amino]-acetylamino]-propionic acid as the hydrochloride (1:1), m.p. 174° C., MS: 406 (M+H)$^+$.

EXAMPLE 133

According to the same method as in Example 9a), from 2-[[2-(3-benzyl-ureido)-thiazole-4-carbonyl]-amino]-acetic acid and tert-butyl (S)-3-amino-N-(3-methoxy-phenyl)-succinamate there is obtained tert-butyl (S)-3-[2-[[2-(3-benzyl-ureido)-thiazole-4-carbonyl]-amino]-acetylamino]-N-(3-methoxy-phenyl)-succinamate, MS: 611 (M+H)$^+$.

The starting material can be prepared as follows:

a) By coupling Z-aspartic acid 4-tert-butyl ester with m-anisidine there is obtained tert-butyl (S)-3-benzyloxycarbonylamino-N-(3-methoxy-phenyl)-succinamate, m.p. 68–69° C., MS: 429 (M+H)$^+$.

b) Therefrom by hydrogenolysis on Pd/C in ethanol there is obtained tert-butyl (S)-3-amino-N-(3-methoxy-phenyl)-succinamate, MS: 295 (M+H)$^+$.

EXAMPLE 134

Analogously to Example 87, from tert-butyl (S)-3-[2-[[2-(3-benzyl-ureido)-thiazole-4-carbonyl]-amino]-acetylamino]-N-(3-methoxy-phenyl)-succinamate there is obtained (S)-3-[2-[[2-(3-benzyl-ureido)-thiazole-4-carbonyl]-amino]-acetylamino]-N-(3-methoxy-phenyl)-succinamic acid, m.p. 185° C., MS: 555 (M+H)$^+$.

EXAMPLE 135

According to the same method as in Example 9a), from tert-butyl 2-[[2-(3-benzyl-ureido)-thiazole-4-carbonyl]-amino]-acetic acid and tert-butyl (S)-2-(2-amino-3-tert-butoxycarbonyl-propionylamino)-benzoate there is obtained tert-butyl (S)-2-[2-[[2-(3-benzyl-ureido)-thiazole-4-carbonyl]-amino]-acetylamino]-3-tert-butoxycarbonyl-propionylamino]-benzoate, m.p. 116° C., MS: 681 (M+H)$^+$.

The starting material can be prepared as follows:

a) By coupling Z-aspartic acid 4-tert-butyl ester with tert-butyl anthranilate there is obtained tert-butyl (S)-2-(2-benzyloxycarbonylamino-3-tert-butoxycarbonyl-propionylamino)-benzoate, MS: 499 (M+H)$^+$.

b) By hydrogenolysis on Pd/C in ethanol there is obtained therefrom tert-butyl (S)-2-(2-amino-3-tert-butoxycarbonyl-propionylamino)-benzoate, m.p. 78° C., MS: 365 (M+H)$^+$.

EXAMPLE 136

567 mg of tert-butyl (S)-2-[2-[2-[[2-(3-benzyl-ureido)-thiazole-4-carbonyl]-amino]-acetylamino]-3-tert-butoxycarbonyl-propionylamino]-benzoate are stirred in 2.5 ml of methylene chloride and 2.5 ml of trifluoroacetic acid for 6 hours at RT. The solvent mixture is evaporated in a vacuum and the residue is taken up in water and extracted with chloroform. After drying with sodium sulphate the solution is evaporated. The residue is triturated in succession with ethyl acetate and water and then dried. There are obtained 307 mg of (S)-2-[2-(2-{[2-(3-benzyl-ureido)-thiazole-4-carbonyl]-amino}-acetylamino)-3-carboxy-propionylamino]-benzoic acid, m.p. 192° C. MS: 567 (M–H)$^+$.

EXAMPLE 137

Using the method described in Example 9a, from 2-(3-benzyl-ureido)-thiazole-4-carboxylic acid and methyl 6-aminohexanoate there is obtained methyl 6-{[2-(3-benzyl-ureido)-thiazole-4-carbonyl]-amino}-hexanoate, m.p. 140° C., MS: 405 (M+H)$^+$.

EXAMPLE 138

Analogously to Example 15, from methyl 6-{[2-(3-benzyl-ureido)-thiazole-4-carbonyl]-amino}-hexanoate by saponification with NaOH in MeOH there is obtained 6-{[2-(3-benzyl-ureido)-thiazole-4-carbonyl]-amino}-hexanoic acid, m.p. 178° C., MS: 391 (M+H)$^+$.

EXAMPLE 139

255 mg of HBTU are added to a suspension of 215 mg of 3-[(2-guanidino-4-methyl-thiazole-5-carbonyl)-amino]-benzoic acid in 2 ml of DMF and 0.15 ml of TEA. The mixture is stirred for one hour at RT, 177 mg of tert-butyl (S)-3-amino-N-phenyl-succinamate are added thereto and the resulting mixture is stirred for 25 hours at RT. The working up is effected as described in Example 5. After chromatography on silica gel with ethyl acetate-EtOH and methylene chloride-EtOH there are obtained 184 mg of tert-butyl (S)-3-[3-[(2-guanidino-4-methyl-thiazole-5-carbonyl)-amino]-benzoylamino]-N-phenyl-succinamate as a pale yellow foam, MS: 566 (M+H)$^+$.

The starting material can be obtained as follows:

a) According to the method just described, from ethyl 2-guanidino-4-methyl-thiazole-5-carboxylic acid and ethyl 3-aminobenzoate there is obtained ethyl 3-[(2-guanidino-4-methyl-thiazole-5-carbonyl)-amino]-benzoate, m.p. 149–152° C., MS: 348 (M+H)+.

b) By saponification with sodium hydroxide solution in EtOH there is obtained therefrom 3-[(2-guanidino-4-methyl-thiazole-5-carbonyl)-amino]-benzoic acid, m.p. 260° C.

EXAMPLE 140

184 mg of tert-butyl (S)-3-[3-[(2-guanidino-4-methyl-thiazol-5-carbonyl)-amino]-benzoylamino]-N-phenyl-succinamate are stirred in 1.3 ml of methylene chloride and 1.3 ml of TFA for 2.5 hours at RT. The solvent mixture is evaporated in a vacuum and the residue is dried in a vacuum. There are obtained 215 mg of (S)-3-[3-[(2-guanidino-4-methyl-thiazol-5-carbonyl)-amino]-benzoylamino]-N-phenyl-succinamic acid trifluoroacetate; MS: 510 (M+H)+.

EXAMPLE 141

Using the method given in Example 9a, from [[2-(3-benzyl-ureido)-thiazole-4-carbonyl]-amino]-acetic acid and H-Asp(OtBu)-Val-OtBu there is obtained tert-butyl (S)-2-[(S)-2-[2-[[2-(3-benzyl-ureido)-thiazole-4-carbonyl]-amino]-acetylamino]-3-tert-butoxycarbonyl-propionylamino]-3-methyl-butyrate, m.p. 108–110° C., MS: 661 (M+H)+.

EXAMPLE 142

In the same manner as described in Example 140 and lyophilization of the crude product from acetic acid, from tert-butyl (S)-2-[(S)-2-[2-[[2-(3-benzyl-ureido)-thiazole-4-carbonyl]-amino]-acetylamino]-3-tert-butoxycarbonyl-propionylamino]-3-methyl-butyrate there is obtained (S)-2-[(S)-2-(2-{[2-(3-benzyl-ureido)-thiazole-4-carbonyl]-amino}-acetylamino)-3-carboxy-propionylamino]-3-methyl-butyric acid as the acetate/trifluoroacetate, m.p. 93–98° C., MS: 549 (M+H)+.

EXAMPLE 143

Using the method given in Example 9a, from [[2-(3-benzyl-ureido)-thiazole-4-carbonyl]-amino]-acetic acid and tert-butyl (S)-3-amino-N-[(S)-tert-butoxycarbonyl-phenyl-methyl]-succinamate there is obtained tert-butyl (S)-3-[(S)-2-[[2-(3-benzyl-ureido)-thiazole-4-carbonyl]-amino]-acetylamino]-N-(tert-butoxycarbonyl-phenyl-methyl)-succinamate, MS: 695 (M+H)+.

EXAMPLE 144

In the same manner as described in Example 140 and lyophilization of the crude product from acetic acid, from tert-butyl (S)-3-[(S)-2-[[2-(3-benzyl-ureido)-thiazole-4-carbonyl]-amino]-acetylamino]-N-(tert-butoxycarbonyl-phenyl-methyl)-succinamate there is obtained (S)-3-[2-[[2-(3-benzyl-ureido)-thiazole-4-carbonyl]-amino]-acetyl-amino]-N-[(S)-carboxy-phenyl-methyl)-succinamic acid as the acetate/trifluoroacetate, m.p. 126–130° C., MS: 583 (M+H)+.

EXAMPLE 145

2-(3-Benzyl-ureido)-thiazole-4-carboxylic acid is coupled with N-Boc-lysine methyl ester acetate according to the method given in Example 9a to give methyl (S)-6-{[2-(3-benzyl-ureido)-thiazole-4-carbonyl]-amino}-2-tert-butoxycarbonylamino-hexanoate, m.p. 166° C., MS: 520 (M+H)+.

EXAMPLE 146

Analogously to Example 15, from methyl (S)-6-{[2-(3-benzyl-ureido)-thiazole-4-carbonyl]-amino}-2-tert-butoxycarbonylamino-hexanoate by saponification with NaOH in MeOH there is obtained (S)-6-{[2-(3-benzyl-ureido)-thiazole-4-carbonyl]-amino}-2-tert-butoxycarbonylamino-hexanoic acid, m.p. 138° C., MS: 506 (M+H)+.

EXAMPLE 147

2-(3-Benzyl-ureido)-thiazole-4-carboxylic acid is coupled with ethyl rac-6-amino-3-benzylcarbamoyl-hexanoate hydrochloride according to the method given in Example 9a to give ethyl rac-3-benzylcarbamoyl-6-{[2-(3-benzyl-ureido)-thiazole-4-carbonyl]-amino}-hexanoate, m.p. 128° C., MS: 552 (M+H)+.

The starting material can be obtained as follows:

a) tert-Butyl 2-oxo-piperidine-1-carboxylate is deprotonated in THF at −78° C. with lithium diisopropylamide and alkylated at −50° C. with tert-butyl bromoacetate. There is obtained tert-butyl rac-3-tert-butoxycarbonylmethyl-2-oxo-piperidine-1-carboxylate as a pale yellow oil, MS: 314 (M+H)+.

b) By heating to 80° C. with the equivalent amount of benzylamine there is obtained therefrom tert-butyl rac-3-benzylcarbamoyl-6-tert-butoxycarbonylamino-hexanoate, m.p. 119° C., MS: 420 (M)+.

c) This is firstly cleaved in methylene chloride with trifluoroacetic acid and then converted with hydrogen chloride in ethanol into ethyl rac-6-amino-3-benzylcarbamoyl-hexanoate hydrochloride (1:1), MS: 293 (M+H)+.

EXAMPLE 148

By saponification with sodium hydroxide solution in alcohol, from ethyl (RS)-3-benzylcarbamoyl-6-{[2-(3-benzyl-ureido)-thiazole-4-carbonyl]-amino}-hexanoate there is obtained rac-3-benzylcarbamoyl-6-{[2-(3-benzyl-ureido)-thiazole-4-carbonyl]-amino}-hexanoic acid, MS: 524 (M+H)+.

EXAMPLE 149

Using the method given in Example 9a, from 2-(3-pyridin-2-ylmethyl-ureido)-thiazole-4-carboxylic acid and ethyl 6-amino-5-oxo-hexanoate hydrochloride there is obtained ethyl 5-oxo-6-{[2-(3-pyridin-2-ylmethyl-ureido)-thiazole-4-carbonyl]-amino}-hexanoate, m.p. 110° C., MS: 434 (M+H)+.

The starting material can be prepared as follows: a) Ethyl 2-amino-thiazole-4-carboxylic acid hydrobromide is reacted with phenyl chloroformate in the presence of pyridine in THF to give ethyl 2-phenoxycarbonyl-amino-thiazole-4-carboxylate; m.p. 168° C., MS: 293 (M+H)+.

b) Therefrom with 2-aminomethylpyridine in DMSO at RT there is obtained ethyl 2-(3-pyridin-2-ylmethyl-ureido)-thiazole-4-carboxylate, m.p. 190° C., MS: 306 (M)+.

c) This is saponified with NaOH in EtOH to give 2-(3-pyridin-2-ylmethyl-ureido)-thiazole-4-carboxylic acid, m.p. 220° C., MS: 279 (M+H)+.

EXAMPLE 150

In the same manner as described in Example 6, from ethyl 5-oxo-6-{[2-(3-pyridin-2-ylmethyl-ureido)-thiazole-4-carbonyl]-amino}-hexanoate there is obtained 5-oxo-6-{[2-(3-pyridin-2-ylmethyl-ureido)-thiazole-4-carbonyl]-amino}-hexanoic acid as the hydrochloride (1:2), m.p. 199° C., MS: 406 (M+H)+.

EXAMPLE 151

Using the method described in Example 9a, from 4-[2-(3-benzyl-ureido)-thiazol-4-yl]-butyric acid and tert-butyl (S)-3-amino-N-benzyl-succinamate there is obtained tert-butyl (S)-N-benzyl-3-{4-[2-(3-benzyl-ureido)-thiazol-4-yl]-butyrylamino}-succinamate, MS: 580 (M+H)+.

The starting material is obtained as follows:

a) Ethyl 4-(2-amino-thiazol-4-yl)-butyrate hydrobromide is reacted with benzyl isocyanate in DMF in the presence of TEA to give ethyl 4-[2-(3-benzyl-ureido)-thiazol-4-yl]-butyrate; m.p. 157° C., MS: 347 (M)+, and b) this is saponified with NaOH in EtOH to give 4-[2-(3-benzyl-ureido)-thiazol-4-yl]-butyric acid, m.p. 191° C., MS: 318 (M−H)−.

EXAMPLE 152

281 mg of tert-butyl (S)-N-benzyl-3-{4-[2-(3-benzyl-ureido)-thiazol-4-yl]-butyrylamino}-succinamate are stirred in 2 ml of methylene chloride and 2 ml of trifluoroacetic acid for 2 hours at RT. After evaporation of the solvent in a vacuum there is obtained from ethyl acetate crystalline (S)-N-benzyl-3-{4-[2-(3-benzyl-ureido)-thiazol-4-yl]-butyrylamino}-succinamic acid trifluoroacetate (1:1), m.p. 159° C., MS: 524 (M+H)+.

EXAMPLE 153

Using the method described in Example 9a, from 2-(3-benzyl-ureido)-thiazole-4-carboxylic acid and ethyl 3-(4-amino-phenyl)-propionate there is obtained ethyl 3-[4-[[2-(3-benzyl-ureido)-thiazole-4-carbonyl]-amino]-phenyl]-propionate, m.p. 194° C., MS: 453 (M+H)+.

EXAMPLE 154

Analogously to Example 15, from ethyl 3-[4-[[2-(3-benzyl-ureido)-thiazole-4-carbonyl]-amino]-phenyl]-propionate there is obtained 3-[4-[[2-(3-benzyl-ureido)-thiazole-4-carbonyl]-amino]-phenyl]-propionic acid, m.p. 233° C., MS: 425 (M+H)+.

EXAMPLE 155

According to the method given in Example 9a, 2-(3-benzyl-ureido)-thiazole-4-carboxylic acid is coupled with diethyl rac-2-(3-amino-2-oxo-propyl)-succinate to give diethyl rac-2-[3-[[2-(3-benzyl-ureido)-thiazole-4-carbonyl]-amino]-2-oxo-propyl]-succinate, m.p. 126–129° C., MS: 505 (M+H)+.

Preparation of the starting material:

a) By brominating acetonylsuccinic acid in ethanol at 50° C. there is obtained diethyl (RS)-2-(3-bromo-2-oxo-propyl)-succinate, MS: 309 (M+H)+.

b) This is reacted with sodium azide in DMSO to give diethyl (RS)-2-(3-azido-2-oxo-propyl)-succinate, MS: 226 (M−OEt)+.

c) By catalytic hydrogenation on Pd/C in EtOH in the presence of hydrogen chloride there is obtained therefrom the hydrochloride of diethyl (RS)-2-(3-amino-2-oxo-propyl)-succinate.

EXAMPLE 156

In analogy to Example 15, from diethyl (RS)-2-[3-[[2-(3-benzyl-ureido)-thiazole-4-carbonyl]-amino]-2-oxo-propyl]-succinate there is obtained (RS)-2-[3-[[2-(3-benzyl-ureido)-thiazole-4-carbonyl]-amino]-2-oxo-propyl]-succinic acid, MS: 447 (M−H)+.

EXAMPLE 157

According to the method given in Example 9a, [[2-(3-benzyl-ureido)-thiazole-4-carbonyl]-amino]-acetic acid is coupled with (S)-aspartic acid di-tert-butyl ester to give di-tert-butyl (S)-2-(2-{[2-(3-benzyl-ureido)-thiazole-4-carbonyl]-amino}-acetylamino)-succinate, m.p. 111–114° C., MS: 562 (M+H)+.

EXAMPLE 158

In analogy to Example 87 and crystallization from acetic acid, from di-tert-butyl (S)-2-(2-{[2-(3-benzyl-ureido)-thiazole-4-carbonyl]-amino}-acetylamino)-succinate there is obtained die (S)-2-(2-{[2-(3-benzyl-ureido)-thiazole-4-carbonyl]-amino}-acetylamino)-succinic acid as the trifluoroacetate (1:0.9), m.p. 183° C., MS: 450 (M+H)+.

EXAMPLE 159

According to the method given in Example 9a, [[2-(3-benzyl-ureido)-thiazole-4-carbonyl]-amino]-acetic acid is coupled with tert-butyl (S)-3-amino-N-isobutyl-succinamate to9 give tert-butyl (S)-3-[2-[[2-(3-benzyl-ureido)-thiazole-4-carbonyl]-amino]-acetylamino]-N-isobutyl-succinamate, MS: 561 (M+H)+.

EXAMPLE 160

In analogy to Example 87 and lyophilization from acetic acid, from tert-butyl (S)-3-[2-[[2-(3-benzyl-ureido)-thiazole-4-carbonyl]-amino]-acetylamino]-N-isobutyl-succinamate there is obtained (S)-3-[2-[[2-(3-benzyl-ureido)-thiazole-4-carbonyl]-amino]-acetylamino]-N-isobutyl-succinamate as the trifluoroacetate (1:0.3), MS: 505 (M+H)+.

EXAMPLE 161

According to the method given in Example 9a, [[2-(3-benzyl-ureido)-thiazole-4-carbonyl]-amino]-acetic acid is coupled with tert-butyl (S)-3-amino-N-pyridin-2-ylmethyl-succinamate to give tert-butyl (S)-3-[2-[[2-(3-benzyl-ureido)-thiazole-4-carbonyl]-amino]-acetylamino]-N-pyridin-2-ylmethyl-succinamate, m.p 108° C., MS: 596 (M+H)+.

The tert-butyl (S)-3-amino-N-pyridin-2-ylmethyl-succinamate is prepared as follows:

a) Z-Aspartic acid 4-tert-butyl ester is coupled with 2-aminomethylpyridine to give tert-butyl (S)-3-benzyloxycarbonylamino-N-pyridin-2-ylmethyl-succinamate, MS: 414 (M+H)+, and b) the latter is converted by catalytic hydrogenation into tert-butyl (S)-3-amino-N-pyridin-2-ylmethyl-succinamate; MS: 280 (M+H)+.

EXAMPLE 162

200 mg of tert-butyl (S)-3-[2-[[2-(3-benzyl-ureido)-thiazole-4-carbonyl]-amino]-acetylamino]-N-pyridin-2-ylmethyl-succinamate are stirred in 2 ml of methylene chloride and 2 ml of trifluoroacetic acid for 2 hours at RT. After evaporation of the solvent in a vacuum there is obtained from ethyl acetate crystalline (S)-3-[2-[[2-(3-benzyl-ureido)-thiazole-4-carbonyl]-amino]-acetylamino]-N-pyridin-2-ylmethyl-succinamic acid trifluoroacetate (1:1.16), m.p. 114° C., MS: 540 (M+H)+.

EXAMPLE 163

According to the method given in Example 9a, [[2-(3-benzyl-ureido)-thiazole-4-carbonyl]-amino]-acetic acid is coupled with tert-butyl (S)-3-amino-N-pyridin-3-ylmethyl-succinamate to give tert-butyl (S)-3-[2-[[2-(3-benzyl-ureido)-thiazole-4-carbonyl]-amino]-acetylamino]-N-pyridin-3-ylmethyl-succinamate, m.p 185° C., MS: 596 (M+H)+.

The tert-butyl (S)-3-amino-N-pyridin-3-ylmethyl-succinamate is prepared as follows:

a) Z-Aspartic acid 4-tert-butyl ester is coupled with 3-aminomethylpyridine to give tert-butyl (S)-3-benzyloxycarbonylamino-N-pyridin-3-ylmethyl-succinamate, MS: 414 (M+H)+, and b) the latter is converted by catalytic hydrogenation into tert-butyl (S)-3-amino-N-pyridin-3-ylmethyl-succinamate; MS: 280 (M+H)+.

EXAMPLE 164

In the same manner as described in Example 162, from tert-butyl (S)-3-[2-[[2-(3-benzyl-ureido)-thiazole-4-carbonyl]-amino]-acetylamino]-N-pyridin-3-ylmethyl-succinamate there is obtained (S)-3-[2-[[2-(3-benzyl-ureido)-thiazole-4-carbonyl]-amino]-acetylamino]-N-pyridin-3-ylmethyl-succinamic acid as the trifluoroacetate (1:1.2), m.p. 135° C., MS: 540 (M+H)+.

EXAMPLE 165

277 mg of 2-(3-benzyl-ureido)-thiazole-4-carboxylic acid, 175 mg of CDMT, 3 ml of THF and 0.12 ml of N-MM are stirred for 4½ hours at RT, treated with 280 mg of 3-(p-aminophenyl)-N-(tert-butoxycarbonyl)-L-alanine and 0.12 ml of N-MM and stirred for a further 20 hours at RT. For the working up, the mixture is diluted with ethyl acetate, washed with 0.1N hydrochloric acid and water, dried over sodium sulphate and evaporated in a vacuum. Chromatography on silica gel with ethyl acetate-acetic acid 99:1 and trituration in ethyl acetate gives 111 mg of (S)-3-[4-[[2-(3-benzyl-ureido)-thiazole-4-carbonyl]-amino]-phenyl]-2-tert-butoxycarbonylamino-propionic acid, m.p. 231° C., MS: 540 (M+H)+.

EXAMPLE 166

Similarly, from 2-(3-benzyl-ureido)-thiazole-4-carboxylic acid and 3-(p-amino-phenyl)-N-(tert-butoxycarbonyl)-D-alanine there is obtained (R)-3-[4-[[2-(3-benzyl-ureido)-thiazole-4-carbonyl]-amino]-phenyl]-2-tert-butoxycarbonylamino-propionic acid, m.p. 232° C., MS: 540 (M+H)+.

EXAMPLE 167

According to the method given in Example 9a, 2-(3-pyridin-2-ylmethyl-ureido)-thiazole-4-carboxylic acid is coupled with tert-butyl (S)-3-(2-amino-acetylamino)-N-pyridin-2-ylmethyl-succinamate. For the working up, the mixture is diluted with ethyl acetate, washed with dilute sodium carbonate solution and water, dried and evaporated. Chromatography on silica gel with methylene chloride-ethanol gives tert-butyl (S)-N-pyridin-2-ylmethyl-3-(2-{[2-(3-pyridin-2-ylmethyl-ureido)-thiazole-4-carbonyl]-amino}-acetylamino)-succinamate, m.p. 112° C., MS: 597 (M+H)+.

The starting material can be prepared as follows:

a) By coupling Z-glycine with tert-butyl (S)-3-amino-N-pyridin-2-ylmethyl-succinamate there is obtained tert-butyl (S)-3-(2-benzyloxycarbonylamino-acetylamino)-N-pyridin-2-ylmethyl-succinamate, MS: 471 (M+H)+.

b) This is hydrogenated on Pd/C in alcohol to give tert-butyl (S)-3-(2-amino-acetyl-amino)-N-pyridin-2-ylmethyl-succinamate; MS: 337 (M+H)+.

EXAMPLE 168

394 mg of tert-butyl (S)-N-pyridin-2-ylmethyl-3-(2-{[2-(3-pyridin-2-ylmethyl-ureido)-thiazole-4-carbonyl]-amino}-acetylamino)-succinamate are stirred in 1.5 ml of methylene chloride and 1.5 ml of TFA for 4 hours at RT. The solvents are evaporated in a vacuum, the residue is taken up in ethyl acetate and the solution is again evaporated. Then, the residue is dissolved in water, neutralized with ammonia and evaporated in a vacuum. The residue is taken up in ethanol and, after trituration, suction filtration and drying, there are obtained 254 mg of (S)-N-pyridin-2-ylmethyl-3-(2-{[2-(3-pyridin-2-ylmethyl-ureido)-thiazole-4-carbonyl]-amino}-acetylamino)-succinamic acid, m.p. 164° C., MS: 541 (M+H)+.

EXAMPLE 169

According to the method given in Example 9a, 2-(3-benzyl-ureido)-thiazole-4-carboxylic acid is reacted with tert-butyl N-(3-aminobenzoyl)-beta-alanine tert-butyl ester to give tert-butyl 3-(3-{[2-(3-benzyl-ureido)-thiazole-4-carbonyl]-amino}-benzoylamino)-propionate. M.p. 212° C., MS: 524 (M+H)+.

EXAMPLE 170

363 mg of tert-butyl 3-(3-{[2-(3-benzyl-ureido)-thiazole-4-carbonyl]-amino}-benzoylamino)-propionate are stirred in 1.5 ml of methylene chloride and 1.5 ml of TFA for 4 hours at RT. After evaporation of the solution in a vacuum the residue is diluted with ethyl acetate, washed with water, dried and evaporated in a vacuum. From acetone there are obtained 145 mg of 3-(3-{[2-(3-benzyl-ureido)-thiazole-4-carbonyl]-amino}-benzoylamino)-propionic acid, m.p. 157° C., MS: 468 (M+H)+.

EXAMPLE 171

In analogy to Example 18, 2-(imidazolidin-2-ylidenamino)-thiazole-4-carboxylic acid is reacted with ethyl 3-(2-amino-acetylamino)-3-pyridin-3-yl-propionate hydrochloride. After chromatography on silica gel with ethyl acetate-ethanol and trituration in ether there is obtained ethyl (RS)-3-(2-{[2-(imidazolidin-2-ylidenamino)-thiazole-4-carbonyl]-amino}-acetylamino)-3-pyridin-3-yl-propionate, m.p. 198–199° C., MS: 446 (M+H)+.

The starting materials are prepared as follows:

a) Imidazolidin-2-ylidene-thiourea is reacted in EtOH with ethyl bromopyruvate to give ethyl 2-(imidazolidin-2-ylideneamino)-thiazole-4-carboxylate hydrobromide. M.p. 207° C., MS: 241 (M+H)+.

b) By saponification with sodium hydroxide solution in ethanol there is obtained therefrom 2-(imidazolidin-2-ylideneamino)-thiazole-4-carboxylic acid, m.p. 260° C., MS: 212 (M)+.

c) Z-Glycine is coupled with ethyl (RS)-3-amino-3-pyridin-3-yl-propionate hydrochloride to give ethyl rac-3-(2-benzyloxycarbonylamino-acetylamino)-3-pyridin-3-yl-propionate; MS: 386 (M+H)+.

d) By catalytic hydrogenation on Pd/C in ethanol in the presence of hydrogen chloride there is obtained therefrom ethyl 3-(2-amino-acetylamino)-3-pyridin-3-yl-propionate as the hyrochloride, MS: 252 (M+H)+.

EXAMPLE 172

213 mg of ethyl rac-3-(2-{[2-(imidazolidin-2-ylidenamino)-thiazole-4-carbonyl]-amino}-acetylamino)-3-pyridin-3-yl-propionate are stirred for 10 hours at RT in 4 ml of 25% hydrochloric acid. The reaction mixture is evaporated to dryness in a vacuum and the residue is lyophilized from acetic acid. There are obtained 241 mg of 3-(2-{[2-(imidazolidin-2-ylideneamino)-thiazole-4-carbonyl]-amino}-acetylamino)-3-pyridin-3-yl-propionic acid hydrochloride (1:2), m.p. 170–172° C., MS: 418 (M+H)+.

EXAMPLE 173

In analogy to Example 18, 4-methyl-2-(tetrahydro-pyrimidin-2-ylideneamino)-thiazole-5-carboxylic acid is reacted with ethyl rac-7-amino-3-phenyl-heptanoate. After chromatography on silica gel with ethyl acetate-alcohol and crystallization from alcohol there is obtained ethyl rac-7-[[4-methyl-2-(tetrahydro-pyrimidin-2-ylideneamino)-thiazole-5-carbonyl]-amino]-3-phenyl-heptanoate, m.p. 137–139° C., MS: 472 (M+H)⁺.

The starting material can be prepared as follows:

a) (Tetrahydro-pyrimidin-2-ylidene)-thiourea is reacted in alcohol at 78° C. with ethyl chloroacetoacetate to give ethyl 4-methyl-2-(tetrahydro-pyrimidin-2-ylideneamino)-thiazole-5-carboxylate hydrochloride (1:1). M.p. 224° C., MS: 269 (M+H)⁺.

b) By saponification with sodium hydroxide solution in ethanol there is obtained therefrom 4-methyl-2-(tetrahydro-pyrimidin-2-ylideneamino)-thiazole-5-carboxylic acid, m.p. 198° C., MS: 241 (M+H)⁺.

EXAMPLE 174

437 mg of ethyl rac-7-[[4-methyl-2-(tetrahydro-pyrimidin-2-ylideneamino)-thiazole-5-carbonyl]-amino]-3-phenyl-heptanoate are stirred for 22 hours at RT in 9 ml of 25% hydrochloric acid. The reaction mixture is evaporated to dryness in a vacuum and the residue is lyophilized from acetic acid. There are obtained 457 mg of rac-7-[[4-methyl-2-(tetrahydro-pyrimidin-2-ylideneamino)-thiazole-5-carbonyl]-amino]-3-phenyl-heptanoic acid hydrochloride acetate, m.p. 60–63° C., MS: 444 (M+H)⁺.

EXAMPLE A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

EXAMPLE B

A compound of formula I can be used in a known manner as the active ingredient for the production of capsules of the following composition:

| Per capsule | |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

| List of common abbreviations | |
| --- | --- |
| AcOEt | Ethyl acetate |
| AcOH | Acetic acid |
| Aeg-RGDS | Aminoethylglycine-Arg-Gly-Asp-Ser-OH |
| Boc | tert-Butoxycarbonyl |
| BOP | (Benzotriazol-1-yloxy)-tris-(dimethylamino)-phosphonium hexafluorophosphate |
| BSA | Bovine serum albumin |
| Cbz | Benzyloxycarbonyl |
| CDMT | 2-Chloro-4,6-dimethoxy-1,3,5-triazine |
| DMF | Dimethylformamide |
| EDC | N-(3-Dimethylaminopropyl)-N'-ethyl-carbodiimide hydrochloride |
| EI | electron impact |
| ELISA | Enzyme-linked immunosorbent assay |
| EtOH | Ethanol |
| FAB | fast atom bombardment |
| HBTU | O-(Benzotriazol-1-yl)-N,N,N',N'-tetramethyluronium hexafluorophosphate |
| ISP | ion spray (positively charged ions) |
| MeCN | Acetonitrile |
| MeOH | Methanol |
| MS | Mass spectroscopy |
| NMM | N-Methylmorpholine |
| RGDS | H-Arg-Gly-Asp-Ser-OH |
| RP | reverse phase |
| RT | Room temperature |
| Smp | Melting point |
| t-BuOH | tert-Butanol |
| TFA | Trifluoroacetic acid |
| THF | Tetrahydrofuran |

Upon reading, the present specification, various alternative embodiments will become obvious to the skilled artisan. These embodiments are to be considered within the scope and spirit of the subject invention that is only to be limited by the claims that follow and their equivalents.

What is claimed is:

1. A compound having the formula:

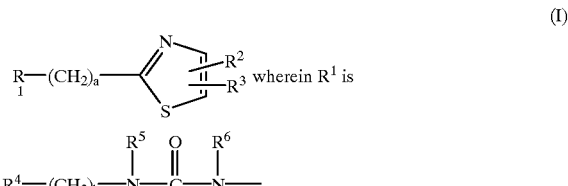

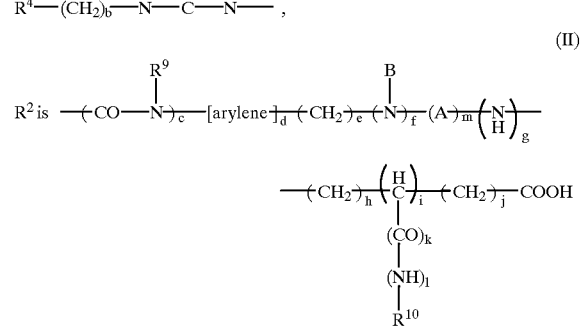

$R^3$ is hydrogen, alkyl, cycloalkyl, aryl, aralkyl, heteroaryl, carboxy, alkyl-O—CO—, or aralkyl-O—CO—;

$R^4$ is hydrogen, alkyl, cycloalkyl, aryl, or heteroaryl;

$R^5$ and $R^6$ are each independently hydrogen, alkyl, cycloalkyl, or heteroaryl;

$R^9$ is hydrogen, alkyl, or cycloalkyl;

$R^{10}$ is aryl, aralkyl, heterocyclyl, heterocyclylalkyl, hydroxy, hydrogen, or alkyl, or $R^{10}$ is carboxy, carboxyalkyl, alkyl-O—CO—, aralkyl-O—CO—, alkyl-CO—, aralkyl-CO—, heteroarylalkyl-CO—, alkylsulphonyl, arylsulphonyl or heteroarylsulphonyl and k is zero, or $R^{10}$ is an α-amino acid bonded via the amino group and l is zero and k is 1;

A is carbonyl or sulphonyl;

B is hydrogen, alkyl, or cycloalkyl;

a is an integer from 0 to 2 but not being zero when $R^1$ is —$NH_2$; b is an integer from 0 to 4; c, d, f, g, k, l and m are each independently an integer from 0 to 1, whereby c, f and g are not simultaneously 0 and whereby m is not 0 when f or g is 1; i is an integer from 0 to 1, whereby k and l are also 0 when i is 0; e is an integer from 0 to 3; h is an integer from 0 to 5; j is an integer from 0 to 2; and the sum of e, h and j is an integer from 2 to 7;

and the pharmaceutically usable salts and esters thereof.

2. The compound in accordance with claim 1, wherein $R^4$ is hydrogen, alkyl, cycloalkyl, phenyl, or pyridyl.

3. The compound in accordance with claim 1, wherein $R^5$ and $R^6$ are hydrogen or pyridyl.

4. The compound in accordance with claim 1, wherein the compound of formula I is a compound having the formula:

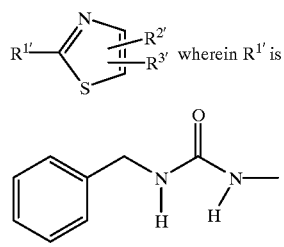

Ia wherein $R^{1'}$ is

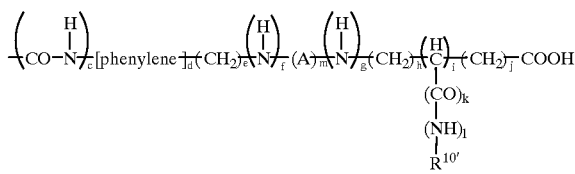

$R^{2'}$ is

IIa

A is carbonyl or sulphonyl;

c, d, f, g, k, l and m are each independently an integer from 0 to 1, whereby c, f and g are not simultaneously 0 and whereby m is not 0 when f or g is 1; i is an integer from 0 to 1, whereby k and l are also 0 when i is 0; e is an integer from 0 to 3; h is an integer from 0 to 5; j is an integer from 0 to 2; and the sum of e, h and j is an integer from 2 to 7; and $R^{10'}$ is phenyl; phenyl substituted with halogen, hydroxy, or alkoxy; carboxy; carboxy alkyl, alkyl, or pyridine; $R^{3'}$ is hydrogen or alkyl.

5. The compound in accordance with claim 4, wherein $R^{3'}$ is hydrogen.

6. The compound in accordance with claim 5, wherein $R^{10'}$ is phenyl.

7. The compound in accordance with claim 6, wherein the compound of formula Ia is rac 3-[2-[[(2-(3-benzyl-ureido)-thiazol-4-ylcarbonyl]-amino]-acetylamino]-3-phenyl-propionic acid.

8. The compound in accordance with claim 6, wherein the compound of formula Ia is (S)-3-(2-{[2-(3-benzyl-ureido)-thiazole-4-carbonyl]-amino}-acetylamino)-succinic acid 4-anilide.

9. The compound in accordance with claim 5, wherein $R^{10'}$ is alkyl.

10. The compound in accordance with claim 9, wherein the compound of formula Ia is (S)-2-[(S)-2-(2-{[2-(3-benzyl-ureido)-thiazole-4-carbonyl]-amino}-acetylamino)-3-carboxy-propionylamino]-3-methyl-butyric acid acetate/trifluoroacetate.

11. The compound in accordance with claim 5, wherein $R^{10'}$ is pyridine.

12. The compound in accordance with claim 11, wherein the compound of formula Ia is (S)-3-[2-[[2-(3-benzyl-ureido)-thiazole-4-carbonyl]-amino]-acetylamino]-N-pyridin-2-ylmethyl-succinamic acid trifluoroacetate.

13. The compound in accordance with claim 1, wherein the compound of formula I is 6-{[2-(3-benzyl-ureido)-thiazole-4-carbonyl]-amino}-5-oxo-hexanoic acid.

14. The compound in accordance with claim 1, wherein the compound of formula I is (S)-N-benzyl-3-[2-[[2-(3-benzyl-ureido)-thiazole-4-carbonyl]-amino]-acetylamino]-succinamic acid trifluoroacetate.

15. The compound in accordance with claim 1, wherein the compound of formula I is (S)-3-[2-[[2-(3-benzyl-ureido)-thiazole-4-carbonyl]-amino]-acetylamino]-N-isobutyl-succinamic acid trifluoroacetate.

16. The compound in accordance with claim 1, wherein the compound of formula I is ethyl rac-6-{[2-(3-benzyl-ureido)-thiazole-4-carbonyl]-amino}-3-phenyl-hexanoate.

17. The compound in accordance with claim 1, wherein the compound of formula I is rac-6-{[2-(3-benzyl-ureido)-thiazole-4-carbonyl]-amino}-3-phenyl-hexanoic acid.

18. The compound in accordance with claim 1, wherein the compound of formula I is ethyl rac 3-[2-[[(2-(3-benzyl-ureido)-thiazol-4-ylcarbonyl]-amino]-acetylamino]-3-phenyl-propionate.

19. The compound in accordance with claim 1, wherein the compound of formula I is ethyl rac 3-[3-[[4-methyl-2-(3-methyl-ureido)-thiazol-5-ylcarbonyl]-amino]-benzoylamino]-3-pyridin-3-yl-propionate.

20. The compound in accordance with claim 1, wherein the compound of formula I is rac 3-[3-[[4-methyl-2-(3-methyl-ureido)-thiazol-5-ylcarbonyl]-amino]-benzoylamino]-3-pyridin-3-yl-propionic acid.

21. The compound in accordance with claim 1, wherein the compound of formula I is ethyl rac-7-{[2-(3-benzyl-ureido)-4-methyl-thiazole-5-carbonyl]-amino}-3-phenyl-heptanoate.

22. The compound in accordance with claim 1, wherein the compound of formula I is rac-7-{[2-(3-benzyl-ureido)-4-methyl-thiazole-5-carbonyl]-amino}-3-phenyl-heptanoic acid.

23. The compound in accordance with claim 1, wherein the compound of formula I is ethyl 6-{[2-(3-benzyl-ureido)-thiazole-4-carbonyl]-amino}-5-oxo-hexanoate.

24. The compound in accordance with claim 1, wherein the compound of formula I is (S)-3-(2-{[2-(3-benzyl-ureido)-thiazole-4-carbonyl]-amino}-acetylamino)-succinic acid 4-anilide.

25. The compound in accordance with claim 1, wherein the compound of formula I is rac 4-{3-[2-(3-benzyl-ureido)-4-methyl-thiazol-5-yl]-phenylcarbamoyl}-3-phenyl-butyric acid.

26. The compound in accordance with claim 1, wherein the compound of formula I is ethyl rac-3-[2-[[2-(3-benzyl-ureido)-5-methyl-thiazol-4-ylcarbonyl]-amino]-acetylamino]-3-phenyl-propionate.

27. The compound in accordance with claim 1, wherein the compound of formula I is ethyl rac-3-[2-[[2-(3-benzyl-ureido)-5-phenyl-thiazol-4-ylcarbonyl]-amino]-acetylamino]-3-phenyl-propionate.

28. The compound in accordance with claim 1, wherein the compound of formula I is rac-3-[2-[[2-(3-benzyl-ureido)-5-methyl-thiazol-4-ylcarbony]-amino]-acetylamino]-3-phenyl-propionic acid.

29. The compound in accordance with claim 1, wherein the compound of formula I is rac-3-[2-[[2-(3-benzyl-ureido)-5-phenyl-thiazol-4-ylcarbonyl]-amino]-acetylamino]-3-phenyl-propionic acid.

30. The compound in accordance with claim 1, wherein the compound of formula I is rac-4-[3-[2-(3-benzyl-ureido)-5-methyl-thiazol-4-yl]-phenylcarbamoyl]-3-phenyl-butyric acid.

31. The compound in accordance with claim 1, wherein the compound of formula I is rac-4-[[3-[2-(3-benzyl-ureido)-5-methyl-thiazol-4-yl]-phenyl]-methyl-carbamoyl]-3-phenyl-butyric acid.

32. The compound in accordance with claim 1, wherein the compound of formula I is ethyl rac-3-phenyl-3-[2-[[2-(3-phenyl-ureido)-thiazol-4-ylcarbonyl]-amino]-acetylamino]-propionate.

33. The compound in accordance with claim 1, wherein the compound of formula I is ethyl rac-3-[2-[[2-(3-phenethyl-ureido)-thiazol-4-ylcarbonyl]-amino]-acetylamino]-3-phenyl-propionate.

34. The compound in accordance with claim 1, wherein the compound of formula I is ethyl rac-3-(2-[[2-(3-butyl-ureido)-thiazol-4-ylcarbonyl]-amino]-acetylamino)-3-phenyl-propionate.

35. The compound in accordance with claim 1, wherein the compound of formula I is rac-3-phenyl-3-[2-[[2-(3-phenyl-ureido)-thiazol-4-ylcarbonyl]-amino]-acetylamino]-propionic acid.

36. The compound in accordance with claim 1, wherein the compound of formula I is rac-3-[2-[[2-(3-phenethyl-ureido)-thiazol-4-ylcarbonyl]-amino]-acetylamino]-3-phenyl-propionic acid.

37. The compound in accordance with claim 1, wherein the compound of formula I is rac-3-(2-[[2-(3-butyl-ureido)-thiazol-4-ylcarbonyl]-amino]-acetylamino)-3-phenyl-propionic acid.

38. The compound in accordance with claim 1, wherein the compound of formula I is ethyl rac-3-[4-[[2-(3-benzyl-ureido)-thiazol-4-ylcarbonyl]-amino]-phenyl]-3-tert-butoxycarbonylamino-propionate.

39. The compound in accordance with claim 1, wherein the compound of formula I is rac-3-[4-[[2-(3-benzyl-ureido)-thiazol-4-ylcarbonyl]-amino]-phenyl]-3-tert-butoxycarbonylamino-propionic acid.

40. The compound in accordance with claim 1, wherein the compound of formula I is rac-3-amino-3-[4-[[2-(3-benzyl-ureido)-thiazol-4-ylcarbonyl]-amino]-phenyl]-propionic acid.

41. The compound in accordance with claim 1, wherein the compound of formula I is ethyl rac-3-[4-[[2-(3-benzyl-ureido)-thiazol-4-ylcarbonyl]-amino]-phenyl]-3-propionylamino-propionate.

42. The compound in accordance with claim 1, wherein the compound of formula I is ethyl rac-3-[4-[[2-(3-benzyl-ureido)-thiazol-4-ylcarbonyl]-amino]-phenyl]-3-butylsulphonylamino-propionate.

43. The compound in accordance with claim 1, wherein the compound of formula I is rac-3-[4-[[2-(3-benzyl-ureido)-thiazol-4-ylcarbonyl]-amino]-phenyl]-3-propionylamino-propionic acid.

44. The compound in accordance with claim 1, wherein the compound of formula I is rac-3-[4-[[2-(3-benzyl-ureido)-thiazol-4-ylcarbonyl]-amino]-phenyl]-3-butylsulphonylamino-propionic acid.

45. The compound in accordance with claim 1, wherein the compound of formula I is diethyl 3-[4-[[2-(3-benzyl-ureido)-thiazol-4-ylcarbonyl]-amino]-phenyl]-glutarate.

46. The compound in accordance with claim 1, wherein the compound of formula I is 3-[4-[[2-(3-benzyl-ureido)-thiazol-4-ylcarbonyl]-amino]-phenyl]-glutaric acid.

47. The compound in accordance with claim 1, wherein the compound of formula I is ethyl rac-3-[2-[[2-(3-benzyl-ureido)-thiazole-4-carbonyl]-amino]-acetylamino]-3-pyridin-3-yl-propionate.

48. The compound in accordance with claim 1, wherein the compound of formula I is rac-3-[2-[[2-(3-benzyl-ureido)-thiazole-4-carbonyl]-amino]-acetylamino]-3-pyridin-3-yl-propionic acid acetate.

49. The compound in accordance with claim 1, wherein the compound of formula I is tert-butyl (S)-N-benzyl-3-[2-[[2-(3-benzyl-ureido)-thiazole-4-carbonyl]-amino]-acetylamino]-succinamate.

50. The compound in accordance with claim 1, wherein the compound of formula I is ethyl 3-[2-[[2-(3-benzyl-ureido)-thiazole-4-carbonyl]-amino]-acetylamino]-propionate.

51. The compound in accordance with claim 1, wherein the compound of formula I is 3-[2-[[2-(3-benzyl-ureido)-thiazole-4-carbonyl]-amino]-acetylamino]-propionic acid hydrochloride.

52. The compound in accordance with claim 1, wherein the compound of formula I is tert-butyl (S)-3-[2-[[2-(3-benzyl-ureido)-thiazole-4-carbonyl]-amino]-acetylamino]-N-(3-methoxy-phenyl)-succinamate.

53. The compound in accordance with claim 1, wherein the compound of formula I is (S)-3-[2-[[2-(3-benzyl-ureido)-thiazole-4-carbonyl]-amino]-acetylamino]-N-(3-methoxy-phenyl)-succinamic acid.

54. The compound in accordance with claim 1, wherein the compound of formula I is tert-butyl (S)-2-[2-[2-[[2-(3-benzyl-ureido)-thiazole-4-carbonyl]-amino]-acetylamino]-3-tert-butoxycarbonyl-propionylamino]-benzoate.

55. The compound in accordance with claim 1, wherein the compound of formula I is (S)-2-[2-(2-{[2-(3-benzyl-ureido)-thiazole-4-carbonyl]-amino}-acetylamino)-3-carboxy-propionylamino]-benzoic acid.

56. The compound in accordance with claim 1, wherein the compound of formula I is methyl 6-{[2-(3-benzyl-ureido)-thiazole-4-carbonyl]-amino}-hexanoate.

57. The compound in accordance with claim 1, wherein the compound of formula I is 6-{[2-(3-benzyl-ureido)-thiazole-4-carbonyl]-amino}-hexanoic acid.

58. The compound in accordance with claim 1, wherein the compound of formula I is tert-butyl (S)-2-[(S)-2-[2-[[2-(3-benzyl-ureido)-thiazole-4-carbonyl]-amino]-acetylamino]-3-tert-butoxycarbonyl-propionylamino]-3-methyl-butyrate.

59. The compound in accordance with claim 1, wherein the compound of formula I is tert-butyl (S)-3-[(S)-2-[[2-(3-benzyl-ureido)-thiazole-4-carbonyl]-amino]-acetylamino]-N-(tert-butoxycarbonyl-phenyl-methyl)-succinamate.

60. The compound in accordance with claim 1, wherein the compound of formula I is (S)-3-[2-[[2-(3-benzyl-ureido)-thiazole-4-carbonyl]-amino]-acetylamino]-N-[(S)-carboxy-phenyl-methyl)-succinamic acid acetate/trifluoroacetate.

61. The compound in accordance with claim 1, wherein the compound of formula I is methyl (S)-6-{[2-(3-benzyl-ureido)-thiazole-4-carbonyl]-amino}-2-tert-butoxycarbonylamino-hexanoate.

62. The compound in accordance with claim 1, wherein the compound of formula I is (S)-6-{[2-(3-benzyl-ureido)-thiazole-4-carbonyl]-amino}-2-tert-butoxycarbonylamino-hexanoic acid.

63. The compound in accordance with claim 1, wherein the compound of formula I is ethyl rac-3-benzylcarbamoyl-6-{[2-(3-benzyl-ureido)-thiazole-4-carbonyl]-amino}-hexanoate.

64. The compound in accordance with claim 1, wherein the compound of formula I is rac-3-benzylcarbamoyl-6-{[2-(3-benzyl-ureido)-thiazole-4-carbonyl]-amino}-hexanoic acid.

65. The compound in accordance with claim 1, wherein the compound of formula I is ethyl 5-oxo-6-{[2-(3-pyridin-2-ylmethyl-ureido)-thiazole-4-carbonyl]-amino}-hexnoate.

66. The compound in accordance with claim 1, wherein the compound of formula I is 5-oxo-6-{[2-(3-pyridin-2-ylmethyl-ureido)-thiazole-4-carbonyl]-amino}-hexanoic acid hydrochloride.

67. The compound in accordance with claim 1, wherein the compound of formula I is tert-butyl (S)-N-benzyl-3-{4-[2-(3-benzyl-ureido)-thiazol-4-yl]-butyrylamino}-succinamate.

68. The compound in accordance with claim 1, wherein the compound of formula I is (S)-N-benzyl-3-{4-[2-(3-benzyl-ureido)-thiazol-4-yl]-butyrylamino}-succinamic acid trifluoroacetate.

69. The compound in accordance with claim 1, wherein the compound of formula I is ethyl 3-[4-[[2-(3-benzyl-ureido)-thiazole-4-carbonyl]-amino]-phenyl]-propionate.

70. The compound in accordance with claim 1, wherein the compound of formula I is 3-[4-[[2-(3-benzyl-ureido)-thiazole-4-carbonyl]-amino]-phenyl]-propionic acid.

71. The compound in accordance with claim 1, wherein the compound of formula I is diethyl rac-2-[3-[[2-(3-benzyl-ureido)-thiazole-4-carbonyl]-amino]-2-oxo-propyl]-succinate.

72. The compound in accordance with claim 1, wherein the compound of formula I is rac-2-[3-[[2-(3-benzyl-ureido)-thiazole-4-carbonyl]-amino]-2-oxo-propyl]-succinic acid.

73. The compound in accordance with claim 1, wherein the compound of formula I is di-tert-butyl (S)-2-(2-{[2-(3-benzyl-ureido)-thiazole-4-carbonyl]-amino}-acetylamino)-succinate.

74. The compound in accordance with claim 1, wherein the compound of formula I is (S)-2-(2-{[2-(3-benzyl-ureido)-thiazole-4-carbonyl]-amino}-acetylamino)-succinic acid trifluoroacetate.

75. The compound in accordance with claim 1, wherein the compound of formula I is tert-butyl (S)-3-[2-[[2-(3-benzyl-ureido)-thiazole-4-carbonyl]-amino]-acetylamino]-N-isobutyl-succinamate.

76. The compound in accordance with claim 1, wherein the compound of formula I is tert-butyl (S)-3-[2-[[2-(3-benzyl-ureido)-thiazole-4-carbonyl]-amino]-acetylamino]-N-pyridin-2-ylmethyl-succinamate.

77. The compound in accordance with claim 1, wherein the compound of formula I is tert-butyl (S)-3-[2-[[2-(3-benzyl-ureido)-thiazole-4-carbonyl]-amino]-acetylamino]-N-pyridin-3-ylmethyl-succinamate.

78. The compound in accordance with claim 1, wherein the compound of formula I is (S)-3-[2-[[2-(3-benzyl-ureido)-thiazole-4-carbonyl]-amino]-acetylamino]-N-pyridin-3-ylmethyl-succinamic acid trifluoroacetate.

79. The compound in accordance with claim 1, wherein the compound of formula I is (S)-3-[4-[[2-(3-benzyl-ureido)-thiazole-4-carbonyl]-amino]-phenyl]-2-tert-butoxycarbonylamino-propionic acid.

80. The compound in accordance with claim 1, wherein the compound of formula I is (R)-3-[4-[[2-(3-benzyl-ureido)-thiazole-4-carbonyl]-amino]-phenyl]-2-tert-butoxycarbonylamino-propionic acid.

81. The compound in accordance with claim 1, wherein the compound of formula I is tert-butyl (S)-N-pyridin-2-ylmethyl-3-(2-{[2-(3-pyridin-2-ylmethyl-ureido)-thiazole-4-carbonyl]-amino}-acetylamino)-succinamate.

82. The compound in accordance with claim 1, wherein the compound of formula I is (S)-N-pyridin-2-ylmethyl-3-(2-{[2-(3-pyridin-2-ylmethyl-ureido)-thiazole-4-carbonyl]-amino}-acetylamino)-succinamic acid.

83. The compound in accordance with claim 1, wherein the compound of formula I is tert-butyl 3-(3-{[2-(3-benzyl-ureido)-thiazole-4-carbonyl]-amino}-benzoylamino)-propionate.

84. The compound in accordance with claim 1, wherein the compound of formula I is 3-(3-{[2-(3-benzyl-ureido)-thiazole-4-carbonyl]-amino}-benzoylamino)-propionic acid.

85. The compound in accordance with claim 1, wherein the compound of formula I is rac 3-[2-[[(2-(3-benzyl-ureido)-thiazol-4-ylcarbonyl]-amino]-acetylamino]-3-phenyl-propionic acid.

86. The compound in accordance with claim 1, wherein the compound of formula I is 6-{[2-(3-benzyl-ureido)-thiazole-4-carbonyl]-amino}-5-oxo-hexanoic acid.

87. The compound in accordance with claim 1, wherein the compound of formula I is (S)-3-(2-{[2-(3-benzyl-ureido)-thiazole-4-carbonyl]-amino}-acetylamino)-succinic acid 4-anilide.

88. The compound in accordance with claim 1, wherein the compound of formula I is (S)-3-[2-[[2-(3-benzyl-ureido)-thiazole-4-carbonyl]-amino]-acetylamino]-N-isobutyl-succinamic acid trifluoroacetate.

89. The compound in accordance with claim 1, wherein the compound of formula I is (S)-3-(2-{[2-(3-benzyl-ureido)-thiazole-4-carbonyl]-amino}-acetylamino)-succinic acid 4-anilide 1-tert-butyl ester.

90. A process for manufacturing a compound of the formula:

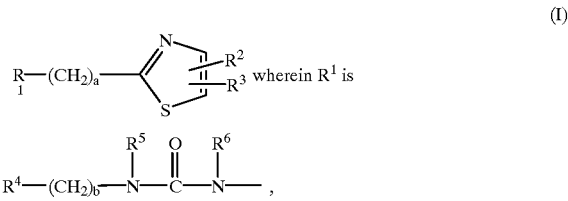

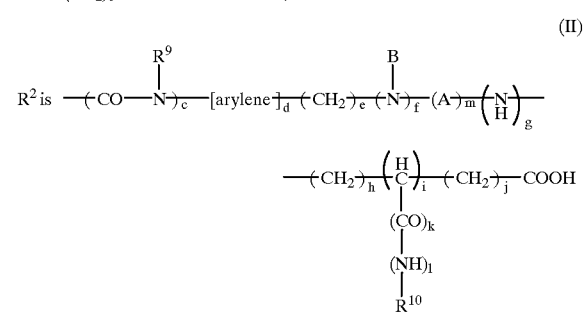

$R^3$ is hydrogen, alkyl, cycloalkyl, aryl, aralkyl, heteroaryl, carboxy, alkyl-O—CO—, or aralkyl-O—CO—;

$R^4$ is hydrogen, alkyl, cycloalkyl, aryl, or heteroaryl;

$R^5$ and $R^6$ are each independently hydrogen, alkyl, cycloalkyl, or heteroaryl;

$R^9$ is hydrogen, alkyl, or cycloalkyl;

$R^{10}$ is aryl, aralkyl, heterocyclyl, heterocyclylalkyl, hydroxy, hydrogen, or alkyl, or $R^{10}$ is carboxy, carboxyalkyl, alkyl-O—CO—, aralkyl-O—CO—, alkyl-CO—, aralkyl-CO—, heteroarylalkyl-CO—, alkylsulphonyl, arylsulphonyl or heteroarylsulphonyl and k is zero, or $R^{10}$ is an $\alpha$-amino acid bonded via the amino group and l is zero and k is 1;

A is carbonyl or sulphonyl;

B is hydrogen, alkyl, or cycloalkyl;

a is an integer from 0 to 2 but not being zero when $R^1$ is —$NH_2$; b is an integer from 0 to 4; c, d, f, g, k, l and m are each independently an integer from 0 to 1, whereby c, f and g are not simultaneously 0 and whereby m is not 0 when f or g is 1; i is an integer from 0 to 1, whereby k and l are also 0 when i is 0; e is an integer from 0 to 3; h is an integer from 0 to 5; j is an integer from 0 to 2; and the sum of e, h and j is an integer from 2 to 7;

and the pharmaceutically usable salts and esters thereof;

which process comprises reacting a compound of the formula:

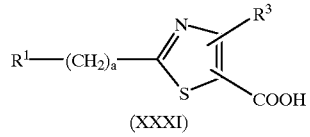

(XXXI)

with an amine of the formula:

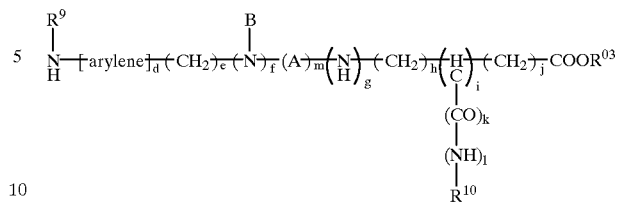

wherein $R^1$, $R^3$, $R^9$, $R^{10}$, A, B and d to m are as above, c is equal to 1 and $R^{03}$ is alkyl or aralkyl.

* * * * *